US007041491B2

(12) United States Patent
Inohara et al.

(10) Patent No.: US 7,041,491 B2
(45) Date of Patent: May 9, 2006

(54) NOD NUCLEIC ACIDS AND POLYPEPTIDES

(75) Inventors: Naohiro Inohara, Ann Arbor, MI (US); Gabriel Nuñez, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/794,342

(22) Filed: Mar. 5, 2004

(65) Prior Publication Data

US 2004/0253615 A1 Dec. 16, 2004

Related U.S. Application Data

(60) Provisional application No. 60/452,274, filed on Mar. 5, 2003.

(51) Int. Cl.
*C12N 1/20* (2006.01)
*C12N 5/00* (2006.01)
*C12N 15/00* (2006.01)
*C07H 21/04* (2006.01)

(52) U.S. Cl. .............................. 435/253.3; 435/320.1; 435/325; 536/23.5

(58) Field of Classification Search ..................... 435/6
See application file for complete search history.

(56) References Cited

FOREIGN PATENT DOCUMENTS

WO WO2004034093 * 4/2005

OTHER PUBLICATIONS

Sequence Search US-10-794-342-11.rng, May 20, 2005□□□□Sequence Search US-10-794-342-22-rag, May 17, 2005.*
Dangl and Jones, Nature 411, 826-833 (2001).
Medzhitov, Nature Rev. Immunol. 1, 135-145 (2001).
Akira et al., Nat. Immunol. 2, 675-680 (2001).
Williams, Oncogene 18, 6112-6120 (1999).
Nanduri et al., EMBO J. 19, 5567-5574 (2000).
Philpott et al., J. Immunol. 165, 903-914 (2000).
O'Riordan et al., Proc. Natl. Acad. Sci. U S A 99, 13861-13866 (2002).
Liu and Hengartner, Ann N Y Acad Sci. 887, 92-104 (1999).
Grenier et al., FEBS Lett. 530, 73-78 (2002).
Bertin et al., J. Biol. Chem. 274, 12955-12958 (1999).
Inohara et al., J. Biol. Chem. 274, 14560-14567 (1999).
Ogura et al., J. Biol. Chem. 276, 4812-4818 (2001).
Manji et al., J. Biol. Chem. 277, 11570-11575 (2002).
Geddes et al., Biochem. Biophys. Res. Commun. 284, 77-82 (2001).
Martinon et al., Mol. Cell 10, 417-426 (2002).
Yoo et al., Biochem. Biophys. Res. Commun. 299, 652-658 (2002).
Wang et al., J. Biol. Chem. 277, 29874-29880 (2002).
Poyet et al., J. Biol. Chem. 276, 28309-28313 (2001).
Hlaing et al., J. Biol. Chem. 276, 9230-9238 (2001).
Zou et al., Cell 90, 405-413 (1997).
Inohara and Nuñez, Oncogene, 20, 6473-6481 (2001).
Beg and Baltimore, Science 274, 782-784 (1996).
Wang et al., Science 281, 1680-1683 (1998).
Micheau et al., Mol. Cell. Biol. 21, 5299-5305 (2001).
Steimle et al., Cell 75, 135-146 (1993).

(Continued)

*Primary Examiner*—Kenneth R. Horlick
*Assistant Examiner*—Christopher M. Babic
(74) *Attorney, Agent, or Firm*—Medlen & Carroll, LLP

(57) ABSTRACT

The present invention relates to the NOD proteins and nucleic acids encoding the NOD proteins. The present invention further provides assays for the detection of NOD polymorphisms and mutations associated with disease states, as well as methods of screening for ligands and modulators of NOD proteins.

6 Claims, 46 Drawing Sheets

OTHER PUBLICATIONS

Reith and Mach, Annu Rev Immunol. 19, 331-373. (2001).
Ogura et al., Nature 411, 603-606 (2001).
Hugot et al., Nature 411, 599-603 (2001).
Hampe et al., Lancet 357, 1925-1928 (2001).
Miceli-Richard et al., Nat. Genet. 29, 19-20 (2001).
Bonen et al., Gastroenterology 124, 140-146 (2003).
Hoffman et al., Nature Genet. 29, 301-305 (2001).
Feldmann et al., Am. J. Hum. Genet. 71, 198-203 (2002).
Aksentijevich et al., Arthritis Rheum., 46, 3340-3348 (2002).
Aganna et al., Arthritis Rheum., 46, 2445-2452 (2002).
The International FMF Consortium, Cell 90, 797-807 (1997).

* cited by examiner

Figure 1:
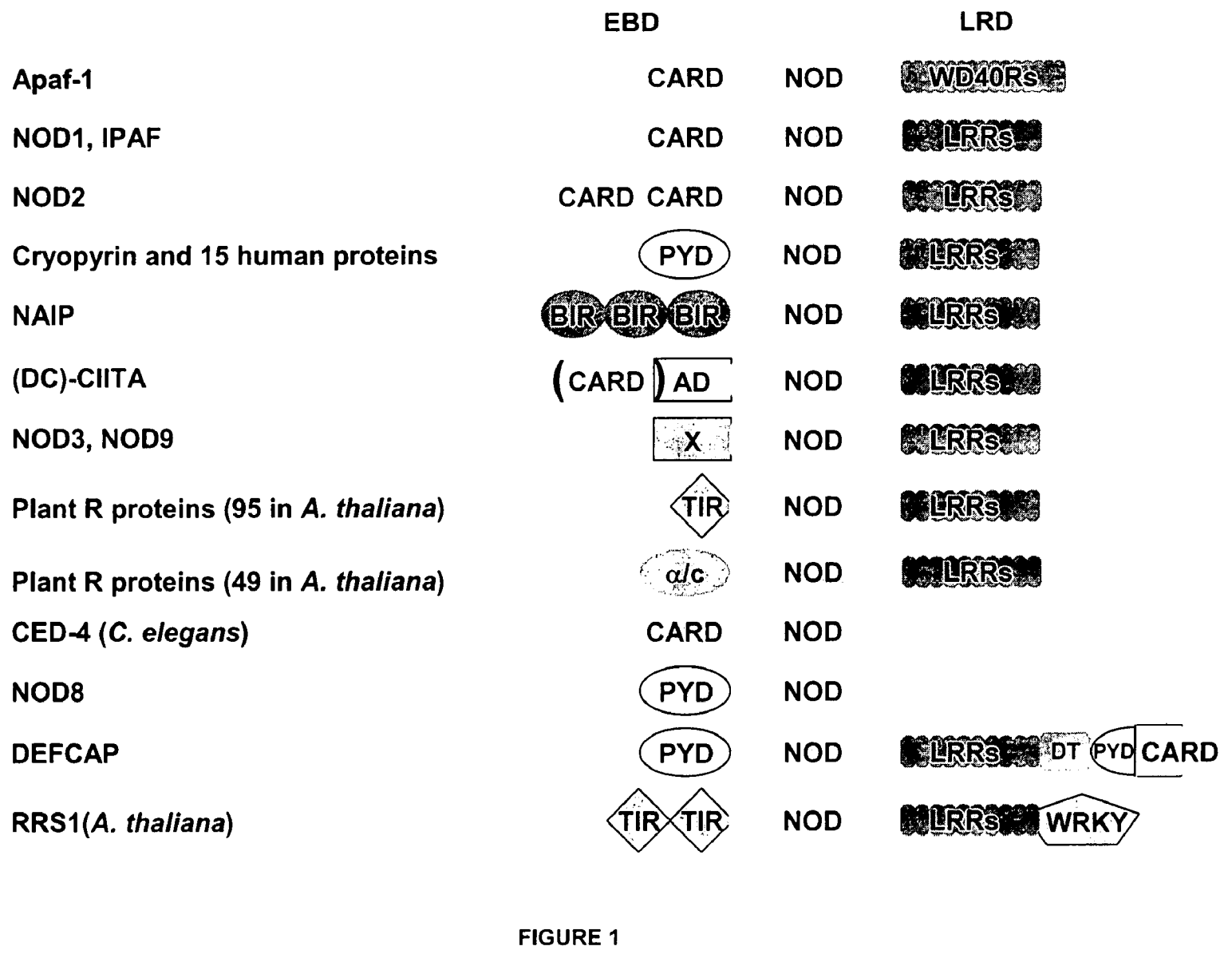

| | EBD | | LRD |
|---|---|---|---|
| Apaf-1 | CARD | NOD | WD40Rs |
| NOD1, IPAF | CARD | NOD | LRRs |
| NOD2 | CARD CARD | NOD | LRRs |
| Cryopyrin and 15 human proteins | PYD | NOD | LRRs |
| NAIP | BIR BIR BIR | NOD | LRRs |
| (DC)-CIITA | (CARD) AD | NOD | LRRs |
| NOD3, NOD9 | X | NOD | LRRs |
| Plant R proteins (95 in *A. thaliana*) | TIR | NOD | LRRs |
| Plant R proteins (49 in *A. thaliana*) | α/c | NOD | LRRs |
| CED-4 (*C. elegans*) | CARD | NOD | |
| NOD8 | PYD | NOD | |
| DEFCAP | PYD | NOD | LRRs DT PYD CARD |
| RRS1(*A. thaliana*) | TIR TIR | NOD | LRRs WRKY |

Table 2 | The human NOD protein family

| Protein | Synonyms | Locus | Expression (Inducers) | Function | EBD | Downstream Effectors | LRD | Ligand | Ref. |
|---|---|---|---|---|---|---|---|---|---|
| Apaf-1 | | 12q23 | ubiquitous (p53 stimuli) | activates caspase-9 induces apoptosis | CARD | Caspase-9 | WDR | cytochrome c | 15, 16, 51-54 |
| NOD1 | CARD4 | 7p14 | E | activates NF-κB enhances AC | CARD | RICK, (Caspase-1) | LRRs | LPS? | 26,27,55, 56, 62 |
| NOD2 | | 16q12 | M, DC, G (LPS, TNFα) | activates NF-κB enhances AC | 2 CARDs | RICK | LRRs | peptidoglycan | 28, 68,69, 84 |
| IPAF | CARD12, CLAN | 2p22 | BM, M | activates NF-κB enhances AC | CARD | (ASC, Caspase-1) | LRRs | | 32-34,59, |
| Cryopyrin | PYPAF1, NALP3 | 1q44 | PBL, C | activates NF-κB enhances AC | PYD | (ASC) | LRRs | | 29,30,37, 98 |
| PYPAF5 | | 11p15 | E, G, M | | PYD | | LRRs | | 39 |
| NOD5 | | 11p15 | | | PYD | | LRRs | | * |
| PYPAF7 | | 19q13 | G | | PYD | | LRRs | | 38 |
| MATER | PYPAF8 | 19q13 | O | | PYD | | LRRs | | 40 |
| PAN2 | PYPAF4 | 19q13 | (S, K, L, Lg, P, Th) | | PYD | | LRRs | | 39,113 |
| NALP2 | PYPAF2 | 19q13 | | | PYD | | LRRs | | 23, 39 |
| PYPAF3 | | 19q13 | | | PYD | | LRRs | | 39 |
| PYPAF4 | | 19q13 | | | PYD | | LRRs | | 39 |
| NOD6 | | 19q13 | | | PYD | | LRRs | | * |
| NOD14 | | 19q13 | | | PYD | | LRRs | | * |
| NOD16 | | 19q13 | | | PYD | | LRRs | | * |
| NOD27 | | 16q13 | | | PYD | | LRRs | | 30 |
| PYPAF6 | NOD17 | 19q13 | | | PYD | | LRRs | | 30,39 |
| NOD8 | | 11p15 | | | PYD | | (-) | | * |
| NAIP | | 5q13 | Mϕ | | 3 BIRs | | LRRs | | 41, 114 |
| ψNAIP | | 5q13 | | | BIR | | LRRs | | 42, |
| CIITA | | 16p13 | B, DC, TE (IFNγ) | MHC-II coactivator | AD | (RFX5, CBF, NF-Y) | LRRs | | 46, 47 |
| DEFCAP | NALP1, CARD7 NAC | 17p13.1 | | enhances AC | PYD, CARD | | LRRs | | 22, 23, 35, 36 |
| NOD3 | | 16p13 | | | X | | LRRs | | * |
| NOD9 | | 11q23 | | | X | | LRRs | | * |

Expression referees to mRNA levels. Cells/tissues with highest mRNA levels are indicated. Only the function and downstream effector molecules reported by two or more groups are shown. Pypaf5 has been shown to activate NF-κB and caspase-1 in the presence of ASC[39]. PAN2 has been reported to inhibit NF-κB activation[113]. Putative effectors (without genetic evidence) are shown in parenthesis. B, B cells; BM, bone marrow; C, chondrocytes; DC, dendritic cells; E, epithelium ; K, kidney; L, liver; M, monocytes; Mϕ, macrophages; O, oocytes; PBL; peripheral blood leukocytes (mixed population); S, Spleen; T, T cells; TE, thymic epithelium; WDR, WD40 repeats; X, uncharacterized domain; AC, apoptosis and/or caspase activation. *, Inohara *et al.*, unpblished.

Table 2 | NODs involved in genetic diseases

| Protein | Gene | Locus | Genetic diseases | inheritance | allelic variants | Ref |
|---|---|---|---|---|---|---|
| NOD2 | CARD15 | 16q12 | Crohn's disease | recessive | L1007fsInsC, G908R, R702W | 66,90,91 |
| | | | Blau syndrome | dominant | R334W, R334Q, L469F | 92,93 |
| Cryopyrin | CIAS1 | 1q44 | FCU(FCAS) | dominant | R260W, V198M, L305P, L353P, A439V, E627G | 37, 95 |
| | | | MWS | dominant | R260W, V198M, D303N, A352V, A439T, G569R | 37,95 |
| | | | NOMID(CINCA) | dominant | R260W, D303N, Q306L, F309S, H358R, T436N, F573S, M662T | 96, 97 |
| CIITA | MHC2TA | 16p13 | BLS II | recessive | Δ24(IVSDS G-A), E381ter, W688ter, 991del, ΔI1027, Δ28(IVSDS G-A), L469P | 46,47,89 |
| Pyrin | MEFV | 16p13 | FMF | recessive | M697I, V726A, M680I, E167D, (E148Q), P369S, R408Q, R653H, E148V, T267I, F479L, I692del, K695R, A744S, R761H | 13, 99, 100 |
| NAIP | BIRC1E | 5q13 | Lgn1(mouse) | recessive | N.D. | 109,110 |

The amino acid residue numbers shown here are based on the sequence of NOD2a and B-type CIITA[28,47]. IVSDS G-A are splice donor mutations with a G-to-A transition. N.D., the precise mutation in Lgn1 locus has not been determined. Human NAIP gene (BIRC1) is located on 5q13 (ref. 41) and mouse paralogue gene BIRC1E encoding NAIP5 is located on chromosome 13 (ref 109,110).

Figure 7
SEQ ID NO:1

```
1 tgagaactca ggctggcaca gggattccca gggcatctac caccacgcag ctggagcagg
61 gctgagccca ggagcatgga gatggacgcc cccaggcccc ccagtcttgc tgtccctgga
121 gcagcatcga ggcccgggag gctgctggat gggggcacg gcaggcagca ggttcaggcc
181 ctctcttcac agctcctgga ggtgatcccc gactccatga ggaagcaaga ggtgcggacg
241 ggcagggagg ccggccaggg ccacggtacg ggctccccag ccgagcaggt gaaagccctc
301 atggatctgc tggctgggaa gggcagtcaa ggctcccacg ccccgcaggc cctggatagg
361 acaccggatg ccccgctggg gccctgcagc aatgactcaa ggatacagag gcaccgcaag
421 gccctgctga gcaaggtggg aggtggcccg gagctgggcg gaccctggca caggctggcc
481 tccctcctgc tggtggaggg cctgacggac ctgcagctga gggaacacga cttcacacag
541 gtggaggcca cccgcggggg cgggcacccc gccaggaccg tcgccctgga ccggctcttc
601 ctgcctctct cccgggtgtc tgtcccaccc cgggtctcca tcactatcgg ggtggccggc
661 atgggcaaga ccaccctggt gaggcacttc gtccgcctct gggcccatgg gcaggtcggc
721 aaggacttct cgctggtgct gcctctgacc ttccgggatc tcaacaccca cgagaagctg
781 tgtgccgacc gactcatctg ctcggtcttc ccgcacgtcg gggagcccag cctggcggtg
841 gcagtcccag ccagggccct cctgatcctg gacggcttgg atgagtgcag gacgcctctg
901 gacttctcca acaccgtggc ctgcacggac ccaaagaagg agatcccggt ggaccacctg
961 atcaccaaca tcatccgtgg caacctcttt ccggaagttt ccatctggat cacctcccgt
1021 cccagtgcat ctggccagat cccagggggc ctggtggacc ggatgacgga gatccggggc
1081 tttaacgagg aggagatcaa ggtgtgtttg gagcagatgt tccccgagga ccaggccctt
1141 ctgggctgga tgctgagcca agtgcaggct gacagggccc tgtacctgat gtgcaccgtc
1201 ccagccttct gcaggctcac ggggatggcg ctaggccacc tgtggcgcag caggacgggg
1261 ccccaggatg cagagctgtg gcccccgagg accctgtgcg agctctactc atggtacttt
1321 aggatggccc tcagcgggga ggggcaggag aagggcaagg caagccctcg catcgagcag
1381 gtggcccatg gtggccgcaa gatggtgggg acattgggcc gtctggcctt ccatgggctg
1441 ctcaagaaga aatacgtgtt ttacgagcaa gacatgaagg cgtttggtgt agacctcgct
1501 ctgctgcagg gcgccccgtg cagctgcttc ctgcagagag aggagacgtt ggcatcgtca
1561 gtggcctact gcttcaccca cctgtccctg caggagtttg tggcagccgc gtattactat
1621 ggcgcatcca ggagggccat cttcgacctc ttcactgaga gcggcgtatc ctggcccagg
1681 ctgggcttcc tcacgcattt caggagcgca gcccagcggg ccatgcaggc agaggacggg
1741 aggctggacg tgttcctgcg cttcctctcc ggcctcttgt ctccgagggt caatgccctc
1801 ctggccggct ccctgctggc ccaaggcgag caccaggcct accggaccca ggtggctgag
1861 ctcctgcagg gctgcctgcg ccccgatgcc gcagtctgtg cacgggccat caacgtgttg
1921 cactgcctgc atgagctgca gcacaccgag ctggcccgca gcgtggagga ggccatggag
1981 agcggggccc tggccaggct gactggtccc gcgcaccgcg ctgccctggc ctacctcctg
2041 caggtgtccg acgcctgtgc ccaggaggcc aacctgtccc tgagcctcag ccagggcgtc
2101 cttcagagcc tgctgcccca gctgctctac tgccggaagc tcaggctgga caccaaccag
2161 ttccaggacc ccgtgatgga gctgctgggc agcgtgctga gtgggaagga ctgtcgcatt
2221 cagaagatca gcttggcgga gaaccagatc agtaacaaag ggccaaagc tctggccaga
2281 tccctcttgg tcaacagaag tctgacctct ctggacctcc gcggtaactc cattggacca
2341 caaggggcca aggcgctggc agacgctttg aagatcaacc gcaccctgac ctccctgagc
2401 ctccagggca acaccgttag ggatgatggt gccaggtcca tggctgaggc cttggcctcc
2461 aaccggaccc tctccatgct gcacctgcag aagaacagca tcgggcccat gggagcccag
2521 cggatggcag atgccttgaa gcagaacagg agtctgaaag agctcatgtt ctccagtaat
2581 agtattggtg atggaggtgc caaggccctg gctgaggccc tgaaggtgaa ccagggcctg
2641 gagagcctgg acctgcagag caattccatc agtgacgcag gagtggcagc actgatgggg
2701 gccctctgca ccaaccagac cctcctcagc ctcagccttc gagaaaactc catcagtccc
2761 gagggagccc aggccatcgc tcatgccctc tgcgccaaca gcaccctgaa gaacctggac
2821 ctgacagcca acctcctcca cgaccagggt gcccgggcca tcgcagtggc agtgagagaa
2881 aaccgcaccc tcacctccct tcacctgcag tggaacttca tccaggccgg cgctgcccag
```

```
2941 gccctgggac aagcactaca gctcaacagg agcctcacca gcttagattt acaggagaac
3001 gccatcgggg atgacggagc gtgtgcggtg gcccgtgcac tgaaggtcaa cacagccctc
3061 actgctctct atctccaggt ggcctcaatt ggtgcttcag gcgcccaggt gctaggggaa
3121 gccttggctg tgaacagaac cttggagatt ctcgacttaa gaggaaatgc cattggggtg
3181 gctggagcca aagccctggc aaatgctctg aaggtaaact caagtctccg gagactcaat
3241 cttcaagaga attctctggg gatggacggg gcgatatgca ttgccacagc actgtctgga
3301 aaccacaggc tccagcatat caatctccag ggaaaccaca ttggggactc cggggccagg
3361 atgatctcag aggccatcaa gacaaatgct cccacgtgca ctgttgaaat gtga
```

Figure 8
SEQ ID NO:12 aggcctgaatatttggacaagATGGCAGATTCATCATCATCTTCTTTCTTTCCTGATTTTGG
GCTGCTATTGTATTTGGAGGAGCTAAACAAAGAGGAATTAAATACATTCAAG
TTATTCCTAAAGGAGACCATGGAACCTGAGCATGGCCTGACACCCTGGAATG
AAGTGAAGAAGGCCAGGCGGGAGGACCTGGCCAATTTGATGAAGAAATATT
ATCCAGGAGAGAAAGCCTGGAGTGTGTCTCTCAAAATCTTTGGCAAGATGAA
CCTGAAGGATCTGTGTGAGAGAGCGAAAGAAGAGATCAACTGGTCGGCCCA
GACTATAGGACCAGATGATGCCAAGGCTGGAGAGACACAAGAAGATCAGGA
GGCAGTGCTGGGTGATGGAACAGAATACAGAAATAGAATAAAGGAAAAATT
TTGCATCACTTGGGACAAGAAGTCTTTGGCTGGAAAGCCTGAAGATTTCCATC
ATGGAATTGCAGAGAAAGATAGAAAACTGTTGGAACACTTGTTCGATGTGGA
TGTCAAAACCGGTGCACAGCCACAGATCGTGGTGCTTCAGGGAGCTGCTGGA
GTTGGGAAAACAACCTTGGTGAGAAAGGCAATGTTAGATTGGGCAGAGGGC
AGTCTCTACCAGCAGAGGTTTAAGTATGTTTTTATCTCAATGGGAGAGAAAT
TAACCAGCTGAAAGAGAGAAGCTTTGCTCAATTGATATCAAAGGACTGGCCC
AGCACAGAAGGCCCCATTGAAGAAATCATGTACCAGCCAAGTAGCCTCTTGT
TTATTATTGACAGTTTCGATGAACTGAACTTTGCCTTTGAAGAACCTGAGTTT
GCACTGTGCGAAGACTGGACCCAAGAACACCCAGTGTCCTTCCTCATGAGTA
GTTTGCTGAGGAAAGTGATGCTCCCTGAGGCATCCTTATTGGTGACAACAAG
ACTCACAACTTCTAAGAGACTAAAGCAGTTGTTGAAGAATCACCATTATGTA
GAGCTACTAGGAATGTCTGAGGATGCAAGAGAGGAGTATATTTACCAGTTTT
TTGAAGATAAGAGGTGGGCCATGAAAGTATTCAGTTCACTAAAAAGCAATGA
GATGCTGTTTAGCATGTGCCAAGTCCCCCTAGTGTGCTGGGCCGCTTGTACTT
GTCTGAAGCAGCAAATGGAGAAGGGTGGTGATGTCACATTGACCTGCCAAAC
AACCACAGCTCTGTTTACCTGCTATATTTCTAGCTTGTTCACACCAGTAGATG
GAGGCTCTCCTAGTCTACCCAACCAAGCCCAGCTGAGAAGACTGTGCCAAGT
CGCTGCCAAAGGAATATGGACTATGACTTACGTGTTTTACAGAGAAAATCTC
AGAAGGCTTGGGTTAACTCAATCTGATGTCTCTAGTTTTATGGACAGCAATAT
TATTCAGAAGGACGCAGAGTATGAAAACTGCTATGTGTTCACCCACCTTCAT
GTTCAGGAGTTTTTTGCAGCTATGTTCTATATGTTGAAAGGCAGTTGGGAAGC
TGGGAACCCTTCCTGCCAGCCTTTTGAAGATTTGAAGTCATTACTTCAAAGCA
CAAGTTATAAAGACCCCCATTTGACACAGATGAAGTGCTTTTTGTTTGGCCTT
TTGAATGAAGATCGAGTAAAACAACTGGAGAGGACTTTTAACTGTAAAATGT
CACTGAAGATAAAATCAAAGTTACTTCAGTGTATGGAAGTATTAGGAAACAG
TGACTATTCTCCATCACAGCTGGGATTTCTGGAGTTGTTTCACTGTCTGTATG
AGACTCAAGATAAAGCGTTTATAAGCCAGGCAATGAGATGTTTCCCAAAGGT
TGCCATTAATATTTGTGAGAAAATACATTTGCTTGTATCTTCTTTCTGCCTTAA
GCACTGCCGGTGTTTGCGGACCATCAGGCTGTCTGTAACTGTGGTATTTGAGA
AGAAGATATTAAAAACAAGCCTCCCAACTAACACTTGGGATGGTGATCGCAT
TACTCACTGTTGGCAAGATCTCTGTTCTGTGCTTCATACAAATGAACACTTGA GAGAATTGGACCTGTACCATAGCAACCTTGATAAATCAGCAATGAATATCCT
GCATCATGAACTAAGGCACCCAAACTGTAAACTACAAAAGCTACTGTTGAAA
TTTATCACTTTCCCTGATGGTTGTCAGGATATCTCTACTTCTTTGATTCATAAC
AAGAATCTGATGCATCTTGACCTAAAAGGGAGTGATATAGGGGATAATGGAG
TAAAGTCATTGTGTGAGGCCTTGAAACACCCAGAGTGTAAACTACAGACTCT
CAGGCTGGAATCTTGCAACCTAACTGTATTTTGTTGTCTAAATATATCTAATG
CTCTCATCAGAAGCCAGAGCCTGATATTTCTGAATCTGTCAACCAATAATCTG
TTGGATGATGGAGTGCAGCTTTTGTGTGAGGCCTTAAGACATCCAAAGTGTTA
TCTAGAGAGACTGTCCTTAGAAAGCTGTGGTCTCACAGAGGCTGGCTGTGAG
TATCTTTCTTTGGCTCTCATCAGCAATAAAAGACTGACACATTTGTGCTTGGC
AGACAATGTCTTGGGTGATGGTGGAGTAAAGCTTATGAGTGATGCCCTGCAA
CATGCACAATGTACTCTGAAGAGCCTTGTGCTGAGGCGTTGCCATTTCACTTC
ACTTAGCAGTGAATATCTGTCAACTTCTCTTCTACACAACAAGAGCCTGACGC
ATCTGGATCTAGGATCAAACTGGCTACAAGACAATGGAGTGAAGCTTCTGTG
TGATGTCTTTCGGCATCCAAGCTGTAATCTTCAGGACTTGGAATTGATGGGCT
GTGTTCTCACTAATGCATGTTGTCTGGATCTGGCTTCTGTTATTTGAATAACC
CAAACCTGAGGAGCCTGGACCTTGGGAACAACGATTTGCAGGATGATGGAGT
GAAAATTCTGTGTGATGCTTTGAGATATCCAAACTGTAACATTCAGAGGCTCG
GGTTGGAATACTGTGGTTTGACATCTCTCTGCTGTCAAGATCTCTCCTCTGCTC
TTATCTGCAACAAAAGACTGATAAAAATGAATCTGACACAGAATACCTTAGG
ATATGAAGGAATTGTGAAGTTATATAAAGTCTTGAAGTCTCCTAAGTGTAAA
CTACAAGTTCTAGGGTTGTGCAAAGAGGCATTTGATGAGGAAGCCCAGAAGC
TGCTGGAAGCTGTGGGAGTTAGCAATCCACACTTAATCATTAAGCCAGATTG
TAACTATCATAATGAAGAAGATGTGTCTTGGTGGTGGTGTTTCTGAtttgaagaaact
gacattcctttaaaaatataaatataaatacatacatacatagatatatacccagacttgggtgcttagcttcagatactctatgccca
gagatagtgcacttggcagctgtcagataccattcatctacttctctgtaaaatgtctgttctacttcacacagtggtcgagaggcta
aAATAAAatgaaaagcataaaactctctg

Figure 9
SEQ ID NO:3

```
   1 acacctcagt tcacaatcct ggggcgatat ggcagaatct ttttttcgg
atttggctt
  61 gttgtggtat ctgaaggagc tcagaaagga agagttttgg aaatttaagg
agctcctcaa
 121 acaacctttg gagaaatttg aactcaagcc aatcccctgg gctgagctga
agaaggcctc
 181 caaagaagat gtagcaaagc tgctggacaa acattaccca ggaaagcagg
catgggaggt
 241 aacactgaac ctgtttctac agatcaatag gaaagatctc tggacaaagg
ctcaggaaga
 301 gatgagaaat aagctaaacc catacagaaa gcatatgaag gaaacatttc
aactcatatg
 361 ggagaaggaa acctgtcttc acgtccctga gcatttctac aaagaaacca
tgaaaaatga
 421 gtataaagaa ttgaatgacg catatactgc tgcggctaga cgacacactg
tggtcctgga
 481 aggtcctgat ggaattggaa aaacaaccct tttaagaaaa gtgatgttgg
actgggcaga
 541 gggaaactta tggaaggaca ggttcacatt tgtgtttttc ctcaatgtct
gtgaaatgaa
 601 cggtatcgca gagaccagct tactggagct cctctctagg gactggccgg
agtcttcaga
 661 gaagatcgaa gacatttttt cccagccaga gagaattctg ttcatcatgg
atggctttga
 721 gcaactgaag tttaacttac aacttaaggc tgacttgagc gatgattgga
ggcagcggca
 781 gccaatgcca attatcctga gcagtttgtt gcaaaaaaag atgcttccag
aatcctctct
 841 ccttattgca ttaggaaaac tggctatgca aaaacactat tttatgttgc
ggcatccaaa
 901 actcataaag ctcttaggat tcagtgaatc tgaaaagaag tcgtatttct
cctacttctt
 961 tggtgagaag agcaaagccc tgaaagtctt caattttgtg agagataatg
ggccgctgtt
1021 tatcttgtgc cataatccct ttacgtgctg gttggtctgt acttgtgtga
aacagaggct
1081 agagagggga gaagaccttg aaataaactc ccaaaacacc acctatttat
atgcatcctt
1141 tttaacaact gtattcaaag caggaagtca gagttttcca cctaaggtga
acagagcccg
1201 actaaaaagc ctgtgtgctt tggctgcaga gggaatttgg acatatacat
ttgtattttc
1261 ccatggggat ctccggagga atgggttatc tgagtctgag ggcgtgatgt
gggtgggtat
1321 gagactcctc caaaggagag ggactgttt tgccttcatg catctgtgta
tccaagagtt
1381 ttgtgccgcc atgttttatt tgctcaaacg acccaaagac gatcctaacc
cggccattgg
```

1441 aagcataacc cagcttgtaa gagcaagtgt ggttcagcct caaaccctct tgacccaggt
1501 ggggatattc atgtttggaa tttcaacaga agaaatcgtc agcatgctgg agacctcctt
1561 tggttttcca ctgtcaaaag acctaaagca ggaaataacc caatgccttg aaagtttaag
1621 tcaatgtgaa gctgataggg aagccatagc tttccaggaa ctattcattg gtttgtttga
1681 aactcaggaa aaagaatttg taaccaaagt gatgaatttc tttgaagaag ttttcattta
1741 tattggtaac atagaacatt tggtaatagc ttcattctgc ctgaagcatt gtcaacattt
1801 aacgacactt cgcatgtgtg tggagaatat ctttccagat gactcaggat gcatctcaga
1861 ttacaatgag aagctcgtct actggcggga gctttgctca atgttcatta ccaacaagaa
1921 cttccagatt ttagacatgg aaaataccag ccttgatgat ccctccctgg cgattctttg
1981 caaagcgctg gctcagcctg tttgtaaact ccgaaaactc atatttactt ctgtgtactt
2041 tggacatgat tcagaattat ttaaggcagt tcttcacaac cctcatctga aacttctgag
2101 cctgtacggc actagcctct cccagtctga catcagacac ctgtgtgaga cgctgaaaca
2161 tccaatgtgc aagatagaag agctgatact gggaaagtgt gacatctcca gtgaagtttg
2221 tgaagacatc gcctccgtcc tggcctgcaa cagcaagctg aaacacctct ccttggtaga
2281 aaatcccttg agggacgaag gaatgacgtt gctgtgtgaa gccctgaagc actcacactg
2341 tgccctggag aggctgatgt tgatgtactg ctgtctcacc tctgtctcct gtgactccat
2401 ttccgaagtc ctcttgtgca gtaagtccct gtccctcctc gatctgggct caaatgccct
2461 ggaagataat ggagtggcat ctctgtgtgc agcgctgaag cacccaggct gcagcatacg
2521 ggagctgtgg ttgatgggct gtttccttac ttccgattcc tgtaaggaca ttgctgctgt
2581 tcttatttgc aatgggaaac tgaagaccct gaaacttggg cataatgaaa taggagacac
2641 tggtgtcaga cagttatgtg cagctttgca gcatcctcac tgtaaattag agtgtctcgg
2701 gctgcaaacg tgtccgatca cccgtgcctg ctgcgacgac atcgccgcag cactcatcgc
2761 ctgcaaaaca ctgaggagcc tgaacctcga ctggattgcc ttggatgctg atgcagtggt
2821 ggtgctgtgt gaggcattga gccacccgga ctgtgccctg cagatgctgg ggctgcacaa
2881 atctggcttt gatgaagaaa ctcagaagat cctgatgtct gtggaagaaa aaattcccca
2941 tctgaccatt tcacatggac cttggattga cgaggaatac aagatcaggg gtgtgctcct
3001 ctgatgggga acaccctgaa gtagtcgtct cacaaaggct ttccttggcc acagtgggac
3061 cttcacctgg cacctctatc ctgtaattgc acatcatggc agcagggctg tgatttcaga 3121 ggtactccct aagtgttcta gcaatatgat tatggagtgt gattcagtgt acatgctgat
3181 tgtctttgcc tcggtcctat atccccttgt ctttagaaat cccatcctgc cttgtgatat
3241 ttagaagcac aagtacgtta aacaagtgct aaacgctctg gaaagcatgg ctttattttc
3301 ttaatggatg tcttggtgtg taggagcatg catttgtagg caccacaatc cggatacttc
3361 tgacacagaa gtgatgctag aatgtgtcta tagattgtat tgctagcatc cagactttct
3421 agtttgtcca gatttcgatt tgatcaattt tcttgtccaa taaaaaagca tttccaaatc
3481 tcta

Figure 10
SEQ ID NO:4

```
   1 atcaccatgg ccatggccaa ggccagaaag ccccgggagg cattgctctg
ggccttgagt
  61 gaccttgagg agaacgattt caagaagtta aagttctact tacgggatat
gaccctgtct
 121 gagggccagc cccactggc cagaggggag ttggagggcc tgattccggt
ggacctggca
 181 gaattactga tttcaaagta tggagaaaag gaggctgtga aagttgtcct
caagggcttg
 241 aaggtcatga acctgttgga acttgtggac cagctcagcc atatttgtct
gcatgattac
 301 agagaagtat accgagagca tgtgcgctgc ctagaggaat ggcaggaagc
aggagtcaat
 361 ggcagataca accaggtgct cctggtggcc aagcccagct cagagagccc
agaatcactt
 421 gcctgcccct tcccggagca ggagctggag tctgtcacgg tggaggctct
atttgattca
 481 ggggaaaagc cctcactggc cccatcctta gttgtgctac aggggtcggc
tggcactgga
 541 aagacaactc tcgccagaaa aatggtgttg gactgggcca ccggtactct
gtacccaggc
 601 cggtttgatt atgtctttta tgtaagctgc aaagaagtgg tcctgctgct
ggagagcaaa
 661 ctggagcagc tccttttctg gtgctgcggg gacaatcaag cccctgtcac
agagattctg
 721 aggcagccag agcggctcct gttcatcctg gatggctttg atgagctgca
gaggcccttt
 781 gaagaaaagt tgaagaagag ggtttgagt cccaaggaga gcctgctgca
ccttctaatt
 841 aggagacata cactccccac gtgctcccct ctcatcacca cccggcccct
ggctttgagg
 901 aatctggagc ccttgctgaa acaagcacgt catgtccata tcctaggctt
ctctgaggag
 961 gagagggcga ggtacttcag ctcctatttc acggatgaga agcaagctga
ccgtgccttc
1021 gacattgtac agaaaaatga cattctctac aaagcgtgtc aggttccagg
catttgctgg
1081 gtggtctgct cctggctgca ggggcagatg gagagaggca aagttgtctt
agagacacct
1141 agaaacagca ctgacatctt catggcttac gtctccacct ttctgccgcc
cgatgatgat
1201 gggggctgct ccgagctttc ccggcacagg gtcctgagga gtctgtgctc
cctagcagct
1261 gaagggattc agcaccagag gttcctattt gaagaagctg agctcaggaa
acataattta
1321 gatggcccca ggcttgccgc tttcctgagt agtaacgact accaattggg
acttgccatc
1381 aagaagttct acagcttccg ccacatcagc ttccaggact tttttcatgc
catgtcttac
```

1441 ctggtgaaag aggaccaaag ccggctgggg aaggagtccc gcagagaagt gcaaaggctg
1501 ctggaggtaa aggagcagga agggaatgat gagatgaccc tcactatgca gtttttactg
1561 gacatctcga aaaaagacag cttctcgaac ttggagctca agttctgctt cagaatttct
1621 ccctgtttag cgcaggatct gaagcatttt aaagaacaga tggaatctat gaagcacaac
1681 aggacctggg atttggaatt ctccctgtat gaagctaaaa taaagaatct ggtaaaaggt
1741 attcagatga acaatgtatc attcaagata aaacattcaa atgaaaagaa atcacagagc
1801 cagaatttat tttctgtcaa aagcagcttg agtcatggac ctaaggagga gcaaaaatgt
1861 ccttctgtcc atggacagaa ggagggcaaa gataatatag caggaacaca aaaggaagct
1921 tctactggaa aaggcagagg gacagaggaa acaccaaaaa atacttacat ataa

Figure 11
SEQ ID NO:5

```
1 gctctgacct tctttcccag gatgaggtgg ggccaccatt tgcccagggc ctcttggggc
61 tctggtttta gaagagcact ccagcgacca gatgatcgta tccccttcct gatccactgg
121 agttggcccc ttcaagggga gcgtcccttt gggcccccta gggcctttat acgccaccac
181 ggaagctcgg tagatagcgc tcccccatcc gggaggcatg gacggctgtt ccccagcgcc
241 tctgcaactg aagctataca gcggcaccgc cggaacctgg ctgagtggtt cagccggctg
301 cccagggagg agcgccagtt tggcccaacc tttgccctag acacggtcca cgttgaccct
361 gtgatccgcg agagtacccc tgatgagcta cttcgcccac ccgcggagct ggccctggag
421 catcagccac cccaggccgg gctccccccca ctggccttgt ctcagctctt taacccggat
481 gcctgtgggc gccgggtgca gacagtggtg ctgtatggga cagtgggcac aggcaagagc
541 acgctggtgc gcaagatggt tctggactgg tgttatgggc ggctgccggc cttcgagctg
601 ctcatcccct tctcctgtga ggacctgtca tccctgggcc ctgccccagc ctccctgtgc
661 caacttgtgg cccagcgcta cacgcccctg aaggaggttc tgcccctgat ggctgctgct
721 gggtcccacc tcctctttgt gctccatggc ttagagcatc tcaacctcga cttccggctg
781 gcaggcacgg gactttgtag tgacccggag gaaccgcagg aaccagctgc tatcatcgtc
841 aacctgctgc gcaaatacat gctgcctcag gccagcattc tggtgaccac tcggccctct
901 gccattggcc gtatccccag caagtacgtg ggccgctatg gtgagatctg cggtttctct
961 gataccaacc tgcagaagct ctacttccag ctccgcctca accagccgta ctgcgggtat
1021 gccgttggcg gttcaggtgt ctctgccaca ccagctcagc gtgaccacct ggtgcagatg
1081 ctctcccgga acctggaggg gcaccaccag atagccgctg cctgcttcct gccgtcctat
1141 tgctggctcg tttgtgccac cttgcacttc ctgcatgccc ccacgcctgc tgggcagacc
1201 cttacaagca tctataccag cttcctgcgc ctcaacttca gcggggaaac cctggacagc
1261 actgacccct ccaatttgtc cctgatggcc tatgcagccc gaaccatggg caagttggcc
1321 tatgaggggg tgtcctcccg caagacctac ttctctgaag aggatgtctg tggctgcctg
1381 gaggctggca tcaggacgga ggaggagttt cagctgctgc acatcttccg tcgggatgcc
1441 ctgaggtttt tcctggcccc atgtgtggag ccagggcgtg caggcacctt cgtgttcacc
```

1501 gtgcccgcca tgcaggaata cctggctgcc ctctacattg tgctgggttt gcgcaagacg
1561 accctgcaaa aggtgggcaa ggaagtggct gagctcgtgg gccgtgttgg ggaggacgtc
1621 agcctggtac tgggcatcat ggccaagctg ctgcctctgc gggctctgcc tctgctcttc
1681 aacctgatca aggtggttcc acgagtgttt gggcgcatgg tgggtaaaag ccgggaggcg
1741 gtggctcagg ccatggtgct ggagatgttt cgagaggagg actactacaa cgatgatgtt
1801 ctggaccaga tgggcgccag tatcctgggc gtggagggcc cccggcgcca cccagatgag
1861 ccccctgagg atgaagtctt cgagctcttc cccatgttca tgggggggct tctctctgcc
1921 cacaaccgag ctgtgctagc tcagcttggc tgccccatca agaacctgga tgccctggag
1981 aatgcccagg ccatcaagaa gaagctgggc aagctgggcc ggcaggtgct gcccccatca
2041 gagctccttg accacctctt cttccactat gagttccaga accagcgctt ctccgctgag
2101 gtgctcagct ccctgcgtca gctcaacctg gcaggtgtgc gcatgacacc agtcaagtgc
2161 acagtggtgg cagctgtgct gggcagcgga aggcatgccc tggatgaggt gaacttggcc
2221 tcctgccagc tagatcctgc tgggctgcgc acactcctgc ctgtcttcct gcgtgcccgg
2281 aagctgggct tgcaactcaa cagcctgggc cctgaggcct gcaaggacct ccgagacctg
2341 ttgctgcatg accagtgcca aattaccaca ctgcggctgt ccaacaaccc gctgacggag
2401 gcaggtgttg ccgtgctaat ggaggggctg gcaggaaaca cctcagtgac gcacctgtcc
2461 ctgctgcaca cgggccttgg ggacgaaggc ctggagctgc tggctgccca gctggaccgc
2521 aaccggcagc tgcaggagct gaacgtggcg tacaacggtg ctggtgacac agcggccctg
2581 gccctggcca gagctgcccg ggagcaccct tccctggaac tgctacacct ctacttcaat
2641 gagctgagct cagagggccg ccaggtcttg cgagacttgg ggggtgctgc tgaaggtggt
2701 gcccgggtgg tggtgtcact gacagagggg acggcggtgt cagaatactg gtcagtgatc
2761 ctcagtgaag tccagcggaa cctcaatagc tgggatcggg cccgggttca gcgacacctt
2821 gagctcctac tgcgggatct ggaagatagc cggggtgcca cccttaatcc ttggcgcaag
2881 gcccagctgc tgcgagtgga gggcgaggtc agggccctcc tggagcagct gggaagctct
2941 ggaagctgag acactggcgg caggcaccta gctatgtgac cactggccct aaaccttttc
3001 cctctgtggc ctcctggctt gcactgctcc ctctagaaag attccttcag gtctggaggc
3061 agaggaatgg gcatagctga gccagttgcc ctcctagggc atgtttgacc aggactgagt
3121 ctggaatctc caagttaaag atggtgaatc aatgcttcgg gcttggagat ggaacatgcc 3181 tcctctccat tcagctagaa ggaccaaagc atgtggcatt tggatggcca gagtgccctg
3241 aagcaccact accaaccttg cctccccctc ctctcaaaga gcctctgatt gtgtcaccaa
3301 ggggctcaca tcttatgtct gccatgccag gggtgtcgcc atccagatgt gttggaagct
3361 tcccctcctg ccttatgctc acctgtggac accgaggatg ccctcacatt ggtgctttct
3421 cctcatcctc atgccccctt tgccacaatg gtatgatggc ttggtagccc ctcgaggcag
3481 atgcacctga cttgctgcta ttaaaagcc gtgtgccttc tacca

Figure 12
SEQ ID NO:6

```
1 ttcttcagcc ttaacctaag gtctcatact cggagcacta tgacatcgcc ccagctagag
61 tggactctgc agacccttct ggagcagctg aacgaggatg aattaaagag tttcaaatcc
121 cttttatggg cttttcccct cgaagacgtg ctacagaaga ccccatggtc tgaggtggaa
181 gaggctgatg gcgagaaact ggcagaaatt ctggtcaaca cctcctcaga aaattggata
241 aggaatgcga ctgtgaacat cttggaagag atgaatctca cggaattgtg taagatggca
301 aaggctgaga tgatggagga cggacaggtg caagaaatag ataatcctga gctgggagat
361 gcagaagaag actcggagtt agcaaagcca ggtgaaaagg aaggatggag aaattcaatg
421 gagaaacagt ctttggtctg gaagaacacc ttttggcaag gagacattga caatttccat
481 gacgacgtca ctctgagaaa ccaacggttc attccattct tgaatcccag aacacccagg
541 aagctaacac cttacacggt ggtgctgcac ggccccgcag gcgtggggaa aaccacgctg
601 gccaaaaagt gtatgctgga ctggacagac tgcaacctca gcccgacgct cagatacgcg
661 ttctacctca gctgcaagga gctcagccgc atgggcccct gcagttttgc agagctgatc
721 tccaaagact ggcctgaatt gcaggatgac attccaagca tcctagccca agcacagaga
781 atcctgttcg tggtcgatgg ccttgatgag ctgaaagtcc cacctggggc gctgatccag
841 gacatctgcg gggactggga gaagaagaag ccggtgcccg tcctcctggg gagtttgctg
901 aagaggaaga tgttacccag ggcagccttg ctggtcacca cgcggcccag ggcactgagg
961 gacctccagc tcctggcgca gcagccgatc tacgtaaggg tggagggctt cctggaggag
1021 gacaggaggg cctatttcct gagacacttt ggagacgagg accaagccat gcgtgccttt
1081 gagctaatga ggagcaacgc ggccctgttc cagctgggct cggcccccgc ggtgtgctgg
1141 attgtgtgca cgactctgaa gctgcagatg gagaaggggg aggacccggt ccccacctgc
1201 ctcacccgca cggggctgtt cctgcgtttc ctctgcagcc ggttcccgca gggcgcacag
1261 ctgcggggcg cgctgcggac gctgagcctc ctggccgcgc agggcctgtg ggcgcagatg
1321 tccgtgttcc accgagagga cctggaaagg ctcggggtgc aggagtccga cctccgtctg
1381 ttcctggacg gagacatcct ccgccaggac agagtctcca aaggctgcta ctccttcatc
```

1441 cacctcagct tccagcagtt tctcactgcc ctgttctacg ccctggagaa ggaggagggg
1501 gaggacaggg acggccacgc ctgggacatc ggggacgtac agaagctgct ttccggagaa
1561 gaaagactca agaaccccga cctgattcaa gtaggacact tcttattcgg cctcgctaac
1621 gagaagagag ccaaggagtt ggaggccact tttggctgcc ggatgtcacc ggacatcaaa
1681 caggaattgc tgcaatgcaa agcacatctt catgcaaata agcccttatc cgtgaccgac
1741 ctgaaggagg tcttgggctg cctgtatgag tctcaggagg aggagctggc gaaggtggtg
1801 gtggccccgt tcaaggaaat ttctattcac ctgacaaata cttctgaagt gatgcattgt
1861 tccttcagcc tgaagcattg tcaagacttg cagaaactct cactgcaggt agcaaagggg
1921 gtgttcctgg agaattacat ggattttgaa ctggacattg aatttgaaag ctcaaacagc
1981 aacctcaagt ttctggaagt gaaacaaagc ttcctgagtg actcttctgt gcggattctt
2041 tgtgaccacg taacccgtag cacctgtcat ctgcagaaag tggagattaa aaacgtcacc
2101 cctgacaccg cgtaccggga cttctgtctt gctttcattg ggaagaagac cctcacgcac
2161 ctgaccctgg cagggcacat cgagtgggaa cgcacgatga tgctgatgct gtgtgacctg
2221 ctcagaaatc ataaatgcaa cctgcagtac ctgaggttgg gaggtcactg tgccaccccg
2281 gagcagtggg ctgaattctt ctatgtcctc aaagccaacc agtccctgaa gcacctgcgt
2341 ctctcagcca atgtgctcct ggatgagggt gccatgttgc tgtacaagac catgacacgc
2401 ccaaaacact tcctgcagat gttgtcgttg gaaaactgtc gtcttacaga agccagttgc
2461 aaggaccttg ctgctgtctt ggttgtcagc aagaagctga cacacctgtg cttggccaag
2521 aaccccattg gggatacagg ggtgaagttt ctgtgtgagg gcttgagtta ccctgattgt
2581 aaactgcaga ccttggtgtt acagcaatgc agcataacca agcttggctg tagatatctc
2641 tcagaggcgc tccaagaagc ctgcagcctc acaaacctgg acttgagtat caaccagata
2701 gctcgtggat tgtggattct ctgtcaggcg ttagagaatc caaactgtaa cctaaaacac
2761 ctacgcctct ggagctgctc cctcatgcct ttctattgtc agcatcttgg atctgctctc
2821 ctcagcaatc agaagcttga aactctggac ctgggccaga atcatttgtg gaagagtggc
2881 ataattaagc tctttggggt tctaagacaa agaactggat ccttgaagat actcaggttg
2941 aagacctatg aaactaattt ggaaatcaag aagctgttgg aggaagtgaa agaaaagaat
3001 cccaagctga ctattgattg caatgcttcc ggggcaacgg cacctccgtg ctgtgacttt
3061 ttttgctgag cagcctggga tcgctctacg aattacacag gaagcgggat tcgggtctct 3121 aagatgtctt atgaatgcag gtcagagggt cacatgttaa cactagagtc tgtcgagagg
3181 taggatttga cactggtttt ctcactattt ttgggagatt ctgcacgagt cacgcacccc
3241 cttcacatga cgctatgtac tttctcacag ggataataaa gttagagcac tctcgttgca
3301 gctgcgttta ttgacatgct caggagcaaa cctgcaataa acatggtact ctgtgcttcg
3361 tctaggagga agt

Figure 13
SEQ ID NO:7

```
   1 tgagaaactg catgtgttgg gcaagatgaa cttttctgta atcacctgcc
ccaacggtgg
  61 taccaaccaa gggcttctgc cttacctgat ggccctggat cagtatcagc
tggaggaatt
 121 caagctttgc ttggaacccc agcagctgat ggacttctgg tcggcccccc
aggggcactt
 181 cccgcgtatc ccctgggcaa acttgagagc tgccgacccct ttgaatctgt
cctttctttt
 241 ggatgaacac ttcccaaaag gtcaggcatg gaaagtggtc ctcggcatct
tccagacaat
 301 gaatctgacc tcactgtgtg agaaagttag agccgagatg aaagagaatg
tgcagaccca
 361 agagctgcaa gatccaaccc aggaagatct agagatgcta gaagcagcag
cagggaatat
 421 gcagacccag ggatgccaag atccaaacca agaagaacta gacgagctag
aagaagaaac
 481 agggaatgta caggcccagg gatgccaaga tccaaaccaa gaagaaccag
agatgctaga
 541 ggaagcagac cacagaagaa aatacagaga gaacatgaag gctgaactac
tggagacatg
 601 ggacaacatc agttggccta aagaccacgt atatatccgt aatacatcaa
aggacgaaca
 661 tgaggaactg cagcgcctac tggatcctaa taggactaga gcccaggccc
agacgatagt
 721 cttggtgggg agggcagggg ttgggaagac caccttggca atgcaggcta
tgctgcactg
 781 ggcaaatgga gttctctttc agcaaaggtt ctcctatgtt ttctatctca
gctgccataa
 841 aataaggtac atgaaggaaa ctacctttgc tgaattgatt tctttggatt
ggcccgattt
 901 tgatgccccc attgaagagt tcatgtctca accagagaag ctcctgttta
ttattgatgg
 961 ctttgaggaa ataatcatat ctgagtcacg ctctgagagc ttggatgatg
gctcgccatg
1021 tacagactgg taccaggagc tcccagtgac caaaatccta cacagcttgt
tgaagaaaga
1081 attggttccc ctggctacct tactgatcac gatcaagacc tggtttgtga
gagatcttaa
1141 ggcctcatta gtgaatccat gctttgtaca aattacaggg ttcacagggg
acgacctacg
1201 ggtatatttc atgagacact ttgatgactc aagtgaagtt gagaaaatcc
tgcagcagct
1261 aagaaaaaac gaaactctct ttcattcctg cagtgccccc atggtgtgtt
ggaccgtatg
1321 ttcctgtctg aagcagccga aggtgaggta ttacgatctc cagtcaatca
ctcagactac
1381 caccagtctg tatgcctatt ttttctccaa cttgttctcc acagcagagg
tagatttggc
```

1441 agatgacagc tggccaggac aatggagggc cctctgcagt ctggccatag aagggctgtg
1501 gtctatgaac ttcacgttta acaaagaaga cactgagatc gagggcctgg aagtgccttt
1561 cattgattct ctctacgagt tcaatattct tcaaaagatc aatgactgtg ggggttgcac
1621 tactttcacc cacctaagtt tccaggagtt ttttgcagcc atgtcctttg tgctagagga
1681 acctagagaa ttccctcccc attccacaaa gccacaagag atgaagatgt tactgcaaca
1741 cgtcttgctt gacaaagaag cctactggac tccagtggtt ctgttcttct ttggtctttt
1801 aaataaaaac atagcaagag aactggaaga tactttgcat tgtaaaatat ctcccagggt
1861 aatggaggaa ttattaaagt ggggagaaga gttaggtaag gctgaaagtg cctctctcca
1921 atttcacatt ctacgacttt ttcactgcct acacgagtcc caggaggaag acttcacaaa
1981 gaagatgttg ggtcgtatct ttgaagttga ccttaatatt ttggaggacg aagaactcca
2041 agcttcttca ttttgcctaa agcactgtaa aaggttaaat aagctaaggc tttctgttag
2101 cagtcacatc cttgaaaggg acttggaaat tctggagaca agcaagtttg attccaggat
2161 gcacgcatgg aacagcattt gctctacgtt ggtcacaaat gagaatctgc atgagctaga
2221 cctgagtaac agcaaacttc atgcttcctc tgtgaagggt ctctgtcttg cactgaaaaa
2281 tccaagatgc aaagtccaga aactgacgtg caaatcggta actcctgagt gggttctgca
2341 ggacctcatt attgcccttc agggtaacag caagctgacc catctgaact tcagctctaa
2401 caagctggga atgactgtcc ccctgattct taaagctttg agacactcag cttgcaacct
2461 caagtatctg tgcctggaga aatgcaactt gtcggcagcc agctgtcagg acctagcctt
2521 gtttctcacc agcatccaac acgtaactcg attgtgcctg ggatttaatc ggctccaaga
2581 tgatggcata aagctattgt gtgcggccct gactcacccc aagtgtgcct tagagagact
2641 ggagctctgg ttttgccagc tggcagcacc cgcttgcaag cacttgtcag atgctctcct
2701 gcagaacagg agcctgacac acctgaatct gagcaagaac agcctgagag acgagggagt
2761 caagttcctg tgtgaggcct tgggtcgccc agatggtaac ctgcagagcc tgaatttgtc
2821 aggttgttct ttcacaagag agggctgtgg agagctggct aatgccctca gccataatca
2881 taatgtgaaa atcttagatt tgggagaaaa tgatcttcag gatgatggag tgaagctact
2941 gtgtgaggct ctgaaaccac atcgtgcatt gcacacactt gggttggcga aatgcaatct
3001 gacaactgct tgctgccagc atctcttctc tgttctcagc agcagtaaga gcctggtcaa
3061 tctgaacctt ctaggcaatg aattggatac tgatggtgtc aagatgctat gcttcaaaaa 3121 gacctgcaca atgtagtgag agaggagata cagacctcac agaaggagct ctgtctgaaa
3181 ctcaagtgtg cgtgggattt taatgacctt gaagacaagt ggtggtggtg atcccacgga
3241 ttagatgcca cgtggcttga ccatggatct tgggggaaag ccaccaggac atcctggcct
3301 gtgtgtcgct ccaatgtcac catttgtggg gacaaatgag ctgttccctg caggaggctt
3361 tgtcacggtt gttggaggcc gcccattgca cgcccaggtc tggaatccta gtgtaatact
3421 gtgtctggta ccaagatcat aagttggctg tgccttcagt cttgtctatg tcctccttgg
3481 tgtaatgttt ttaattcttg gaggtgttga gagaattcaa taaagcaaag catataaaaa

Figure 14
SEQ ID NO:9

```
   1 atggcagaat cggattctac tgactttgac ctgctgtggt atctagagaa
tctcagtgac
  61 aaggaatttc agagttttaa gaagtatctg gcacgcaaga ttcttgattt
caaactgcca
 121 cagtttccac tgatacagat gacaaaagaa gaactggcta acgtgttgcc
aatctcttat
 181 gagggacagt atatatggaa tatgctcttc agcatatttt caatgatgcg
taaggaagat
 241 ctttgtagga agatcattgg cagacgaaac cgcaatcagg aggcatgcaa
agctgtcatg
 301 aggagaaaat tcatgctgca atgggaaagt cacacttttg gaaaatttca
ttataaattt
 361 tttcgtgacg tttcgtcaga tgtgttctac atacttcaat tagcctatga
ttctaccagc
 421 tattattcag caaacaatct caatgtgttc ctgatgggag agagagcatc
tggaaaaact
 481 attgttataa atctggctgt gttgaggtgg atcaagggtg agatgtggca
gaacatgatc
 541 tcgtacgtcg ttcacctcac ttctcacgaa ataaaccaga tgaccaacag
cagcttggct
 601 gagctaatcg ccaaggactg gcctgacggc caggctccca ttgcagacat
cctgtctgat
 661 cccaagaaac tccttttcat cctcgaggac ttggacaaca taagattcga
gttaaatgtc
 721 aatgaaagtg ctttgtgtag taacagcacc cagaaagttc ccattccagt
tctcctggtc
 781 agtttgctga agagaaaaat ggctccaggc tgctggttcc tcatctcctc
aaggcccaca
 841 cgtgggaata atgtaaaaac gttcttgaaa gaggtagatt gctgcacgac
cttgcagctg
 901 tcgaatggga agagggagat atattttaac tctttcttta aagaccgcca
gagggcgtcg
 961 gcagccctcc agcttgtaca tgaggatgaa atactcgtgg gtctgtgccg
agtcgccatc
1021 ttatgctgga tcacgtgtac tgtcctgaag cggcagatgg acaaggggcg
tgacttccag
1081 ctctgctgcc aaacacccac tgatctacat gcccactttc ttgctgatgc
gttgacatca
1141 gaggctggac ttactgccaa tcagtatcac ctaggtctcc taaaacgtct
gtgtttgctg
1201 gctgcaggag gactgtttct gagcaccctg aatttcagtg gtgaagacct
cagatgtgtt
1261 gggtttactg aggctgatgt ctctgtgttg caggccgcga atattctttt
gccgagcaac
1321 actcataaag accgttacaa gttcatacac ttgaacgtcc aggagttttg
tacagccatt
1381 gcatttctga tggcagtacc caactatctg atcccctcag gcagcagaga
gtataaagag
1441 aagagagaac aatactctga ctttaatcaa gtgtttactt tcatttttgg
tcttctaaat
```

1501 gcaaacagga gaaagattct tgagacatcc tttggatacc agctaccgat ggtagacagc
1561 ttcaagtggt actcggtggg atacatgaaa catttggacc gtgacccgga aaagttgacg
1621 caccatatgc ctttgtttta ctgtctctat gagaatcggg aagaagaatt tgtgaagacg
1681 attgtggatg ctctcatgga ggttacagtt taccttcaat cagacaagga tatgatggtc
1741 tcattatact gtctggatta ctgctgtcac ctgaggacac ttaagttgag cgttcagcgc
1801 atctttcaaa acaaagagcc acttataagg ccaactgcta gtcaaatgaa gagccttgtc
1861 tactggagag agatctgctc tctttttat acaatggaga gcctccggga gctgcatatc
1921 tttgacaatg accttaatgg tatttcagaa aggattctgt ctaaagccct ggagcattct
1981 agctgtaaac ttcgcacact caagttgtcc tatgtctcga ctgcttctgg ttttgaagac
2041 ttactcaagg ctttggctcg taatcggagc ctgacatacc tgagtatcaa ctgtacgtcc
2101 atttccctaa atatgttttc acttctgcat gacatcctgc acgagcccac atgccaaata
2161 agtcatctga gcttgatgaa atgtgatttg cgagccagcg aatgcgaaga aatcgcctct
2221 ctcctcatca gtggcgggag tctgagaaaa ctgaccttat ccagcaatcc gctgaggagc
2281 gacgggatga acatactgtg tgatgccttg cttcatccca actgcactct tatatcactg
2341 gtgttagtct tctgctgtct cactgaaaat tgctgcagcg cccttggaag agtgcttctg
2401 ttcagcccaa ctctaagaca actagacctg tgtgtgaatc gcttaaaaaa ttacggagtg
2461 ttgcatgtga cgtttccctt gctgtttcca acctgtcagt tagaggagct tcatctgtct
2521 ggctgtttct ttagcagcga tatctgtcaa tatattgcca tagttattgc tactaatgaa
2581 aaactgagga gcctggagat tgggagcaac aaaatagaag atgcaggaat gcagctgcta
2641 tgtggtggtt tgagacatcc caactgcatg ttggtgaata ttgggctaga agagtgcatg
2701 ttaaccagtg cctgctgtcg atctcttgcc tctgttctta ccaccaacaa aacactagaa
2761 agactcaact tgcttcaaaa tcacttgggc aatgatggag ttgcaaaact tcttgagagc
2821 ttgatcagcc cagattgtgt acttaaggta gttgggcttc cattaactgg cctgaacaca
2881 caaacccagc agttgctgat gactgtaaag gaaagaaaac ccagtttgat ctttctgtct
2941 gaaacttggt ctttaaagga aggcagagaa attggtgtga cacctgcttc tcagccaggt
3001 tcaataatac ctaattctaa tttggattac atgtttttca aatttcccag aatgtctgca
3061 gccatgagaa cgtcaaatac agcatctagg caacccctttt ga

Figure 15
SEQ ID NO:10

ATGAGGTGGGGCCACCATTTGCCCAGGGCCTCTTGGGGCTCTGGTTTTAGAAGAGCACT
CCAGCGACCAGATGATCGTATCCCCTTCCTGATCCACTGGAGTTGGCCCCTTCAAGGGG
AGCGTCCCTTTGGGCCCCCTAGGGCCTTTATACGCCACCACGGAAGCTCGGTAGATAGC
GCTCCCCCACCCGGGAGGCATGGACGGCTGTTCCCCAGCGCCTCTGCAACTGAAGCTAT
ACAGCGGCACCGCCGGAACCTGGCTGAGTGGTTCAGCCGGCTGCCCAGGGAGGAGCGCC
AGTTTGGCCCAACCTTTGCCCTAGACACGGTCCACGTTGACCCTGTGATCCGCGAGAGT
ACCCCTGATGAGCTACTTCGCCCACCCGCGGAGCTGGCCCTGGAGCATCAGCCACCCCA
GGCCGGGCTCCCCCCACTGGCCTTGTCTCAGCTCTTTAACCCGGATGCCTGTGGGCGCC
GGGTGCAGACAGTGGTGCTGTATGGGACAGTGGGCACAGGCAAGAGCACGCTGGTGCGC
AAGATGGTTCTGGACTGGTGTTATGGGCGGCTGCCGGCCTTCGAGCTGCTCATCCCCTT
CTCCTGTGAGGACCTGTCATCCCTGGGCCCTGCCCCAGCCTCCCTGTGCCAACTTGTGG
CCCAGCGCTACACGCCCCTGAAGGAGGTTCTGCCCCTGATGGCTGCTGCTGGGTCCCAC
CTCCTCTTTGTGCTCCATGGCTTAGAGCATCTCAACCTCGACTTCCGGCTGGCAGGCAC
GGGACTTTGTAGTGACCCGGAGGAACCGCAGGAACCAGCTGCTATCATCGTCAACCTGC
TGCGCAAATACATGCTGCCTCAGGCCAGCATTCTGGTGACCACTCGGCCCTCTGCCATT
GGCCGTATCCCCAGCAAGTACGTGGGCCGCTATGGTGAGATCTGCGGTTTCTCTGATAC
CAACCTGCAGAAGCTCTACTTCCAGCTCCGCCTCAACCAGCCGTACTGCGGGTATGCCG
TTGGCGGTTCAGGTGTCTCTGCCACACCAGCTCAGCGTGACCACCTGGTGCAGATGCTC
TCCCGGAACCTGGAGGGGCACCACCAGATAGCCGCTGCCTGCTTCCTGCCGTCCTATTG
CTGGCTCGTTTGTGCCACCTTGCACTTCCTGCATGCCCCCACGCCTGCTGGGCAGACCC
TTACAAGCATCTATACCAGCTTCCTGCGCCTCAACTTCAGCGGGGAAACCCTGGACAGC
ACTGACCCCTCCAATTTGTCCCTGATGGCCTATGCAGCCCGAACCATGGGCAAGTTGGC
CTATGAGGGGGTGTCCTCCCGCAAGACCTACTTCTCTGAAGAGGATGTCTGTGGCTGCC
TGGAGGCTGGCATCAGGACGGAGGAGGAGTTTCAGCTGCTGCACATCTTCCGTCGGGAT
GCCCTGAGGTTTTTCCTGGCCCCATGTGTGGAGCCAGGGCGTGCAGGCACCTTCGTGTT
CACCGTGCCCGCCATGCAGGAATACCTGGCTGCCCTCTACATTGTGCTGGGTTTGCGCA
AGACGACCCTGCAAAAGGTGGGCAAGGAAGTGGCTGAGCTCGTGGGCCGTGTTGGGGAG
GACGTCAGCCTGGTACTGGGCATCATGGCCAAGCTGCTGCCTCTGCGGGCTCTGCCTCT
GCTCTTCAACCTGATCAAGGTGGTTCCACGAGTGTTTGGGCGCATGGTGGGTAAAAGCC
GGGAGGCGGTGGCTCAGGCCATGGTGCTGGAGATGTTTCGAGAGGAGGACTACTACAAC
GATGATGTTCTGGACCAGATGGGCGCCAGTATCCTGGGCGTGGAGGGCCCCCGGCGCCA
CCCAGATGAGCCCCCTGAGGATGAAGTCTTCGAGCTCTTCCCCATGTTCATGGGGGGGC
TTCTCTCTGCCCACAACCGAGCTGTGCTAGCTCAGCTTGGCTGCCCCATCAAGAACCTG
GATGCCCTGGAGAATGCCCAGGCCATCAAGAAGAAGCTGGGCAAGCTGGGCCGGCAGGT
GCTGCCCCCATCAGAGCTCCTTGACCACCTCTTCTTCCACTATGAGTTCCAGAACCAGC
GCTTCTCCGCTGAGGTGCTCAGCTCCCTGCGTCAGCTCAACCTGGCAGGTGTGCGCATG
ACACCAGTCAAGTGCACAGTGGTGGCAGCTGTGCTGGGCAGCGGAAGGCATGCCCTGGA
TGAGGTGAACTTGGCCTCCTGCCAGCTAGATCCTGCTGGGCTGCGCACACTCCTGCCTG
TCTTCCTGCGTGCCCGGAAGCTGGGCTTGCAACTCAACAGCCTGGGCCCTGAGGCCTGC
AAGGACCTCCGAGACCTGTTGCTGCATGACCAGTGCCAAATTACCACACTGCGGCTGTC
CAACAACCCGCTGACGGCGGCAGGTGTTGCCGTGCTAATGGAGGGGCTGGCAGGAAACA

CCTCAGTGACGCACCTGTCCCTGCTGCACACGGGCCTTGGGGACGAAGGCCTGGAGCTG
CTGGCTGCCCAGCTGGACCGCAACCGGCAGCTGCAGGAGCTGAACGTGGCGTACAACGG
TGCTGGTGACACAGCGGCCCTGGCCCTGGCCAGAGCTGCCCGGGAGCACCCTTCCCTGG
AACTGCTACACCTCTACTTCAATGAGCTGAGCTCAGAGGGCCGCCAGGTCTTGCGAGAC
TTGGGGGGTGCTGCTGAAGGTGGTGCCCGGGTGGTGGTGTCACTGACAGAGGGGACGGC
GGTGTCAGAATACTGGTCAGTGATCCTCAGTGAAGTCCAGCGGAACCTCAATAGCTGGG
ATCGGGCCCGGGTTCAGCGACACCTTGAGCTCCTACTGCGGGATCTGGAAGATAGCCGG
GGTGCCACCCTTAATCCTTGGCGCAAGGCCCAGCTGCTGCGAGTGGAGGGCGAGGTCAG
GGCCCTCCTGGAGCAGCTGGGAAGCTCTGGAAGCTGA

Figure 16
SEQ ID NO:11 ggaggagccgcgagcgctgagggtgagtgccgggagctctgagggagtctgcactatgg
aaacaacctgtcaatccagctcaaggcacacatagcccagacacccatgagaccctctc
cgtggggaccctagagcacctatcatgaacgaggagaccaaggctggctcctcATGGAC
CCCGTTGGCCTCCAGCTCGGCAACAAGAACCTGTGGAGCTGTCTTGTGAGGCTGCTCAC
CAAAGACCCAGAATGGCTGAACGCCAAGATGAAGTTCTTCCTCCCCAACACGGACCTGG
ATTCCAGGAACGAGACCTTGGACCCTGAACAGAGAGTCATCCTGCAACTCAACAAGCTG
CATGTCCAGGGTTCGGACACCTGGCAGTCTTTCATTCATTGCGTGTGCATGCAGCTGGA
GGTGCCTCTGGACCTGGAGGTGCTTCTGCTAAGTACTTTTGGCTATGATGATGGGTTCA
CCAGCCAGCTGGGAGCTGAGGGGAAAAGCCAACCTGAATCTCAGCTCCACCATGGCCTG
AAGCGCCCACATCAGAGCTGTGGGTCCTCACCCCGCCGGAAGCAGTGCAAGAAGCAGCA
GCTAGAGTTGGCCAAGAAGTACCTGCAGCTCCTGCGGACCTCTGCCCAGCAGCGCTACA
GGAGCCAAATCCCTGGGTCAGGGCAGCCCCACGCCTTCCACCAGGTCTATGTCCCTCCA
ATCCTGCGCCGGGCCACAGCATCCTTAGACACTCCGGAGGGGGCCATTATGGGGGACGT
CAAGGTGGAAGATGGTGCTGACGTGAGCATCTCGGACCTCTTCAACACCAGGGTTAACA
AGGGCCCGAGGGTGACCGTGCTTTTGGGGAAGGCTGGCATGGGCAAGACCACGCTGGCC
CACCGGCTCTGCCAGAAGTGGGCAGAGGGCCATCTGAACTGTTTCCAGGCCCTGTTCCT
TTTTGAATTCCGCCAGCTCAACTTGATCACGAGGTTCCTGACACCGTCCGAGCTCCTTT
TTGATCTGTACCTGAGCCCTGAATCGGACCACGACACTGTCTTCCAGTACCTGGAGAAG
AACGCTGACCAAGTCCTGCTGATCTTTGATGGGCTAGATGAGGCCCTCCAGCCTATGGG
TCCTGATGGCCCAGGCCCAGTCCTCACCCTTTTCTCCCATCTCTGCAATGGGACCCTCC
TGCCTGGCTGCCGGGTGATGGCTACCTCCCGTCCAGGGAAGCTGCCTGCCTGCCTGCCT
GCAGAGGCAGCCATGGTCCACATGTTGGGCTTTGATGGGCCACGGGTGGAAGAATATGT
GAATCACTTCTTCAGCGCCCAGCCATCGCGGGAGGGGGCCCTGGTGGAGTTACAGACAA
ATGGACGTCTCCGAAGCCTGTGTGCGGTGCCCGCACTGTGCCAAGTCGCCTGTCTCTGC
CTCCACCATCTGCTTCCTGACCACGCCCCAGGCCAGTCTGTGGCCCTCCTGCCCAACAT
GACTCAGCTCTATATGCAGATGGTGCTCGCCCTCAGCCCCCCTGGGCACTTGCCCACCT
CGTCCCTACTGGACCTGGGGGAGGTGGCCCTGAGGGGCCTGGAGACAGGGAAGGTTATC
TTCTATGCAAAAGATATTGCTCCACCCTTGATAGCTTTTGGGGCCACTCACAGCCTGCT
GACTTCCTTCTGCGTCTGCACAGGCCCTGGGCACCAGCAGACAGGCTATGCTTTCACCC
ACCTCAGCCTGCAGGAGTTTCTTGCTGCCCTGCACCTGATGGCCAGCCCCAAGGTGAAC
AAAGACACACTTACCCAGTATGTTACCCTCCATTCCCGCTGGGTACAGCGGACCAAAGC
TAGACTGGGCCTCTCAGACCACCTCCCCACCTTCCTGGCGGGCCTGGCATCCTGCACCT
GCCGCCCCTTCCTTAGCCACCTGGCGCAGGGCAATGAGGACTGTGTGGGTGCCAAGCAG
GCTGCTGTAGTGCAGGTGTTGAAGAAGTTGGCCACCCGCAAGCTCACAGGGCCAAAGGT
TGTAGAGCTGTGTCACTGTGTGGATGAGACACAGGAGCCTGAGCTGGCCAGTCTCACCG
CACAAAGCCTCCCCTATCAACTGCCCTTCCACAATTTCCCACTGACCTGCACCGACCTG
GCCACCCTGACCAACATCCTAGAGCACAGGGAGGCCCCCATCCACCTGGATTTTGATGG
CTGTCCCCTGGAGCCCCACTGCCCTGAGGCTCTGGTAGGCTGTGGGCAGATAGAGAATC
TCAGCTTTAAGAGCAGGAAGTGTGGGGATGCCTTTGCAGAAGCCCTCTCCAGGAGCTTG
CCGACAATGGGGAGGCTGCAGATGCTGGGGTTAGCAGGAAGTAAAATCACTGCCCGAGG
CATCAGCCACCTGGTGAAAGCTTTGCCTCTCTGTCCACAGCTGAAAGAAGTCAGTTTTC
GGGACAACCAGCTCAGTGACCAGGTGGTGCTGAACATTGTGGAGGTTCTCCCTCACCTA CCACGGCTCCGGAAGCTTGACCTGAGCAGCAACAGCATCTGCGTGTCAACCCTACTCTG
CTTGGCAAGGGTGGCAGTCACGTGTCCTACCGTCAGGATGCTTCAGGCCAGGGAGCGGA
CCATCATCTTCCTTCTTTCCCCGCCCACAGAGACAACTGCAGAGCTACAAAGAGCTCCA
GACCTGCAGGAAAGTGACGGCCAGAGGAAAGGGGCTCAGAGCAGAAGCTTGACGCTCAG
GCTGCAGAAGTGTCAGCTCCAGGTCCACGATGCGGAGGCCCTCATAGCCCTGCTCCAGG
AAGGCCCTCACCTGGAGGAAGTGGACCTCTCAGGGAACCAGCTGGAAGATGAAGGCTGT
CGGCTGATGGCAGAGGCTGCATCCCAGCTGCACATCGCCAGGAAGCTGGACCTCAGCGA
CAACGGGCTTTCTGTGGCCGGGGTGCATTGTGTGCTGAGGGCCGTGAGTGCGTGCTGGA
CCCTGGCAGAGCTGCACATCAGCCTGCAGCACAAAACTGTGATCTTCATGTTTGCCCAG
GAGCCAGAGGAGCAGAAGGGGCCCCAGGAGAGGGCTGCATTTCTTGACAGCCTCATGCT
CCAGATGCCCTCTGAGCTGCCTCTGAGCTCCCGAAGGATGAGGCTGACACATTGTGGCC
TCCAAGAAAAGCACCTAGAGCAGCTCTGCAAGGCTCTGGGAGGAAGCTGCCACCTCGGT
CACCTCCACCTCGACTTCTCAGGCAATGCTCTGGGGGATGAAGGTGCAGCCCGGCTGGC
TCAGCTGCTCCCAGGGCTGGGAGCTCTGCAGTCCTTGAACCTCAGTGAGAACGGTTTGT
CCCTGGATGCCGTGTTGGGCTTGGTTCGGTGCTTCTCCACTCTGCAGTGGCTCTTCCGC
TTGGACATCAGCTTTGAAAGCCAACACATCCTCCTGAGAGGGGACAAGACAAGCAGGGA
TATGTGGGCCACTGGATCTTTGCCAGACTTCCCAGCTGCAGCCAAGTTCTTAGGGTTCC
GTCAGCGCTGCATCCCCAGGAGCCTCTGCCTCAGTGAGTGTCCTCTGGAGCCCCCAAGC
CTCACCCGCCTCTGTGCCACTCTGAAGGACTGCCCGGGACCCCTGGAACTGCAATTGTC
CTGTGAGTTCCTGAGTGACCAGAGCCTGGAGACTCTACTGGACTGCTTACCTCAACTCC
CTCAGCTGAGCCTGCTGCAGCTGAGCCAGACGGGACTGTCCCCGAAAAGCCCCTTCCTG
CTGGCCAACACCTTAAGCCTGTGTCCACGGGTTAAAAAGGTGGATCTCAGGTCCCTGCA
CCATGCAACTTTGCACTTCAGATCCAACGAGGAGGAGGAAGGCGTGTGCTGTGGCAGGT
TCACAGGCTGCAGCCTCAGCCAGGAGCACGTAGAGTCACTCTGCTGGTTGCTGAGCAAG
TGTAAAGACCTCAGCCAGGTGGATCTCTCAGCAAACCTGCTGGGCGACAGCGGACTCAG
ATGCCTTCTGGAATGTCTGCCGCAGGTGCCCATCTCCGGTTTGCTTGATCTGAGTCACA
ACAGCATTTCTCAGGAAAGTGCCCTGTACCTGCTGGAGACACTGCCCTCCTGCCCACGT
GTCCGGGAGGCCTCAGTGAACCTGGGCTCTGAGCAGAGCTTCCGGATTCACTTCTCCAG
AGAGGACCAGGCTGGGAAGACACTCAGGCTAAGTGAGTGCAGCTTCCGGCCAGAGCACG
TGTCCAGGCTGGCCACCGGCTTGAGCAAGTCCCTGCAGCTGACGGAGCTCACGCTGACC
CAGTGCTGCCTGGGCCAGAAGCAGCTGGCCATCCTCCTGAGCTTGGTGGGGCGACCCGC
AGGGCTGTTCAGCCTCAGGGTGCAGGAGCCGTGGGCGGACAGAGCCAGGGTTCTCTCCC
TGTTAGAAGTCTGCGCCCAGGCCTCAGGCAGTGTCACTGAAATCAGCATCTCCGAGACC
CAGCAGCAGCTCTGTGTCCAGCTGGAATTTCCTCGCCAGGAAGAGAATCCAGAAGCTGT
GGCACTCAGGTTGGCTCACTGTGACCTTGGAGCCCACCACAGCCTTCTTGTCGGGCAGC
TGATGGAGACATGTGCCAGGCTGCAGCAGCTCAGCTTGTCTCAGGTTAACCTCTGTGAG
GACGATGATGCCAGTTCCCTGCTGCTGCAGAGCCTCCTGCTGTCCCTCTCTGAGCTGAA
GACATTTCGGCTGACCTCCAGCTGTGTGAGCACCGAGGGCCTCGCCCACCTGGCATCTG
GTCTGGGCCACTGCCACCACTTGGAGGAGCTGGACTTGTCTAACAATCAATTTGATGAG
GAGGGCACCAAGGCGCTGATGAGGGCCCTTGAGGGGAAATGGATGCTAAAGAGGCTGGA
CCTCAGTCACCTTCTGCTGAACAGCTCCACCTTGGCCTTGCTTACTCACAGACTAAGCC
AGATGACCTGCCTGCAGAGCCTCAGACTGAACAGGAACAGTATCGGTGATGTCGGTTGC
TGCCACCTTTCTGAGGCTCTCAGGGCTGCCACCAGCCTAGAGGAGCTGGACTTGAGCCA
CAACCAGATTGGAGACGCTGGTGTCCAGCACTTAGCTACCATCCTGCCTGGGCTGCCAG
AGCTCAGGAAGATAGACCTCTCAGGGAATAGCATCAGCTCAGCCGGGGGAGTGCAGTTG
GCAGAGTCTCTCGTTCTTTGCAGGCGCCTGGAGGAGTTGATGCTTGGCTGCAATGCCCT
GGGGGATCCCACAGCCCTGGGGCTGGCTCAGGAGCTGCCCCAGCACCTGAGGGTCCTAC ACCTACCATTCAGCCATCTGGGCCCAGGTGGGGCCCTGAGCCTGGCCCAGGCCCTGGAT
GGATCCCCCCATTTGGAAGAGATCAGCTTGGCGGAAAACAACCTGGCTGGAGGGGTCCT
GCGTTTCTGTATGGAGCTCCCGCTGCTCAGACAGATAGACCTGGTTTCCTGTAAGATTG
ACAACCAGACTGCCAAGCTCCTCACCTCCAGCTTCACGAGCTGCCCTGCCCTGGAAGTA
ATCTTGCTGTCCTGGAATCTCCTCGGGGATGAGGCAGCTGCCGAGCTGGCCCAGGTGCT
GCCGAAGATGGGCCGGCTGAAGAGAGTGGACCTGGAGAAGAATCAGATCACAGCTTTGG
GGGCCTGGCTCCTGGCTGAAGGACTGGCCCAGGGGTCTAGCATCCAAGTCATCCGCCTC
TGGAATAACCCCATTCCCTGCGACATGGCCCAGCACCTGAAGAGCCAGGAGCCCAGGCT
GGACTTTGCCTTCTTTGACAACCAGCCCCAGGCCCCTTGGGGTACTTGAtggccccctc
aagacctttggaatccagccaagtgatgcacccaaatgatccacctttcgcccactggg
ataaatgactcaggaaagaagagcctcggcagggcgctctgcactccacccaggaggaa
ggatacgtgtgtcctgctgcagtcctcagggagaactttttgggaaccaggagctggg
tctggacaaaggagtaccctgcattacgtgggatatgtgtgatcaattggggacatgcg
acacacaatgagggtgtcatgacaatgcatgacacgtacggttatatgtggcagtgtga
ccccttgacatgtggcgttacatgaaagtcagtgtggcacgtgttctgtggcatgggtg
ctggcatcccaagtggcaggatacatgattgttggtctatatatgacacatgacaaatg
tccatgtcacaggactcatggctggccagatgacctcaggctggcccaagatctaattt
attaattttaaagcaaatacatatttatagattgtgtgtatggagcagctaagtcagg
aaaagtcttccgcccgagctgggaggggagagtgtccatgcactgaccagtccaggggc
tcaagggccagggctctggaacaagccagggactcagccattaagtcccctcctgcctc
aatcctcagcctacccatctataaacttgatgactcctcccttacttacatactagctt
ccaaggacaggtggaggtagggccagcctggcgggagtggagaagcccagtctgtccta
tgtaagggacaaagccaggtctaatggtactgggtagggggcactgccaagacaataag
ctaggctactgggtccagctactactttggtgggattcaggtgagtctccatgcacttc
acatgttacccagtgttcttgttacttccaaggagaaccaagaatggctctgtcacact
cgaagccaggtttgatcaataaacacaatggtattcc

Figure 17
SEQ ID NO:12

MEMDAPRPPSLAVPGAASRPGRLLDGGHGRQQVQALSSQLLEVIPDSMRKQEVRTGREA
GQGHGTGSPAEQVKALMDLLAGKGSQGSHAPQALDRTPDAPLGPCSNDSRIQRHRKALL
SKVGGGPELGGPWHRLASLLLVEGLTDLQLREHDFTQVEATRGGGHPARTVALDRLFLP
LSRVSVPPRVSITIGVAGMGKTTLVRHFVRLWAHGQVGKDFSLVLPLTFRDLNTHEKLC
ADRLICSVFPHVGEPSLAVAVPARALLILDGLDECRTPLDFSNTVACTDPKKEIPVDHL
ITNIIRGNLFPEVSIWITSRPSASGQIPGGLVDRMTEIRGFNEEEIKVCLEQMFPEDQA
LLGWMLSQVQADRALYLMCTVPAFCRLTGMALGHLWRSRTGPQDAELWPPRTLCELYSW
YFRMALSGEGQEKGKASPRIEQVAHGGRKMVGTLGRLAFHGLLKKKYVFYEQDMKAFGV
DLALLQGAPCSCFLQREETLASSVAYCFTHLSLQEFVAAAYYYGASRRAIFDLFTESGV
SWPRLGFLTHFRSAAQRAMQAEDGRLDVFLRFLSGLLSPRVNALLAGSLLAQGEHQAYR
TQVAELLQGCLRPDAAVCARAINVLHCLHELQHTELARSVEEAMESGALARLTGPAHRA
ALAYLLQVSDACAQEANLSLSLSQGVLQSLLPQLLYCRKLRLDTNQFQDPVMELLGSVL
SGKDCRIQKISLAENQISNKGAKALARSLLVNRSLTSLDLRGNSIGPQGAKALADALKI
NRTLTSLSLQGNTVRDDGARSMAEALASNRTLSMLHLQKNSIGPMGAQRMADALKQNRS
LKELMFSSNSIGDGGAKALAEALKVNQGLESLDLQSNSISDAGVAALMGALCTNQTLLS
LSLRENSISPEGAQAIAHALCANSTLKNLDLTANLLHDQGARAIAVAVRENRTLTSLHL
QWNFIQAGAAQALGQALQLNRSLTSLDLQENAIGDDGACAVARALKVNTALTALYLQVA
SIGASGAQVLGEALAVNRTLEILDLRGNAIGVAGAKALANALKVNSSLRRLNLQENSLG
MDGAICIATALSGNHRLQHINLQGNHIGDSGARMISEAIKTNAPTCTVEM

Figure 18
SEQ ID NO:13

MADSSSSSFFPDFGLLLYLEELNKEELNTFKLFLKETMEPEHGLTPWNEVKKARREDLA
NLMKKYYPGEKAWSVSLKIFGKMNLKDLCERAKEEINWSAQTIGPDDAKAGETQEDQEA
VLGDGTEYRNRIKEKFCITWDKKSLAGKPEDFHHGIAEKDRKLLEHLFDVDVKTGAQPQ
IVVLQGAAGVGKTTLVRKAMLDWAEGSLYQQRFKYVFYLNGREINQLKERSFAQLISKD
WPSTEGPIEEIMYQPSSLLFIIDSFDELNFAFEEPEFALCEDWTQEHPVSFLMSSLLRK
VMLPEASLLVTTRLTTSKRLKQLLKNHHYVELLGMSEDAREEYIYQFFEDKRWAMKVFS
SLKSNEMLFSMCQVPLVCWAACTCLKQQMEKGGDVTLTCQTTTALFTCYISSLFTPVDG
GSPSLPNQAQLRRLCQVAAKGIWTMTYVFYRENLRRLGLTQSDVSSFMDSNIIQKDAEY
ENCYVFTHLHVQEFFAAMFYMLKGSWEAGNPSCQPFEDLKSLLQSTSYKDPHLTQMKCF
LFGLLNEDRVKQLERTFNCKMSLKIKSKLLQCMEVLGNSDYSPSQLGFLELFHCLYETQ
DKAFISQAMRCFPKVAINICEKIHLLVSSFCLKHCRCLRTIRLSVTVVFEKKILKTSLP
TNTWDGDRITHCWQDLCSVLHTNEHLRELDLYHSNLDKSAMNILHHELRHPNCKLQKLL
LKFITFPDGCQDISTSLIHNKNLMHLDLKGSDIGDNGVKSLCEALKHPECKLQTLRLES
CNLTVFCCLNISNALIRSQSLIFLNLSTNNLLDDGVQLLCEALRHPKCYLERLSLESCG
LTEAGCEYLSLALISNKRLTHLCLADNVLGDGGVKLMSDALQHAQCTLKSLVLRRCHFT
SLSSEYLSTSLLHNKSLTHLDLGSNWLQDNGVKLLCDVFRHPSCNLQDLELMGCVLTNA
CCLDLASVILNNPNLRSLDLGNNDLQDDGVKILCDALRYPNCNIQRLGLEYCGLTSLCC
QDLSSALICNKRLIKMNLTQNTLGYEGIVKLYKVLKSPKCKLQVLGLCKEAFDEEAQKL
LEAVGVSNPHLIIKPDCNYHNEEDVSWWWCF

Figure 19
SEQ ID NO:14

MAESFFSDFGLLWYLKELRKEEFWKFKELLKQPLEKFELKPIPWAELKKASKEDVAKLL
DKHYPGKQAWEVTLNLFLQINRKDLWTKAQEEMRNKLNPYRKHMKETFQLIWEKETCLH
VPEHFYKETMKNEYKELNDAYTAAARRHTVVLEGPDGIGKTTLLRKVMLDWAEGNLWKD
RFTFVFFLNVCEMNGIAETSLLELLSRDWPESSEKIEDIFSQPERILFIMDGFEQLKFN
LQLKADLSDDWRQRQPMPIILSSLLQKKMLPESSLLIALGKLAMQKHYFMLRHPKLIKL
LGFSESEKKSYFSYFFGEKSKALKVFNFVRDNGPLFILCHNPFTCWLVCTCVKQRLERG
EDLEINSQNTTYLYASFLTTVFKAGSQSFPPKVNRARLKSLCALAAEGIWTYTFVFSHG
DLRRNGLSESEGVMWVGMRLLQRRGDCFAFMHLCIQEFCAAMFYLLKRPKDDPNPAIGS
ITQLVRASVVQPQTLLTQVGIFMFGISTEEIVSMLETSFGFPLSKDLKQEITQCLESLS
QCEADREAIAFQELFIGLFETQEKEFVTKVMNFFEEVFIYIGNIEHLVIASFCLKHCQH
LTTLRMCVENIFPDDSGCISDYNEKLVYWRELCSMFITNKNFQILDMENTSLDDPSLAI
LCKALAQPVCKLRKLIFTSVYFGHDSELFKAVLHNPHLKLLSLYGTSLSQSDIRHLCET
LKHPMCKIEELILGKCDISSEVCEDIASVLACNSKLKHLSLVENPLRDEGMTLLCEALK
HSHCALERLMLMYCCLTSVSCDSISEVLLCSKSLSLLDLGSNALEDNGVASLCAALKHP
GCSIRELWLMGCFLTSDSCKDIAAVLICNGKLKTLKLGHNEIGDTGVRQLCAALQHPHC
KLECLGLQTCPITRACCDDIAAALIACKTLRSLNLDWIALDADAVVVLCEALSHPDCAL
QMLGLHKSGFDEETQKILMSVEEKIPHLTISHGPWIDEEYKIRGVLL

Figure 20
SEQ ID NO:15

MAMAKARKPREALLWALSDLEENDFKKLKFYLRDMTLSEGQPPLARGELEGLIPVDLAE
LLISKYGEKEAVKVVLKGLKVMNLLELVDQLSHICLHDYREVYREHVRCLEEWQEAGVN
GRYNQVLLVAKPSSESPESLACPFPEQELESVTVEALFDSGEKPSLAPSLVVLQGSAGT
GKTTLARKMVLDWATGTLYPGRFDYVFYVSCKEVVLLLESKLEQLLFWCCGDNQAPVTE
ILRQPERLLFILDGFDELQRPFEEKLKKRGLSPKESLLHLLIRRHTLPTCSLLITTRPL
ALRNLEPLLKQARHVHILGFSEEERARYFSSYFTDEKQADRAFDIVQKNDILYKACQVP
GICWVVCSWLQGQMERGKVVLETPRNSTDIFMAYVSTFLPPDDDGGCSELSRHRVLRSL
CSLAAEGIQHQRFLFEEAELRKHNLDGPRLAAFLSSNDYQLGLAIKKFYSFRHISFQDF
FHAMSYLVKEDQSRLGKESRREVQRLLEVKEQEGNDEMTLTMQFLLDISKKDSFSNLEL
KFCFRISPCLAQDLKHFKEQMESMKHNRTWDLEFSLYEAKIKNLVKGIQMNNVSFKIKH
SNEKKSQSQNLFSVKSSLSHGPKEEQKCPSVHGQKEGKDNIAGTQKEASTGKGRGTEET
PKNTYI

Figure 21
SEQ ID NO:16

MRWGHHLPRASWGSGFRRALQRPDDRIPFLIHWSWPLQGERPFGPPRAFIRHHGSSVDS
APPSGRHGRLFPSASATEAIQRHRRNLAEWFSRLPREERQFGPTFALDTVHVDPVIRES
TPDELLRPPAELALEHQPPQAGLPPLALSQLFNPDACGRRVQTVVLYGTVGTGKSTLVR
KMVLDWCYGRLPAFELLIPFSCEDLSSLGPAPASLCQLVAQRYTPLKEVLPLMAAAGSH
LLFVLHGLEHLNLDFRLAGTGLCSDPEEPQEPAAIIVNLLRKYMLPQASILVTTRPSAI
GRIPSKYVGRYGEICGFSDTNLQKLYFQLRLNQPYCGYAVGGSGVSATPAQRDHLVQML
SRNLEGHHQIAAACFLPSYCWLVCATLHFLHAPTPAGQTLTSIYTSFLRLNFSGETLDS
TDPSNLSLMAYAARTMGKLAYEGVSSRKTYFSEEDVCGCLEAGIRTEEEFQLLHIFRRD
ALRFFLAPCVEPGRAGTFVFTVPAMQEYLAALYIVLGLRKTTLQKVGKEVAELVGRVGE
DVSLVLGIMAKLLPLRALPLLFNLIKVVPRVFGRMVGKSREAVAQAMVLEMFREEDYYN
DDVLDQMGASILGVEGPRRHPDEPPEDEVFELFPMFMGGLLSAHNRAVLAQLGCPIKNL
DALENAQAIKKKLGKLGRQVLPPSELLDHLFFHYEFQNQRFSAEVLSSLRQLNLAGVRM
TPVKCTVVAAVLGSGRHALDEVNLASCQLDPAGLRTLLPVFLRARKLGLQLNSLGPEAC
KDLRDLLLHDQCQITTLRLSNNPLTEAGVAVLMEGLAGNTSVTHLSLLHTGLGDEGLEL
LAAQLDRNRQLQELNVAYNGAGDTAALALARAAREHPSLELLHLYFNELSSEGRQVLRD
LGGAAEGGARVVVSLTEGTAVSEYWSVILSEVQRNLNSWDRARVQRHLELLLRDLEDSR
GATLNPWRKAQLLRVEGEVRALLEQLGSSGS

Figure 22
SEQ ID NO:17

MTSPQLEWTLQTLLEQLNEDELKSFKSLLWAFPLEDVLQKTPWSEVEEADGEKLAEILV
NTSSENWIRNATVNILEEMNLTELCKMAKAEMMEDGQVQEIDNPELGDAEEDSELAKPG
EKEGWRNSMEKQSLVWKNTFWQGDIDNFHDDVTLRNQRFIPFLNPRTPRKLTPYTVVLH
GPAGVGKTTLAKKCMLDWTDCNLSPTLRYAFYLSCKELSRMGPCSFAELISKDWPELQD
DIPSILAQAQRILFVVDGLDELKVPPGALIQDICGDWEKKKPVPVLLGSLLKRKMLPRA
ALLVTTRPRALRDLQLLAQQPIYVRVEGFLEEDRRAYFLRHFGDEDQAMRAFELMRSNA
ALFQLGSAPAVCWIVCTTLKLQMEKGEDPVPTCLTRTGLFLRFLCSRFPQGAQLRGALR
TLSLLAAQGLWAQMSVFHREDLERLGVQESDLRLFLDGDILRQDRVSKGCYSFIHLSFQ
QFLTALFYALEKEEGEDRDGHAWDIGDVQKLLSGEERLKNPDLIQVGHFLFGLANEKRA
KELEATFGCRMSPDIKQELLQCKAHLHANKPLSVTDLKEVLGCLYESQEEELAKVVVAP
FKEISIHLTNTSEVMHCSFSLKHCQDLQKLSLQVAKGVFLENYMDFELDIEFESSNSNL
KFLEVKQSFLSDSSVRILCDHVTRSTCHLQKVEIKNVTPDTAYRDFCLAFIGKKTLTHL
TLAGHIEWERTMMLMLCDLLRNHKCNLQYLRLGGHCATPEQWAEFFYVLKANQSLKHLR
LSANVLLDEGAMLLYKTMTRPKHFLQMLSLENCRLTEASCKDLAAVLVVSKKLTHLCLA
KNPIGDTGVKFLCEGLSYPDCKLQTLVLQQCSITKLGCRYLSEALQEACSLTNLDLSIN
QIARGLWILCQALENPNCNLKHLRLWSCSLMPFYCQHLGSALLSNQKLETLDLGQNHLW
KSGIIKLFGVLRQRTGSLKILRLKTYETNLEIKKLLEEVKEKNPKLTIDCNASGATAPP
CCDFFC

Figure 23
SEQ ID NO:18

MNFSVITCPNGGTNQGLLPYLMALDQYQLEEFKLCLEPQQLMDFWSAPQGHFPRIPWAN
LRAADPLNLSFLLDEHFPKGQAWKVVLGIFQTMNLTSLCEKVRAEMKENVQTQELQDPT
QEDLEMLEAAAGNMQTQGCQDPNQEELDELEEETGNVQAQGCQDPNQEEPEMLEEADHR
RKYRENMKAELLETWDNISWPKDHVYIRNTSKDEHEELQRLLDPNRTRAQAQTIVLVGR
AGVGKTTLAMQAMLHWANGVLFQQRFSYVFYLSCHKIRYMKETTFAELISLDWPDFDAP
IEEFMSQPEKLLFIIDGFEEIIISESRSESLDDGSPCTDWYQELPVTKILHSLLKKELV
PLATLLITIKTWFVRDLKASLVNPCFVQITGFTGDDLRVYFMRHFDDSSEVEKILQQLR
KNETLFHSCSAPMVCWTVCSCLKQPKVRYYDLQSITQTTTSLYAYFFSNLFSTAEVDLA
DDSWPGQWRALCSLAIEGLWSMNFTFNKEDTEIEGLEVPFIDSLYEFNILQKINDCGGC
TTFTHLSFQEFFAAMSFVLEEPREFPPHSTKPQEMKMLLQHVLLDKEAYWTPVVLFFFG
LLNKNIARELEDTLHCKISPRVMEELLKWGEELGKAESASLQFHILRLFHCLHESQEED
FTKKMLGRIFEVDLNILEDEELQASSFCLKHCKRLNKLRLSVSSHILERDLEILETSKF
DSRMHAWNSICSTLVTNENLHELDLSNSKLHASSVKGLCLALKNPRCKVQKLTCKSVTP
EWVLQDLIIALQGNSKLTHLNFSSNKLGMTVPLILKALRHSACNLKYLCLEKCNLSAAS
CQDLALFLTSIQHVTRLCLGFNRLQDDGIKLLCAALTHPKCALERLELWFCQLAAPACK
HLSDALLQNRSLTHLNLSKNSLRDEGVKFLCEALGRPDGNLQSLNLSGCSFTREGCGEL
ANALSHNHNVKILDLGENDLQDDGVKLLCEALKPHRALHTLGLAKCNLTTACCQHLFSV
LSSSKSLVNLNLLGNELDTDGVKMLCFKKTCTM

Figure 24
SEQ ID NO:20

MAESDSTDFDLLWYLENLSDKEFQSFKKYLARKILDFKLPQFPLIQMTKEELANVLPIS
YEGQYIWNMLFSIFSMMRKEDLCRKIIGRRNRNQEACKAVMRRKFMLQWESHTFGKFHY
KFFRDVSSDVFYILQLAYDSTSYYSANNLNVFLMGERASGKTIVINLAVLRWIKGEMWQ
NMISYVVHLTSHEINQMTNSSLAELIAKDWPDGQAPIADILSDPKKLLFILEDLDNIRF
ELNVNESALCSNSTQKVPIPVLLVSLLKRKMAPGCWFLISSRPTRGNNVKTFLKEVDCC
TTLQLSNGKREIYFNSFFKDRQRASAALQLVHEDEILVGLCRVAILCWITCTVLKRQMD
KGRDFQLCCQTPTDLHAHFLADALTSEAGLTANQYHLGLLKRLCLLAAGGLFLSTLNFS
GEDLRCVGFTEADVSVLQAANILLPSNTHKDRYKFIHLNVQEFCTAIAFLMAVPNYLIP
SGSREYKEKREQYSDFNQVFTFIFGLLNANRRKILETSFGYQLPMVDSFKWYSVGYMKH
LDRDPEKLTHHMPLFYCLYENREEEFVKTIVDALMEVTVYLQSDKDMMVSLYCLDYCCH
LRTLKLSVQRIFQNKEPLIRPTASQMKSLVYWREICSLFYTMESLRELHIFDNDLNGIS
ERILSKALEHSSCKLRTLKLSYVSTASGFEDLLKALARNRSLTYLSINCTSISLNMFSL
LHDILHEPTCQISHLSLMKCDLRASECEEIASLLISGGSLRKLTLSSNPLRSDGMNILC
DALLHPNCTLISLVLVFCCLTENCCSALGRVLLFSPTLRQLDLCVNRLKNYGVLHVTFP
LLFPTCQLEELHLSGCFFSSDICQYIAIVIATNEKLRSLEIGSNKIEDAGMQLLCGGLR
HPNCMLVNIGLEECMLTSACCRSLASVLTTNKTLERLNLLQNHLGNDGVAKLLESLISP
DCVLKVVGLPLTGLNTQTQQLLMTVKERKPSLIFLSETWSLKEGREIGVTPASQPGSII
PNSNLDYMFFKFPRMSAAMRTSNTASRQPL

Figure 25
SEQ ID NO:21

MRWGHHLPRASWGSGFRRALQRPDDRIPFLIHWSWPLQGERPFGPPRAFIRHHGSSVDS
APPPGRHGRLFPSASATEAIQRHRRNLAEWFSRLPREERQFGPTFALDTVHVDPVIRES
TPDELLRPPAELALEHQPPQAGLPPLALSQLFNPDACGRRVQTVVLYGTVGTGKSTLVR
KMVLDWCYGRLPAFELLIPFSCEDLSSLGPAPASLCQLVAQRYTPLKEVLPLMAAAGSH
LLFVLHGLEHLNLDFRLAGTGLCSDPEEPQEPAAIIVNLLRKYMLPQASILVTTRPSAI
GRIPSKYVGRYGEICGFSDTNLQKLYFQLRLNQPYCGYAVGGSGVSATPAQRDHLVQML
SRNLEGHHQIAAACFLPSYCWLVCATLHFLHAPTPAGQTLTSIYTSFLRLNFSGETLDS
TDPSNLSLMAYAARTMGKLAYEGVSSRKTYFSEEDVCGCLEAGIRTEEEFQLLHIFRRD
ALRFFLAPCVEPGRAGTFVFTVPAMQEYLAALYIVLGLRKTTLQKVGKEVAELVGRVGE
DVSLVLGIMAKLLPLRALPLLFNLIKVVPRVFGRMVGKSREAVAQAMVLEMFREEDYYN
DDVLDQMGASILGVEGPRRHPDEPPEDEVFELFPMFMGGLLSAHNRAVLAQLGCPIKNL
DALENAQAIKKKLGKLGRQVLPPSELLDHLFFHYEFQNQRFSAEVLSSLRQLNLAGVRM
TPVKCTVVAAVLGSGRHALDEVNLASCQLDPAGLRTLLPVFLRARKLGLQLNSLGPEAC
KDLRDLLLHDQCQITTLRLSNNPLTAAGVAVLMEGLAGNTSVTHLSLLHTGLGDEGLEL
LAAQLDRNRQLQELNVAYNGAGDTAALALARAAREHPSLELLHLYFNELSSEGRQVLRD
LGGAAEGGARVVVSLTEGTAVSEYWSVILSEVQRNLNSWDRARVQRHLELLLRDLEDSR
GATLNPWRKAQLLRVEGEVRALLEQLGSSGS

Figure 26
SEQ ID NO:22

MDPVGLQLGNKNLWSCLVRLLTKDPEWLNAKMKFFLPNTDLDSRNETLDPEQRVILQLN
KLHVQGSDTWQSFIHCVCMQLEVPLDLEVLLLSTFGYDDGFTSQLGAEGKSQPESQLHH
GLKRPHQSCGSSPRRKQCKKQQLELAKKYLQLLRTSAQQRYRSQIPGSGQPHAFHQVYV
PPILRRATASLDTPEGAIMGDVKVEDGADVSISDLFNTRVNKGPRVTVLLGKAGMGKTT
LAHRLCQKWAEGHLNCFQALFLFEFRQLNLITRFLTPSELLFDLYLSPESDHDTVFQYL
EKNADQVLLIFDGLDEALQPMGPDGPGPVLTLFSHLCNGTLLPGCRVMATSRPGKLPAC
LPAEAAMVHMLGFDGPRVEEYVNHFFSAQPSREGALVELQTNGRLRSLCAVPALCQVAC
LCLHHLLPDHAPGQSVALLPNMTQLYMQMVLALSPPGHLPTSSLLDLGEVALRGLETGK
VIFYAKDIAPPLIAFGATHSLLTSFCVCTGPGHQQTGYAFTHLSLQEFLAALHLMASPK
VNKDTLTQYVTLHSRWVQRTKARLGLSDHLPTFLAGLASCTCRPFLSHLAQGNEDCVGA
KQAAVVQVLKKLATRKLTGPKVVELCHCVDETQEPELASLTAQSLPYQLPFHNFPLTCT
DLATLTNILEHREAPIHLDFDGCPLEPHCPEALVGCGQIENLSFKSRKCGDAFAEALSR
SLPTMGRLQMLGLAGSKITARGISHLVKALPLCPQLKEVSFRDNQLSDQVVLNIVEVLP
HLPRLRKLDLSSNSICVSTLLCLARVAVTCPTVRMLQARERTIIFLLSPPTETTAELQR
APDLQESDGQRKGAQSRSLTLRLQKCQLQVHDAEALIALLQEGPHLEEVDLSGNQLEDE
GCRLMAEAASQLHIARKLDLSDNGLSVAGVHCVLRAVSACWTLAELHISLQHKTVIFMF
AQEPEEQKGPQERAAFLDSLMLQMPSELPLSSRRMRLTHCGLQEKHLEQLCKALGGSCH
LGHLHLDFSGNALGDEGAARLAQLLPGLGALQSLNLSENGLSLDAVLGLVRCFSTLQWL
FRLDISFESQHILLRGDKTSRDMWATGSLPDFPAAAKFLGFRQRCIPRSLCLSECPLEP
PSLTRLCATLKDCPGPLELQLSCEFLSDQSLETLLDCLPQLPQLSLLQLSQTGLSPKSP
FLLANTLSLCPRVKKVDLRSLHHATLHFRSNEEEEGVCCGRFTGCSLSQEHVESLCWLL
SKCKDLSQVDLSANLLGDSGLRCLLECLPQVPISGLLDLSHNSISQESALYLLETLPSC
PRVREASVNLGSEQSFRIHFSREDQAGKTLRLSECSFRPEHVSRLATGLSKSLQLTELT
LTQCCLGQKQLAILLSLVGRPAGLFSLRVQEPWADRARVLSLLEVCAQASGSVTEISIS
ETQQQLCVQLEFPRQEENPEAVALRLAHCDLGAHHSLLVGQLMETCARLQQLSLSQVNL
CEDDDASSLLLQSLLLSLSELKTFRLTSSCVSTEGLAHLASGLGHCHHLEELDLSNNQF
DEEGTKALMRALEGKWMLKRLDLSHLLLNSSTLALLTHRLSQMTCLQSLRLNRNSIGDV
GCCHLSEALRAATSLEELDLSHNQIGDAGVQHLATILPGLPELRKIDLSGNSISSAGGV
QLAESLVLCRRLEELMLGCNALGDPTALGLAQELPQHLRVLHLPFSHLGPGGALSLAQA
LDGSPHLEEISLAENNLAGGVLRFCMELPLLRQIDLVSCKIDNQTAKLLTSSFTSCPAL
EVILLSWNLLGDEAAAELAQVLPKMGRLKRVDLEKNQITALGAWLLAEGLAQGSSIQVI
RLWNNPIPCDMAQHLKSQEPRLDFAFFDNQPQAPWGT

Figure 27
SEQ ID NO:8

```
1 gtctcgtgtt tctctcttcc aatcggttgt ctttatcgtg gacactgagg
tgttctctgc
61 cttgactaaa gatgagtgac gtgaatccac cctctgacac ccccattccc
ttttcatcct
121 cctccactca cagttctcat attccgccct ggacattctc ttgctacccc
ggctccccat
181 gtgaaaatgg ggtcatgctg tacatgagaa acgtgagcca tgaggagcta
caacggttca
241 agcagctctt actgactgag ctcagtactg gcaccatgcc catcacctgg
gaccaggtcg
301 agacagccag ctgggcagag gtggttcatc tcttgataga gcgtttccct
ggacgacgcg
361 cttgggatgt gacttcgaac atctttgcca ttatgaactg tgataaaatg
tgtgttgtag
421 tccgcagaga gataaatgcc attctgccta ccttggaacc agaggacttg
aatgtgggag
481 aaacacaggt gaatctggag gaaggagaat ctggtaaaat acggcggtat
aaatcgaatg
541 tgatggaaaa gtttttcccc atatgggaca ttacgacttg gcctggaaac
cagagggact
601 tcttctacca aggtgtacac aggcacgagg agtacttacc atgtctgctt
ctgcccaaaa
661 gaccccaggg tagacagccc aagaccgtgg ccatacaggg agctcctggg
atcggaaaaa
721 caatcctggc caaaaaggtg atgtttgagt gggccagaaa caagttctac
gcccacaagc
781 gctggtgtgc tttctacttc cattgccaag aggtgaacca gacgacagac
cagagcttct
841 ccgagctgat tgagcaaaag tggcctggat ctcaggacct cgtgtcaaag
attatgtcca
901 aacccgacca acttctgctg ctcttggatg gctttgagga gctcacatct
accctcattg
961 acagactgga ggacctgagt gaagactgga ggcagaaatt gcctgggtct
gtcctactga
1021 gcagtttgct gagcaaaacg atgcttccag aggccacgct actgatcatg
ataagattta
1081 cctcttggca gacatgcaag cccttgctga aatgtccctc tctcgtaacc
cttccggggt
1141 ttaatacgat ggaaaaaatc aagtatttcc agatgtattt tggacacaca
gaggagggag
1201 accaagtctt gagtttcgcc atggaaaaca ccattctctt ctccatgtgc
cgggtccctg
1261 tggtttgctg gatggtctgc tctggtctga aacagcaaat ggagagagga
aacaatctca
1321 cacagtcatg tccaaatgcc acctctgtgt tcgtccggta tatttctagc
ttgtttccca
1381 ccagagctga gaacttttcc agaaagatcc accaagcaca actggaaggt
ctgtgtcact
1441 tggccgcaga cagcatgtgg cacaggaaat gggtgttagg taaagaagat
cttgaggaag
```

1501 ccaagctgga tcagacggga gtcaccgcct tccttggcat gagtattctt cggagaattg
1561 caggtgagga agaccactat gtctttaccc tcgtgacttt tcaggaattt tttgcggcct
1621 tgttttatgt tctctgtttc ccacaaagac tcaaaaattt tcatgtgttg agccacgtga
1681 atatccagcg cctgatagcg agtcccagag gaagcaaaag ctatctctct cacatgggac
1741 ttttcttatt cggttttctg aacgaggcct gcgcttcggc cgtggaacag tcattccaat
1801 gcaaggtgtc tttcggtaat aagaggaaac tgctgaaagt catacctctg ttgcataaat
1861 gtgacccacc ttctccgggc agtggggtcc cgcagttatt ctactgtctg catgaaatcc
1921 gggaggaagc ctttgtaagc caagccctaa atgattatca taaagttgtc ttgagaattg
1981 gcaacaacaa agaagttcaa gtgtctgctt tttgcctgaa gcggtgtcaa tatttgcatg
2041 aggtggaact gaccgtcacc ctgaacttca tgaacgtgtg gaagctcagc tccagctccc
2101 atcctggctc tgaagcgcca gagagcaatg ggctgcatcg ttggtggcaa gacttatgct
2161 ctgtgtttgc aacgaatgat aagctggaag tcctgactat gaccaacagt gttttggggc
2221 ctcctttttt gaaggctctc gcggccgcac tgaggcaccc tcagtgcaaa ctgcaaaagc
2281 tactcctaag gcgtgtgaat agcaccatgt tgaaccagga cttaatcggt gttttgacgg
2341 ggaaccagca tctgagatac ttggaaatac aacatgtgga agtggagtcc aaagctgtga
2401 agcttctatg cagggtgctg agatcccccc ggtgccgtct gcagtgtctc aggttggaag
2461 actgcttggc caccccctaga atttggactg atcttggcaa taatcttcaa ggtaacgggc
2521 atctaaagac tctcatacta agaaaaaact ccctggagaa ctgtggggcg tattacctgt
2581 ctgtggccca gctggagagg ctgtcgatag agaactgcaa ccttacacag cttacttgtg
2641 aaagccttgc ctcctgtctc aggcagagta agatgctgac ccacctgagc ttggcagaaa
2701 acgccttgaa agatgaaggg gccaagcata tttggaatgc cctgccacac ctgagatgtc
2761 ctctgcagag gctggtactg agaaagtgtg acttgacctt taattgctgt caggatatga
2821 tctctgcgct ctgtaaaaat aaaaccctga aaagtcttga cctaagtttt aatagcctga
2881 aggatgatgg ggtgatcctg ctgtgtgagg ccctgaagaa ccctgactgt acattacaga
2941 tcctggagct ggaaaactgc ctgttcacct ccatctgctg ccaggccatg gcttccatgc
3001 tccgcaaaaa ccaacatctg agacatctgg acttgagcaa gaatgcgatt ggagtctatg
3061 gtattctgac cttgtgcgag gccttctcaa gccaaaagaa gagagaagag gtcattttct
3121 gtattcctgc ctggactcga ataactagct tctccccaac tcctcaccca cccgacttca 3181 cgggaaaaag tgactgccta tcccagatta atccttaggc cgtccagtca tctttctctg
3241 gggcttgatt gatcagttcc cactctgaca actggcaaat accaggcgtt atcatcctgt
3301 atgcattaac gtactttccc ctgaaacaga gcaacccagt caacaccaca gaacctcagc
3361 tttgaacccct ggagtgagga cggtgatgcc ctgtgtgtat taatatgcta tgtaaggctg
3421 ggcgtggtgg ctcacgcctg taacccagca ctatgggagg tcgaggtggg cagattacct
3481 gaggtcagga gttccagacc agcctggcca acatggtgaa accccgcctc tactaaaaaa
3541 aaaaatacaa aaaattaggc gtggtggtgg gctcctgtaa tcccagctgc tcgggaggct
3601 gaggcaggag aatcacttga atctaggagg cagagtttgc agtgagctga gatcacgcca
3661 ttgcactcca gcctgggcga cagagcaaga ctctgtctca agaagaaaaa aaaaatacat
3721 atacacataa atatatatat gtgtgtgtgt atatatatat atatatatat atatgctata
3781 taaagtttaa atgaaatgct ttgagtcacc taagacagga tatagacaaa gtcttcatcg
3841 tcttcttgct tcttctacct ttatttattc tcagctctga atgtatgaac ctgctcaatc
3901 acctcatctt aaaaataaaa tcactgtccc taga

Figure 28
SEQ ID NO:19

MSDVNPPSDTPIPFSSSSTHSSHIPPWTFSCYPGSPCENGVMLYMRNVSHEELQRFKQLLLTELSTGTMPI
TWDQVETASWAEVVHLLIERFPGRRAWDVTSNIFAIMNCDKMCVVVRREINAILPTLEPEDLNVGETQVNL
EEGESGKIRRYKSNVMEKFFPIWDITTWPGNQRDFFYQGVHRHEEYLPCLLLPKRPQGRQPKTVAIQGAPG
IGKTILAKKVMFEWARNKFYAHKRWCAFYFHCQEVNQTTDQSFSELIEQKWPGSQDLVSKIMSKPDQLLLL
LDGFEELTSTLIDRLEDLSEDWRQKLPGSVLLSSLLSKTMLPEATLLIMIRFTSWQTCKPLLKCPSLVTLP
GFNTMEKIKYFQMYFGHTEEGDQVLSFAMENTILFSMCRVPVVCWMVCSGLKQQMERGNNLTQSCPNATSV
FVRYISSLFPTRAENFSRKIHQAQLEGLCHLAADSMWHRKWVLGKEDLEEAKLDQTGVTAFLGMSILRRIA
GEEDHYVFTLVTFQEFFAALFYVLCFPQRLKNFHVLSHVNIQRLIASPRGSKSYLSHMGLFLFGFLNEACA
SAVEQSFQCKVSFGNKRKLLKVIPLLHKCDPPSPGSGVPQLFYCLHEIREEAFVSQALNDYHKVVLRIGNN
KEVQVSAFCLKRCQYLHEVELTVTLNFMNVWKLSSSSHPGSEAPESNGLHRWWQDLCSVFATNDKLEVLTM
TNSVLGPPFLKALAAALRHPQCKLQKLLLRRVNSTMLNQDLIGVLTGNQHLRYLEIQHVEVESKAVKLLCR
VLRSPRCRLQCLRLEDCLATPRIWTDLGNNLQGNGHLKTLILRKNSLENCGAYYLSVAQLERLSIENCNLT
QLTCESLASCLRQSKMLTHLSLAENALKDEGAKHIWNALPHLRCPLQRLVLRKCDLTFNCCQDMISALCKN
KTLKSLDLSFNSLKDDGVILLCEALKNPDCTLQILELENCLFTSICCQAMASMLRKNQHLRHLDLSKNAIG
VYGILTLCEAFSSQKKREEVIFCIPAWTRITSFSPTPHPPDFTGKSDCLSQINP

NOD NUCLEIC ACIDS AND POLYPEPTIDES

This application claims priority to provisional patent application Ser. No. 60/452,274, filed Mar. 5, 2003, which is herein incorporated by reference in its entirety.

This invention was made with government support under Grants No. DK61707 and GM60421 awarded by the National Institutes of Health. The Government has certain rights in the invention.

FIELD OF THE INVENTION

The present invention relates to the NOD proteins and nucleic acids encoding the NOD proteins. The present invention further provides assays for the detection of NOD polymorphisms and mutations associated with disease states, as well as methods of screening for ligands and modulators of NOD proteins.

BACKGROUND OF THE INVENTION

The removal of infectious agents by the host is fundamental for the survival of multicellular organisms. In animals and plants, the initial detection of microbial agents relies on specialized host receptors that recognize molecules expressed exclusively by microbes (Dang and Jones, *Nature* 411, 826–833 (2001); Medzhitov, *Nature Rev. Immunol.* 1, 135–145 (2001)). In animals, detection of microbial agents is mediated by the recognition of pathogen-associated molecular patterns (PAMPs) by specific host pattern-recognition receptors (PRRs) (Medzhitov, supra). Because the structure of each PAMP is highly conserved and invariant in microorganisms of the same class, the animal can recognize most or all microbes with a limited number of PRRs. The identification and characterization of plasma membrane Toll-like receptors (TLRs) as PRRs have provided fundamental insight into the mechanisms of host defense in animals. There is now compelling evidence that TLRs play a pivotal role in mediating immune responses to bacterial pathogens (Medzhitov, supra; Akira et al., *Nat. Immunol.* 2, 675–680 (2001)) In mammals, TLRs mediate host immune responses by inducing the secretion of several proinflammatory cytokines and co-stimulatory surface molecules through the activation of transcriptional factors including NF-κB (Medzhitov, supra; Akira et al., supra). The cellular response induced through TLR signaling mediates non-specific pathogen resistance as well as specific adaptive immunity, which leads to the removal of the invading pathogen. Other organisms, including nematodes and plants, have also developed unique strategies for the removal of microbial pathogens. For example, both nematodes and plants induce a suicide program in the infected cell that is important for pathogen removal (Aballay and Ausubel, *Proc. Natl. Acad. Sci. U. S. A.* 98, 2735–2739 (2001)). In the nematode, the suicide program is dependent on CED-4 and CED-3, which are also required for the elimination of damaged and unwanted cells (Liu and Hengartner, *Ann N Y Acad Sci.* 887, 92–104 (1999); Derry et al., *Science* 294, 591–595 (2001)). In plants, recognition of pathogens is mediated by disease resistance (R) genes that encode predicted membrane-bound and cytosolic proteins (Dang and Jones, supra). R proteins mediate the hypersensitivity response, which includes localized cell death at sites of pathogen invasion (Dang and Jones, supra).

Plants recognize distinct effector molecules from pathogenic bacteria through the cytosolic R proteins (Dang and Jones, supra). By contrast, most PRRs described in animals so far, including TLRs, recognize PAMPs in extracellular compartments or at the cell surface (Medzhitov, supra). Little is known about how the host cell can sense and respond to bacteria and other infectious microorganisms within the cell. Perhaps the best characterized system for intracellular recognition of pathogens is that mediated by double-stranded RNA (dsRNA), a PAMP produced by many viruses during their infection cycle (Williams, *Oncogene* 18, 6112–6120 (1999); Nanduri et al., *EMBO J.* 19, 5567–5574 (2000)). In response to viral infection, dsRNA activates PKR, a protein kinase that mediates a transcriptional host response against the virus (Nanduri et al., supra; Williams, supra). Experimental evidence for bacterial recognition in intracellular host compartments in animal cells is scarce. Nonetheless, recent studies in mammalian systems have revealed the presence of surveillance mechanisms to sense and respond to bacteria in the cytosol (Philpott et al., *J. Immunol.* 165, 903–914 (2000); O'Riordan et al., *Proc. Natl. Acad. Sci. U S A* 99, 13861–13866 (2002)). However, the host factors and signaling pathways involved in such recognition are still poorly understood and they are just beginning to emerge. Additional information on pathogen recognition and its relation to disease such as inflammatory disease are needed.

SUMMARY OF THE INVENTION

The present invention relates to the NOD proteins and nucleic acids encoding the NOD proteins. The present invention further provides assays for the detection of NOD polymorphisms and mutations associated with disease states, as well as methods of screening for ligands and modulators of NOD proteins.

Accordingly, in some embodiments, the present invention provides a composition comprising an isolated and purified nucleic acid sequence encoding a protein selected from the group consisting of SEQ ID NOs: 12–22. In some embodiments, the sequence is operably linked to a heterologous promoter. In some embodiments, the sequence is contained within a vector. In some embodiments, the vector is within a host cell. In some embodiments, the nucleic acid comprises one of SEQ ID NOs: 1 and variants thereof that are at least 80%, preferably at least 90%, and even more preferably at least 95% identical to SEQ ID NOs: 12–22. In some embodiments, the nucleic acid comprises one of SEQ ID NOs: 1–11.

The present invention further provides a composition comprising a polypeptide having an amino acid sequence comprising SEQ ID NOs: 12–22 or variants thereof that are at least 80% identical to SEQ ID NOs: 12–22. In some embodiments, the polypeptide is at least 90%, and preferably at least 95% identical to SEQ ID NOs: 12–22. In some embodiments, the polypeptide comprises one of SEQ ID NOs: 12–22.

The present invention additionally provides a method of generating an inflammation profile, comprising providing a sample from a subject, wherein the sample comprises nucleic acid; and detecting the presence or absence of expression of at least two NOD genes in the sample, thereby generating an inflammation profile. In some embodiments, the detecting comprises detecting the presence or absence of expression of at least 5, and preferably at least 10 NOD genes in said sample. In some embodiments, the nucleic acid comprises genomic DNA. In other embodiments, the nucleic acid comprises mRNA.

DESCRIPTION OF THE FIGURES

FIG. 1 shows the domain structures of exemplary NOD nucleic acids and proteins of some embodiments of the present invention. CARD, caspase-recruitment domain; DC, dendritic cell; DT, DEFCAP/TUCAN expanded homology domain; EBD, effector-binding domain; NOD, nucleotide-binding oligomerization domain; PYD, pyrin domain; LRR, leucine-rich repeat; WD40R, WD40 repeat; BIR, baculoviral inhibitor-of-apoptosis repeat; TIR, Toll/interleukin-1 receptor.

FIG. 6 shows Table 2.

FIG. 7 shows the nucleic acid sequence of NOD3 (SEQ ID NO:1).

FIG. 8 shows the nucleic acid sequence of NOD5 (SEQ ID NO:2).

FIG. 9 shows the nucleic acid sequence of NOD6 (SEQ ID NO:3).

FIG. 10 shows the nucleic acid sequence of NOD8 (SEQ ID NO:4).

FIG. 11 shows the nucleic acid sequence of NOD9 (SEQ ID NO:5).

FIG. 12 shows the nucleic acid sequence of NOD12 (SEQ ID NO:6).

FIG. 13 shows the nucleic acid sequence of NOD14 (SEQ ID NO:7).

FIG. 14 shows the nucleic acid sequence of NOD17 (SEQ ID NO:9).

FIG. 15 shows the nucleic acid sequence of NOD26 (SEQ ID NO:10).

FIG. 16 shows the nucleic acid sequence of NOD27 (SEQ ID NO:11).

FIG. 17 shows the amino acid sequence of NOD3 (SEQ ID NO:12).

FIG. 18 shows the amino acid sequence of NOD5 (SEQ ID NO:13).

FIG. 19 shows the amino acid sequence of NOD6 (SEQ ID NO:14).

FIG. 20 shows the amino acid sequence of NOD8 (SEQ ID NO:15).

FIG. 21 shows the amino acid sequence of NOD9 (SEQ ID NO:16).

FIG. 22 shows the amino acid sequence of NOD12 (SEQ ID NO:17).

FIG. 23 shows the amino acid sequence of NOD14 (SEQ ID NO:18).

FIG. 24 shows the amino acid sequence of NOD17 (SEQ ID NO:20).

FIG. 25 shows the amino acid sequence of NOD26 (SEQ ID NO:21).

FIG. 26 shows the amino acid sequence of NOD27 (SEQ ID NO:22).

FIG. 27 shows the nucleic acid sequence of NOD16 (SEQ ID NO:8).

FIG. 28 shows the nucleic acid sequence of NOD16 (SEQ ID NO:19).

DEFINITIONS

Figure 2:
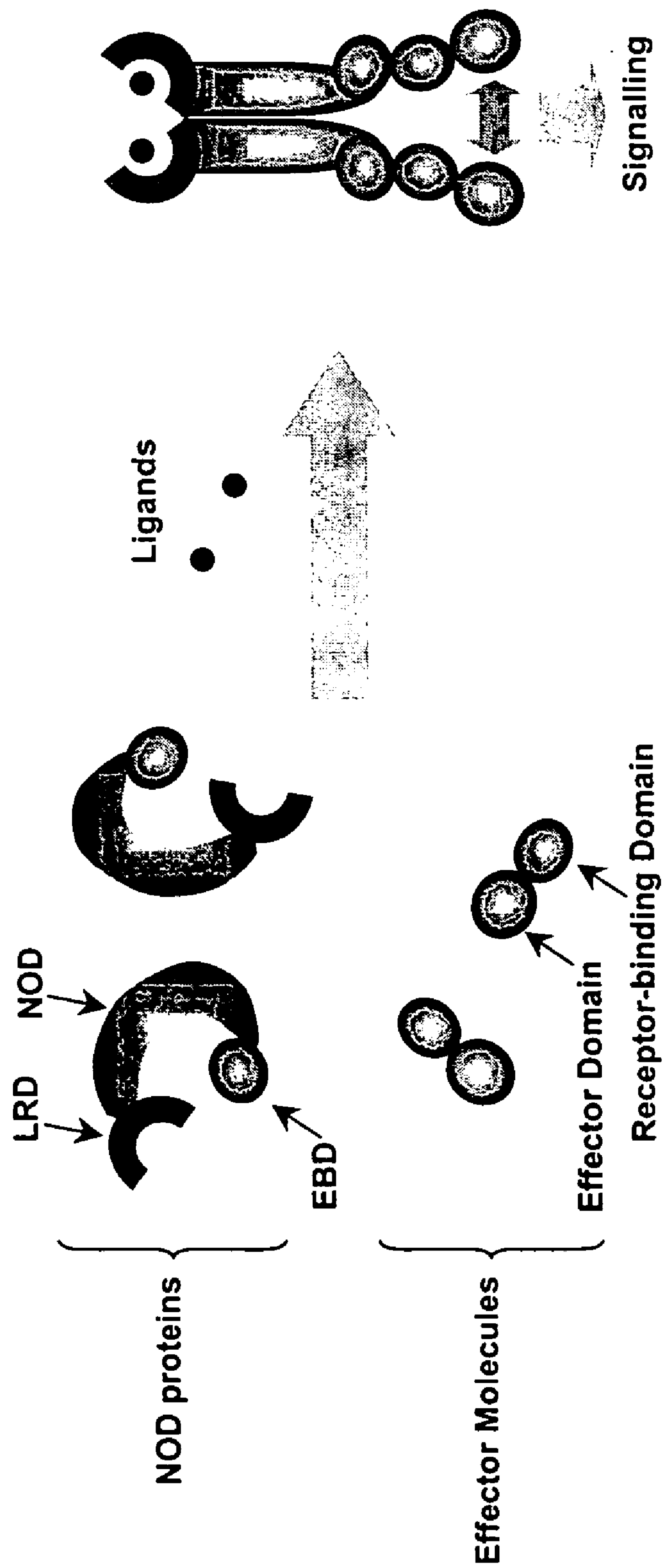
FIG. 2 shows an induced proximity model of NOD protein activation. EBD, effector binding domain; LRD, ligand recognition domain; NOD, Nucleotide-binding oligomerization domain.

To facilitate understanding of the invention, a number of terms are defined below.

As used herein, the term “NOD” when used in reference to a protein or nucleic acid refers to a NOD protein or nucleic acid encoding a NOD protein of the present invention. The term NOD encompasses both proteins that are identical to wild-type NODs and those that are derived from wild type NOD (e.g., variants of NOD polypeptides of the present invention) or chimeric genes constructed with portions of NOD coding regions). In some embodiments, the “NOD” is a wild type NOD nucleic acid (SEQ ID NOs: 1–11) or amino acid (SEQ ID NOs:12–22) sequence. In other embodiments, the “NOD” is a variant or mutant.

As used herein, the term “instructions for using said kit for said detecting the presence or absence of a variant NOD nucleic acid or polypeptide in said biological sample” includes instructions for using the reagents contained in the kit for the detection of variant and wild type NOD nucleic acids or polypeptides. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

As used herein, the term “inflammation profile” refers to the pattern of expression of two or more NOD genes of the present invention (e.g., the NOD genes described by SEQ ID NOs: 1–11). In some embodiments, the pattern of expression comprises the presence or absence of expression. In other embodiments, the pattern of expression comprises the level of expression or localization of expression of the NOD genes. The inflammation profiles of the present invention find use the characterization of inflammatory diseases and in determining a subject's risk of contacting an inflammatory disease. For example, in some embodiments, inflammation profiles from a subject are compared to control profiles associated with disease or predisposition to disease.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., NOD). The polypeptide, RNA, or precursor can be encoded by a fill length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "NOD gene" or "NOD genes" refers to the full-length NOD nucleotide sequence (e.g., contained in SEQ ID NOs: 1–11). However, it is also intended that the term encompass fragments of the NOD sequences, mutants of the NOD sequences, as well as other domains within the full-length NOD nucleotide sequences. Furthermore, the terms "NOD nucleotide sequence" or "NOD polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-"A-G-T-3'," is complementary to the sequence 3'-"T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Complementarity can include the formation of base pairs between any type of nucleotides, including non-natural bases, modified bases, synthetic bases and the like.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, *in Nucleic Acid Hybridization [*1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

The present invention is not limited to the hybridization of probes of about 500 nucleotides in length. The present invention contemplates the use of probes between approximately 10 nucleotides up to several thousand (e.g., at least 5000) nucleotides in length. One skilled in the relevant understands that stringency conditions may be altered for probes of other sizes (See e.g., Anderson and Young, Quantitative Filter Hybridization, *in Nucleic Acid Hybridization [*1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A.*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., NOD).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term “fragment” as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term “polymorphic locus” is a locus present in a population that shows variation between members of the population (i.e., the most common allele has a frequency of less than 0.95). In contrast, a “monomorphic locus” is a genetic locus at little or no variations seen between members of the population (generally taken to be a locus at which the most common allele exceeds a frequency of 0.95 in the gene pool of the population).

As used herein, the term “genetic variation information” or “genetic variant information” refers to the presence or absence of one or more variant nucleic acid sequences (e.g., polymorphism or mutations) in a given allele of a particular gene (e.g., a NOD gene of the present invention).

As used herein, the term “detection assay” refers to an assay for detecting the presence or absence of variant nucleic acid sequences (e.g., polymorphisms or mutations) in a given allele of a particular gene (e.g., a NOD gene). Examples of suitable detection assays include, but are not limited to, those described below in Section III B.

The term “naturally-occurring” as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

“Amplification” is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of “target” specificity. Target sequences are “targets” in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term “amplifiable nucleic acid” is used in reference to nucleic acids that may be amplified by any amplification method. It is contemplated that “amplifiable nucleic acid” will usually comprise “sample template.”

As used herein, the term “sample template” refers to nucleic acid originating from a sample that is analyzed for the presence of “target” (defined below). In contrast, “background template” is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term “primer” refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term “probe” refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any “reporter molecule,” so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term “target,” refers to a nucleic acid sequence or structure to be detected or characterized. Thus, the “target” is sought to be sorted out from other nucleic acid sequences. A “segment” is defined as a region of nucleic acid within the target sequence.

As used herein, the term “polymerase chain reaction” (“PCR”) refers to the method of K. B. Mullis U.S. Pat. Nos.

4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (–) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding NOD includes, by way of example, such nucleic acid in cells ordinarily expressing NOD where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, NOD antibodies are purified by removal of contaminating non-immunoglobulin proteins; they are also purified by the removal of immunoglobulin that does not bind a NOD polypeptide. The removal of non-immunoglobulin proteins and/or the removal of immunoglobulins that do not bind a NOD polypeptide results in an increase in the percent of NOD-reactive immunoglobulins in the sample. In another example, recombinant NOD polypeptides are expressed in bacterial host cells and the polypeptides are purified by the removal of host cell proteins; the percent of recombinant NOD polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein, is used to indicate a protein that does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39–7.52 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced NOD transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding NODs (e.g., SEQ ID NOs:1–11) or fragments thereof may be employed as hybridization probes. In this case, the NOD encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "entering" as in "entering said genetic variation information into said computer" refers to transferring information to a "computer readable medium." Information may be transferred by any suitable method, including but not limited to, manually (e.g., by typing into a computer) or automated (e.g., transferred from another "computer readable medium" via a "processor").

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "computer implemented method" refers to a method utilizing a "CPU" and "computer readable medium."

GENERAL DESCRIPTION OF THE INVENTION

The nucleotide-binding oligomerization domain (NOD) was first found in Apaf-1 and its nematode homologue CED-4, two pivotal regulators of developmental and p53-dependent programmed cell death (Lui and Hengartner, supra; Derry et al., supra). Subsequently, two NOD-containing molecules, NOD1 (CARD4) and NOD2, were identified through database searches for Apaf-1/CED-4 homologues. Since then, the NOD protein family has greatly expanded and currently contains a large number of proteins from animals, plants, fungi and bacteria, including>20 human proteins homologous to Apaf-1 and NOD1 (FIG. 1). The majority of NOD family members are comprised of three distinct functional domains, an amino-terminal effector binding domain (EBD), a centrally located NOD and a carboxy-terminal ligand recognition domain (LRD) (Table 2). The NOD mediates self oligomerization, which, in some embodiments, function in the activation of downstream effector molecules. The EBD of mammalian NOD proteins mediates the binding to effector molecules which determines the downstream events activated upon signaling, including apoptosis and NF-κB activation (Table 2).

Figure 3:
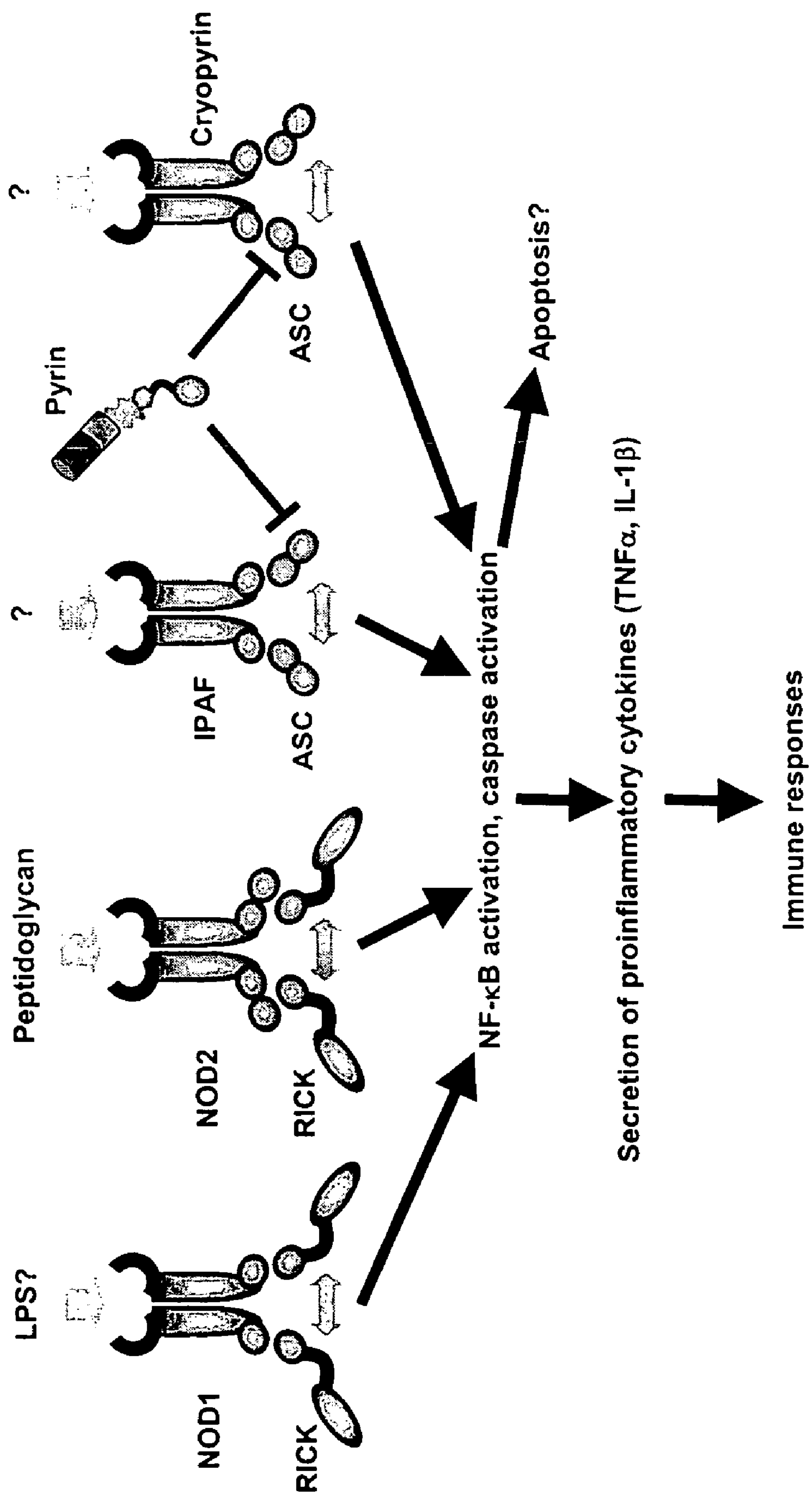
FIG. 3 shows signaling pathways mediated by NOD1, NOD2, IPAF and Cryopyrin.
Figure 4:
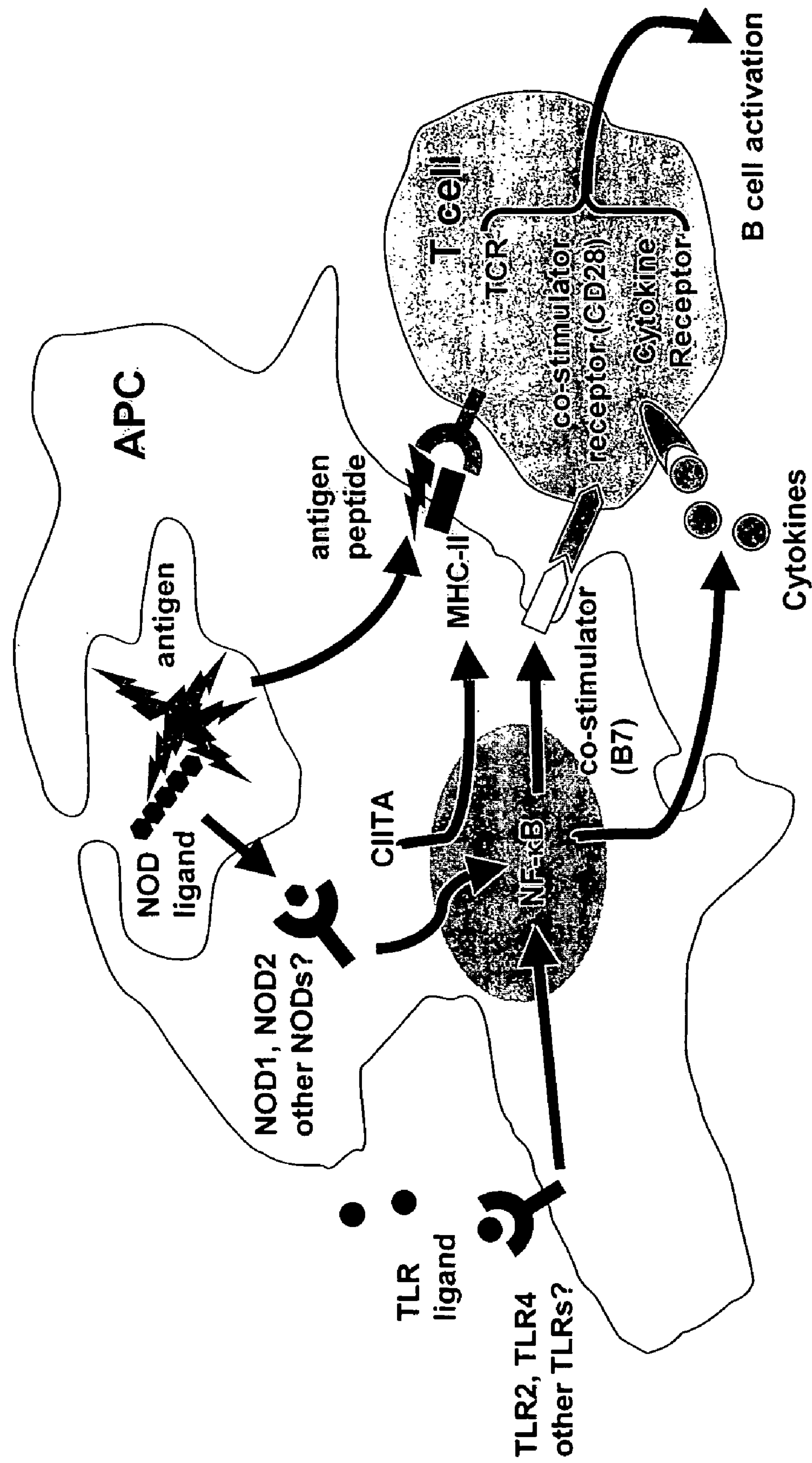
FIG. 4 shows a model for the role of NOD1, NOD2 and related NODs in innate and adaptive immunity. APC, antigen-presenting cell; MHC-II, major histocompatibility complex class II molecules; TCR, T-cell receptor; TLR, Toll-like receptors.

Some NOD proteins share the same type of effector domain (e.g., CARD or PYD). In some embodiments, the NOD proteins activate different signaling cascades as the interaction between these domains and those present in downstream binding partners is highly specific. For example, the PYD of ASC, a downstream adaptor molecule involved in NOD signalling, associates with the PYD of cryopyrin, but not with the PYD present in NALP2, PAN2, PYPAF3, PYPAF4, PYPAF6 or NOD27 (Grenier et al., *FEBS Lett.* 530, 73–78 (2002)). In other embodiments, certain NOD proteins like NOD1 and NOD2 interact with and use a common downstream molecule, RICK, to activate identical or similar signalling pathways (FIG. 3). Transient expression of NOD1 and NOD2 in mammalian cells induces NF-κB activation (Bertin et al., *J. Biol. Chem.* 274, 12955–12958 (1999); Inohara et al., *J. Biol. Chem.* 274, 14560–14567 (1999); Ogura et al., *J. Biol. Chem.* 276, 4812–4818 (2001)). Mutational analyses demonstrated that the CARDs and the NODs of NOD1 and NOD2 were required for the induction of NF-κB whereas its LRRs were dispensable (Inohara et al., *J. Biol. Chem.* 274, 14560–14567 (1999); Ogura et al., *J. Biol. Chem.* 276, 4812–4818 (2001)). Thus, in some embodiments, the CARDs act as effector domains for NOD1 and NOD2 signalling. Both NOD1 and NOD2 physically associate with RICK, a CARD-containing protein kinase through homophilic CARD-CARD interactions (Inohara et al., *J. Biol. Chem.* 274, 14560–14567 (1999); Ogura et al., *J. Biol. Chem.* 276, 4812–4818 (2001)). A role for RICK in NOD1 and NOD2 signalling is supported by several studies (Inohara et al., supra; Ogura et al., supra).

Several NOD-LRR proteins, including IPAF, cryopyrin, and DEFCAP, associate with ASC (Manji et al., *J. Biol. Chem.* 277, 11570–11575 (2002); Geddes et al., *Biochem. Biophys. Res. Commun.* 284, 77–82 (2001); Martinon et al., *Mol. Cell.* 10, 417–426 (2002)). ASC (also called TMSI/PYCARD) is an adaptor molecule originally identified in a sub-cytosolic fraction called the "speck" in cells undergoing apoptosis. ASC is composed of an amino-terminal PYD and a carboxy-terminal CARD. Co-expression of ASC with several PYD-containing NOD proteins including cryopyrin, PYPAF5 or PYPAF7, as well as with the CARD-containing IPAF, induces NF-κB activation (Manji et al., supra). Thus, in some embodiments, PYD-containing NOD proteins use the adaptor ASC for signaling (Grenier et al., supra). NF-κB activation induced through ASC signalling is inhibited by dominant forms of NEMO/IKKγ (Manji et al., supra; Grenier et al., supra). Thus, ASC signals, as was reported for RICK, through the common IKK signalling pathway of NF-κB activation (FIG. 3).

Multiple NOD proteins including NOD1, NOD2, IPAF and DEFCAP promote activation of pro-inflammatory caspases. For example, NOD1 promotes caspase-1 activation in transient overexpression studies (Yoo et al., *Biochem. Biophys. Res. Commun.* 299, 652–658 (2002)). IPAF, cryopyrin, DEFCAP, PYPAF5 and PYPAF7 have been found to regulate, in the presence of ASC, the activation of caspase-1, interleukin-1β converting enzyme (Grenier et al., supra; Wang et al., *J. Biol. Chem.* 277, 29874–29880 (2002)). DEFCAP, the only NOD family member known to possess both a CARD and PYD, can form an endogenous multi-protein complex containing ASC, caspase-1 and caspase-5 dubbed "the inflammasome" which promotes caspase activation and processing of pro-interleukin-1β (Martinon et al., *Mol. Cell.* 10, 417–426 (2002)).

In some embodiments, NOD proteins (e.g., Apaf-1, NOD1, NOD2, DEFCAP, IPAF and cryopyrin) induce or enhance apoptosis (Inohara et al., *J. Biol. Chem.* 274, 14560–14567 (1999); Ogura et al., *J. Biol. Chem.* 276, 4812–4818 (2001); Geddes et al., *Biochem. Biophys. Res. Commun.* 284, 77–82 (2001); Poyet et al., *J. Biol. Chem.* 276, 28309–28313 (2001); Hlaing et al., *J. Biol. Chem.* 276, 9230–9238 (2001); Zou et al., *Cell* 90, 405–413 (1997)). For example, NOD1 and DEFCAP interact with multiple caspases and/or Apaf-1 (Hlaing et al., supra; Inohara and Nuñez, *Oncogene,* 20, 6473–6481 (2001)). Co-expression of IPAF or cryopyrin with ASC or forced oligomerization of IPAF or cryopyrin induces apoptosis in mammalian cells, which requires caspase activity. NOD1, IPAF, cryopyrin, PYPAF5 and PYPAF7 induce both NF-κB and caspase-1 activation. Thus, in some embodiments, NOD pro-apoptotic activity results from the activation of inflammatory caspases. In other embodiments, apoptotic caspases contribute to the activation of inflammatory caspases.

In some embodiments, the induction of both NF-κB and apoptosis by NOD proteins is similar to that observed with TLRs, PKR and death receptors (DRs), which induce apoptosis through the activation of caspases. Upon DR signalling, the induction of apoptosis is suppressed in vivo by simultaneous activation of NF-κB, which leads to the expression of anti-apoptotic genes (Beg and Baltimore, *Science* 274, 782–784 (1996); Wang et al., *Science* 281, 1680–1683 (1998); Micheau et al., *Mol. Cell. Biol.* 21, 5299–5305 (2001)). Thus, in some embodiments, under physiological conditions, the pro-apoptotic activity induced through NOD proteins is suppressed by simultaneous induction of NF-κB activity.

Genetic variation in three human NOD proteins has been implicated in the development of genetic diseases (Hull et al., *Curr Opin Rheumatol.* 15, 61–69 (2003)). For example, mutations in CIITA are known to cause type II lymphocyte bare syndrome (LBS), a hereditary immunodeficiency disorder characterized by the absence of MHCII expression (Steimle et al., *Cell* 75, 135–146 (1993); Reith and Mach, *Annu Rev Immunol.* 19, 331–373. (2001)). More recently, mutations in NOD2 and CIAS1 (the gene encoding cryopyrin) have been implicated in several autoinflammatory diseases. A frameshift mutation, L1007fsinsC, and two missense mutations (G908R and R702W) in NOD2 are associated with Crohn's disease (CD), a common inflammatory disease of the intestinal tract (Ogura et al., *Nature*

411, 603–606 (2001); Hugot et al., *Nature* 411, 599–603 (2001); Hampe et al., *Lancet* 357, 1925–1928 (2001)). Having one copy of the mutated alleles confers a 2–4-fold increased risk of developing CD, whereas homozygocity or compound heterozygocity for NOD2 mutations increases the risk 20–40-fold, indicating that lack of NOD2 function is important for disease development. All three CD-associated mutations result in proteins that are deficient in inducing PGN- and MDP-mediated NF-κB activation. Activation of NF-κB induced by MDP is absent in mononuclear cells derived from CD patients homozygous for L1007fsinsC.

In addition to CD, missense mutations in the coding region of NOD2 have been associated with Blau syndrome, an autosomal dominant trait characterized by arthritis, uveitis and skin rashes (Miceli-Richard et al., *Nat. Genet.* 29, 19–20 (2001)). NOD2 mutations resulting in Blau syndrome are located in the NOD (Miceli-Richard et al., supra). NOD2 mutant proteins found in patients with Blau syndrome induce increased basal NF-κB activity, when compared to wild-type NOD2. Thus, variant proteins found in patients with Blau syndrome may represent constitutively active NOD2 mutations. This is in contrast to CD-associated NOD2 variants, which have normal or reduced levels of basal activity but are defective in their response bacterial components (Ogura et al., *Nature* 411, 603–606 (2001); Bonen et al., *Gastroenterology* 124, 140–146 (2003)).

Figure 5:
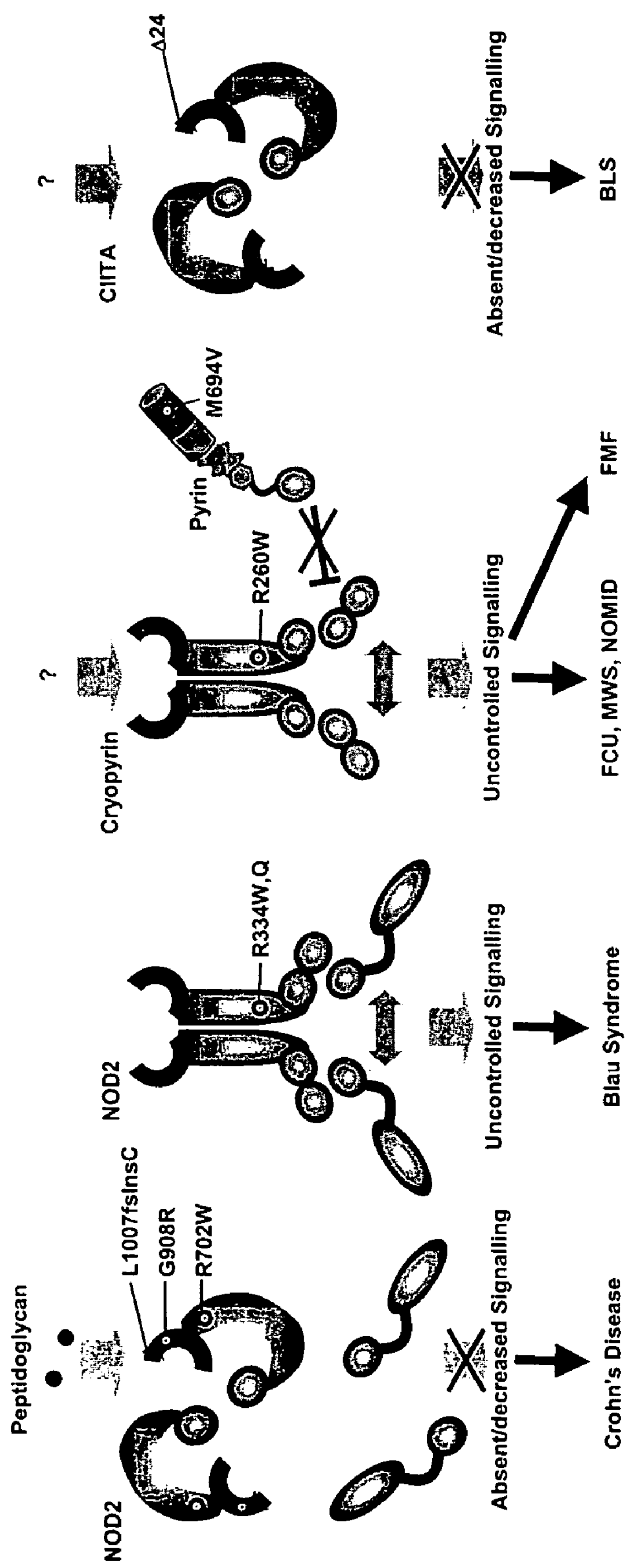
FIG. 5 shows hypothetical mechanisms of disease in patients with mutations in NOD2, Cryopyrin, CIITA and Pyrin.

Mutations in the CIAS1 gene, which encodes cryopyrin, are the cause of several autoinflammatory syndromes characterized by recurrent episodes of seemingly unprovoked inflammation (Hoffman et al., *Nature Genet.* 29, 301–305 (2001); Feldmann et al., *Am. J. Hum. Genet.* 71, 198–203 (2002); Aksentijevich et al., *Arthritis Rheum.* 46, 3340–3348 (2002); Aganna et al., *Arthritis Rheum.,* 46, 2445–2452 (2002)). These autosomal-dominant diseases include familial cold autoinflammatory syndrome (FACS), Muckle-Wells syndrome (MWS) and neonatal-onset multisystem inflammatory disease (NOMID, also known as chronic infantile neurologic cutaneous articular syndrome or CINCA). Patients with FACS, MWS and NOMID carry missense mutations that localize to the NOD of cryopyrin. The R260W mutation associated with FACS and MWS corresponds to the R334W NOD2 mutation found in Blau syndrome (Miceli-Richard et al., supra). The present invention is not limited to a particular mechanism. Indeed, an understanding of the mechanism of the present invention is not required to practice the present invention. Nonetheless, it is contemplated that this observation suggests that R206W cryopyrin may represent a constitutively active mutation which may lead to a deregulated activation of NF-κB and inflammatory caspases (FIG. 5).

Pyrin has been implicated in familial Mediterranean fever (FMF), an autosomal-recessive disease characterized by recurrent episodes of fever and localized inflammation (The International FMF Consortium, *Cell* 90, 797–807 (1997)). The gene mutated in FMF encodes a protein called pyrin, which is composed of an amino-terminal PYD, a B-type zinc-finger box, a coiled coil, a PRY domain and a Sp1a and Ryanodine receptor (SPRY) domain (The International FMF Consortium, supra).

In some embodiments, the present invention provides novel NOD genes (e.g., those described in SEQ ID NOs: 1–22 and Table 1). The novel NOD genes of the present invention were identified by searching public gene databases for proteins with homology to known NOD proteins. The present invention is not limited to a particular mechanism. Indeed, an understanding of the mechanism of the present invention is not necessary to understand the present invention. Nonetheless, it is contemplated that these genes are associated with inflammatory diseases. In particular, analysis conducted during the course of development of the present invention revealed that linkage analysis of NOD27 revealed a locus in the chromosomal region that is associated with psoriasis. Accordingly, it is further contemplated that NOD27 is associated with psoriasis.

In some embodiments, the present invention provides an "expression profile" of inflammatory diseases. For example, in some embodiments, the expression and or presence of variant alleles of the NOD proteins of the present invention is determined. Such expression profiles can then be correlated with disease states or susceptibility to disease.

DETAILED DESCRIPTION OF THE INVENTION

The present invention relates to the NOD proteins and nucleic acids encoding the NOD proteins. The present invention further provides assays for the detection of NOD polymorphisms and mutations associated with disease states. Exemplary embodiments of the present invention are described below.

I. NOD Polynucleotides

As described above, the present invention provides novel NOD family genes. Accordingly, the present invention provides nucleic acids encoding NOD genes, homologs, variants (e.g., polymorphisms and mutants), including but not limited to, those described in SEQ ID NOs: 1–11. Table 1 describes the NOD genes of the present invention. In some embodiments, the present invention provide polynucleotide sequences that are capable of hybridizing to SEQ ID NOs: 1–11 under conditions of low to high stringency as long as the polynucleotide sequence capable of hybridizing encodes a protein that retains a biological activity of the naturally occurring NODs. In some embodiments, the protein that retains a biological activity of naturally occurring NOD is 70% homologous to wild-type NOD, preferably 80% homologous to wild-type NOD, more preferably 90% homologous to wild-type NOD, and most preferably 95% homologous to wild-type NOD. In preferred embodiments, hybridization conditions are based on the melting temperature ($T_m$) of the nucleic acid binding complex and confer a defined "stringency" as explained above (See e.g., Wahl, et al., Meth. Enzymol., 152:399–407 [1987], incorporated herein by reference).

In other embodiments of the present invention, additional alleles of NOD genes are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Examples of the alleles of the present invention include those encoded by SEQ ID NOs:1–11 (wild type) and disease alleles thereof.

In still other embodiments of the present invention, the nucleotide sequences of the present invention may be engineered in order to alter an NOD coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of NOD may be extended utilizing the nucleotide sequence (e.g., SEQ ID NOs: 1–11) in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318–22 [1993]). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055–60 [1991]). The PROMOTERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed NOD sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., NOD function) for such purposes as altering the biological activity (e.g., Nod signaling). Such modified peptides are considered functional equivalents of peptides having an activity of a NOD peptide as defined herein. A modified peptide can be produced in which the nucleotide sequence encoding the polypeptide has been altered, such as by substitution, deletion, or addition. In particularly preferred embodiments, these modifications do not significantly reduce the biological activity of the modified NOD genes. In other words, construct "X" can be evaluated in order to determine whether it is a member of the genus of modified or variant NOD's of the present invention as defined functionally, rather than structurally. In preferred embodiments, the activity of variant NOD polypeptides is evaluated by methods described herein (e.g., the generation of transgenic animals or the use of signaling assays).

Moreover, as described above, variant forms of NOD genes are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of NOD disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17–21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a NOD coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

TABLE 1

| Nod Genes | | |
|---|---|---|
| Nod Gene | SEQ ID NO (Nucleic acid) | SEQ ID NO (Polypeptide) |
| Nod3 | 1 | 12 |
| Nod5 | 2 | 13 |
| Nod6 | 3 | 14 |
| Nod8 | 4 | 15 |
| Nod9 | 5 | 16 |
| Nod12 | 6 | 17 |
| Nod14 | 7 | 18 |
| Nod16 | 8 | 19 |
| Nod17 | 9 | 20 |
| Nod26 | 10 | 21 |
| Nod27 | 11 | 22 |

II. NOD Polypeptides

In other embodiments, the present invention provides NOD polynucleotide sequences that encode NOD polypeptide sequences (e.g., the polypeptides of SEQ ID NOs: 12–22). Other embodiments of the present invention provide fragments, fusion proteins or functional equivalents of these NOD proteins. In some embodiments, the present invention provides mutants of NOD polypeptides. In still other embodiments of the present invention, nucleic acid sequences corresponding to NOD variants, homologs, and mutants may be used to generate recombinant DNA molecules that direct the expression of the NOD variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NOs: 1–11 that encode substantially the same or a functionally equivalent amino acid sequence, may be used to clone and express NOD. In general, such polynucleotide sequences hybridize to SEQ ID NOs:1–11 under conditions of high to medium stringency as described above. As will be understood by those of skill in the art, it may be advantageous to produce NOD-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of NOD expression or to produce recombinant RNA transcripts having desirable properties, such as a longer half-life, than transcripts produced from naturally occurring sequence.

1. Vectors for Production of NOD

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 1–11). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NOs: 1–11) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of genes in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of NOD Polypeptides

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of NOD Polypeptides

The present invention also provides methods for recovering and purifying NOD polypeptides from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having a coding sequence of a NOD gene (e.g., SEQ ID NOs: 1–11) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of NOD Polypeptide

In addition, the present invention provides fragments of NOD polypeptides (i.e., truncation mutants). In some embodiments of the present invention, when expression of a portion of the NOD protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751 [1987]) and *Salmonella typhimurium* and its in vitro activity has been demonstrated on recombinant proteins (Miller et al., Proc. Natl. Acad. Sci. USA 84:2718 [1990]). Therefore, removal of an N-terminal methionine, if desired, can be achieved either in vivo by expressing such recombinant polypeptides in a host which produces MAP (e.g., *E. coli* or CM89 or *S. cerivisiae*), or in vitro by use of purified MAP.

5. Fusion Proteins Containing NOD

The present invention also provides fusion proteins incorporating all or part of the NOD polypeptides of the present invention. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a NOD protein. In some embodiments of the present invention, the VP6 capsid protein of rotavirus is used as an immunologic carrier protein for portions of a NOD polypeptide, either in the monomeric form or in the form of a viral particle. In other embodiments of the present invention, the nucleic acid sequences corresponding to the portion of a NOD polypeptide against which antibodies are to be raised can be incorporated into a fusion gene construct which includes coding sequences for a late vaccinia virus structural protein to produce a set of recombinant viruses expressing fusion proteins comprising a portion of NOD as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of a NOD polypeptide and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of NOD is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the NOD proteins can also be expressed and presented by bacterial cells.

In addition to utilizing fusion proteins to enhance immunogenicity, it is widely appreciated that fusion proteins can also facilitate the expression of proteins, such as a NOD protein of the present invention. Accordingly, in some embodiments of the present invention, NOD polypeptides can be generated as glutathione-S-transferase (i.e., GST fusion proteins). It is contemplated that such GST fusion proteins will enable easy purification of NOD polypeptides, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of a NOD polypeptide, can allow purification of the expressed NOD fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of NOD

Still other embodiments of the present invention provide mutant or variant forms of NOD polypeptides (i.e., muteins). It is possible to modify the structure of a peptide having an activity of a NOD polypeptide of the present invention for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject NOD proteins as defined herein. A modified peptide can be produced in which the amino acid sequence has been altered, such as by amino acid substitution, deletion, or addition.

Moreover, as described above, variant forms (e.g., mutants or polymorphic sequences) of the subject NOD proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present NOD proteins, as well as truncation mutants, and is especially useful for identifying potential variant sequences (i.e., mutants or polymorphic sequences) that are involved in inflammatory diseases or resistance to inflammatory diseases. The purpose of screening such combinatorial libraries is to generate, for example, novel NOD variants that can act as either agonists or antagonists, or alternatively, possess novel activities all together.

Therefore, in some embodiments of the present invention, NOD variants are engineered by the present method to provide altered (e.g., increased or decreased) biological activity. In other embodiments of the present invention, combinatorially-derived variants are generated which have a selective potency relative to a naturally occurring NOD. Such proteins, when expressed from recombinant DNA constructs, can be used in gene therapy protocols.

Still other embodiments of the present invention provide NOD variants that have intracellular half-lives dramatically different than the corresponding wild-type protein. For example, the altered protein can be rendered either more stable or less stable to proteolytic degradation or other cellular process that result in destruction of, or otherwise inactivate NOD polypeptides. Such variants, and the genes which encode them, can be utilized to alter the location of NOD expression by modulating the half-life of the protein. For instance, a short half-life can give rise to more transient NOD biological effects and, when part of an inducible expression system, can allow tighter control of NOD levels within the cell. As above, such proteins, and particularly their recombinant nucleic acid constructs, can be used in gene therapy protocols.

In still other embodiments of the present invention, NOD variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of NOD homologs, variants or other related proteins are aligned, preferably to promote the highest homology possible. Such a population of variants can include, for example, NOD homologs from one or more species, or NOD variants from the same species but which differ due to mutation or polymorphisms. Amino acids that appear at each position of the aligned sequences are selected to create a degenerate set of combinatorial sequences.

In a preferred embodiment of the present invention, the combinatorial NOD library is produced by way of a degenerate library of genes encoding a library of polypeptides which each include at least a portion of potential NOD protein sequences. For example, a mixture of synthetic oligonucleotides can be enzymatically ligated into gene sequences such that the degenerate set of potential NOD sequences are expressible as individual polypeptides, or alternatively, as a set of larger fusion proteins (e.g., for phage display) containing the set of NOD sequences therein.

There are many ways by which the library of potential NOD homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential NOD sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the* 3rd *Cleveland Symposium on Macromolecules*, Elsevier, Amsterdam, pp 273–289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; each of which is herein incorporated by reference; as well as U.S. Pat. Nos. 5,223,409, 5,198,346, and 5,096,815; each of which is incorporated herein by reference).

It is contemplated that the NOD nucleic acids of the present invention (e.g., SEQ ID NOs:1–11, and fragments and variants thereof) can be utilized as starting nucleic acids for directed evolution. These techniques can be utilized to develop NOD variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1:17–24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for NOD activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for NOD activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of NOD homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of NOD Polypeptides

In an alternate embodiment of the invention, the coding sequence of NOD is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 [1981]). In other embodiments of the present invention, the protein itself is produced using chemical methods to synthesize either an entire NOD amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, WH Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example, using ABI 431A Peptide Synthesizer (Perkin Elmer) in accordance with the instructions provided by the manufacturer. Additionally, the amino acid sequence of a NOD polypeptide, or any part thereof, may be altered during direct synthesis and/or combined using chemical methods with other sequences to produce a variant polypeptide.

III. Detection of NOD Alleles

In some embodiments, the present invention provides methods of detecting the presence of wild type or variant (e.g., mutant or polymorphic) NOD nucleic acids or polypeptides. The detection of mutant NOD polypeptides finds use in the diagnosis of disease (e.g., inflammatory disease).

A. Detection of Variant NOD Alleles

In some embodiments, the present invention provides alleles of NOD that increase a patient's susceptibility to inflammatory diseases. Any mutation that results in an altered phenotype (e.g., increase in inflammatory disease or resistance to inflammatory disease) is within the scope of the present invention.

Accordingly, the present invention provides methods for determining whether a patient has an increased susceptibility to an inflammatory disease by determining whether the individual has a variant NOD allele. In other embodiments, the present invention provides methods for providing a prognosis of increased risk for inflammatory disease to an individual based on the presence or absence of one or more variant alleles of NOD.

A number of methods are available for analysis of variant (e.g., mutant or polymorphic) nucleic acid sequences. Assays for detection variants (e.g., polymorphisms or mutations) fall into several categories including, but not limited to, direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following exemplary assays are useful in the present invention: directs sequencing assays, PCR assays, mutational analysis by dHPLC (e.g., available from Transgenomic, Omaha, Nebr. or Varian, Palo Alto, Calif.), fragment length polymorphism assays (e.g., RFLP or CFLP (See e.g. U.S. Pat. Nos. 5,843,654; 5,843,669; 5,719,208; and 5,888,780; each of which is herein incorporated by reference)), hybridization assays (e.g., direct detection of hybridization, detection of hybridization using DNA chip assays (See e.g., U.S. Pat. Nos. 6,045,996; 5,925,525; 5,858,659; 6,017,696; 6,068,818; 6,051,380; 6,001,311; 5,985,551; 5,474,796; PCT Publications WO 99/67641 and WO 00/39587, each of which is herein incorporated by reference), enzymatic detection of hybridization (See e.g., U.S. Pat. Nos. 5,846,717, 6,090,543; 6,001,567; 5,985,557; 5,994,069; 5,962,233; 5,538,848; 5,952,174 and 5,919,626, each of which is herein incorporated by reference)), and mass spectrometry assays. In addition, assays for the detection of variant NOD proteins find use in the present invention (e.g., cell free translation methods, See e.g., U.S. Pat. No. 6,303,337, herein incorporated by reference) and antibody binding assays.

B. Kits for Analyzing Risk of Inflammatory Disease

The present invention also provides kits for determining whether an individual contains a wild-type or variant (e.g., mutant or polymorphic) allele or polypeptide of NOD. In some embodiments, the kits are useful determining whether the subject is at risk of developing an inflammatory disease (e.g., Crohn's disease or psoriasis). The diagnostic kits are produced in a variety of ways. In some embodiments, the kits contain at least one reagent for specifically detecting a mutant NOD allele or protein. In preferred embodiments, the reagent is a nucleic acid that hybridizes to nucleic acids containing the mutation and that does not bind to nucleic acids that do not contain the mutation. In other embodiments, the reagents are primers for amplifying the region of DNA containing the mutation. In still other embodiments, the reagents are antibodies that preferentially bind either the wild-type or mutant NOD proteins.

In some embodiments, the kit contains instructions for determining whether the subject is at risk for an inflammatory disease. In preferred embodiments, the instructions specify that risk for developing an inflammatory disease is determined by detecting the presence or absence of a mutant NOD allele in the subject, wherein subjects having an mutant allele are at greater risk for developing an inflammatory disease.

The presence or absence of a disease-associated mutation in a NOD gene can be used to make therapeutic or other medical decisions. For example, couples with a family history of inflammatory diseases may choose to conceive a child via in vitro fertilization and pre-implantation genetic screening. In this case, fertilized embryos are screened for mutant (e.g., disease associated) alleles of a NOD gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a NOD allele known to be associated with an inflammatory disease allows for early intervention (e.g., genetic or pharmaceutical therapies).

In some embodiments, the kits include ancillary reagents such as buffering agents, nucleic acid stabilizing reagents, protein stabilizing reagents, and signal producing systems (e.g., florescence generating systems as Fret systems). The test kit may be packaged in any suitable manner, typically with the elements in a single container or various containers as necessary along with a sheet of instructions for carrying out the test. In some embodiments, the kits also preferably include a positive control sample.

C. Bioinformatics

In some embodiments, the present invention provides methods of determining an individual's risk of developing an inflammatory disease based on the presence of one or more variant alleles of a NOD gene. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting an inflammatory disease associated with a given polymorphism, as well as the sequences). In some embodiments, one of the computers stores application programs (e.g., for analyzing the results of detection assays). Results are then delivered to the user (e.g., via one of the computers or via the internet.

For example, in some embodiments, a computer-based analysis program is used to translate the raw data generated by the detection assay (e.g., the presence, absence, or amount of a given NOD allele or polypeptide) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant NOD genes or polypeptides), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing an inflammatory disease) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the association of a given NOD allele with inflammatory diseases.

IV. Generation of NOD Antibodies

The present invention provides isolated antibodies or antibody fragments (e.g., FAB fragments). Antibodies can be generated to allow for the detection of a NOD protein of the present invention. The antibodies may be prepared using various immunogens. In one embodiment, the immunogen is a human NOD peptide to generate antibodies that recognize human NOD. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against a NOD polypeptide. For the production of antibody, various host animals can be immunized by injection with the peptide corresponding to the NOD epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward NOD, it is contemplated that any technique that provides for the production of antibody molecules by continuous cell lines in culture will find use with the present invention (See e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köher and Milstein, Nature 256:495–497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., *in Monoclonal Antibodies and Cancer Therapy*, Alan R. Liss, Inc., pp. 77–96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026–2030 [1983]) or by transforming human B cells with EBV virus in vitro (Cole et al., *in Monoclonal Antibodies and Cancer Therapy*, Alan R. Liss, pp. 77–96 [1985]).

In addition, it is contemplated that techniques described for the production of single chain antibodies (U.S. Pat. No. 4,946,778; herein incorporated by reference) will find use in producing NOD specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for a NOD polypeptide.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., N.Y.; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of NOD (e.g., for Western blotting), measuring levels thereof in appropriate biological samples, etc. The antibodies can be used to detect a NOD in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of a human NOD using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of NOD detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of NOD or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of NOD. Such antibodies can also be used diagnostically to measure abnormal expression of NOD, or the aberrant formation of protein complexes, which may be indicative of a disease state.

V. Gene Therapy Using NOD

The present invention also provides methods and compositions suitable for gene therapy to alter NOD expression, production, or function. As described above, the present invention provides human NOD genes and provides methods of obtaining NOD genes from other species. Thus, the methods described below are generally applicable across many species. In some embodiments, it is contemplated that the gene therapy is performed by providing a subject with a wild-type allele of a NOD gene (i.e., an allele that does not contain a NOD disease allele (e.g., free of disease causing polymorphisms or mutations). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980–990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320–330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626–630 [1992]; See also, La Salle et al., Science 259:988–990 [1993]); and a defective adeno-associated virus vector (Samulski et al., J. Virol., 61:3096–3101 [1987]; Samulski et al., J. Virol., 63:3822–3828 [1989]; and Lebkowski et al., Mol. Cell. Biol., 8:3988–3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol., 75–81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1–L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No., 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413–7417 [1987]; See also, Mackey, et al., Proc. Natl. Acad. Sci. USA 85:8027–8031 [1988]; Ulmer et al., Science 259:1745–1748 [1993]). The use of cationic lipids may promote encapsulation of negatively charged nucleic acids, and also promote fusion with negatively charged cell membranes (Felgner and Ringold, Science 337:387–388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

VI. Transgenic Animals Expressing Exogenous NOD Genes and Homologs, Mutants, and Variants Thereof The present invention contemplates the generation of transgenic animals comprising an exogenous NOD gene or homologs, mutants, or variants thereof. In preferred embodiments, the transgenic animal displays an altered phenotype as compared to wild-type animals. In some embodiments, the altered phenotype is the overexpression of mRNA for a NOD gene as compared to wild-type levels of NOD expression. In other embodiments, the altered phenotype is the decreased expression of mRNA for an endogenous NOD gene as compared to wild-type levels of endogenous NOD expression. In some preferred embodiments, the transgenic animals comprise mutant alleles of NOD. Methods for analyzing the presence or absence of such phenotypes include Northern blotting, mRNA protection assays, and RT-PCR. In other embodiments, the transgenic mice have a knock out mutation of a NOD gene. In preferred embodiments, the transgenic animals display an altered susceptibility to inflammatory diseases.

Such animals find use in research applications (e.g., identifying signaling pathways that a NOD protein is involved in), as well as drug screening applications (e.g., to screen for drugs that prevent or treat inflammatory diseases. For example, in some embodiments, test compounds (e.g., a drug that is suspected of being useful to treat an inflammatory disease are administered to the transgenic animals and control animals with a wild type NOD allele and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1–2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438–4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which a particular domain of a NOD is deleted). Methods for homologous recombination are described in U.S. Pat. No. 5,614,396, incorporated herein by reference.

VIII. Drug Screening Using NOD

In some embodiments, the isolated nucleic acid and polypeptides of NOD genes of the present invention (e.g., SEQ ID NOS: 1–22) and related proteins and nucleic acids are used in drug screening applications for compounds that alter (e.g., enhance or inhibit) NOD activity and signaling. The present invention further provides methods of identifying ligands of the NOD proteins of the present invention.

As described above, NOD family proteins (e.g., Nod2) have been shown to mediate the host response to bacterial muropeptides. The present invention is not limited to a particular mechanism. Indeed, an understanding of the mechanism is not necessary to practice the present invention. Nonetheless, it is contemplated that the NOD family proteins of the present invention are involved in host responses to microbes (e.g., bacteria, virus, fungi, etc.). It is further contemplated that some NODs recognize endogenous compounds (e.g., derived from host cells) as ligands. For example, some NODs may recognize host cell proteins induced by stress (e.g. heat shock proteins). Accordingly, in some embodiments, the present invention provides methods of screening for ligands of NOD family proteins (e.g., ligands derived from microbes or host factors). For example, in some embodiments, an assay that measures NOD signaling is used to screen libraries of compounds (e.g., microbial or host derived compounds) for their ability to alter NOD family signaling.

In other embodiments, the present invention provides methods of screening compounds for the ability to alter NOD signaling mediated by natural ligands (e.g., identified using the methods described above). Such compounds find use in the treatment of disease mediated by NOD family members (e.g., inflammatory diseases).

In one screening method, the two-hybrid system is used to screen for compounds (e.g., proteins) capable of altering NOD function(s) (e.g., interaction with a binding partner) in vitro or in vivo. In one embodiment, a GAL4 binding site, linked to a reporter gene such as lacZ, is contacted in the presence and absence of a candidate compound with a GAL4 binding domain linked to a NOD fragment and a GAL4 transactivation domain II linked to a binding partner fragment. Expression of the reporter gene is monitored and a decrease in the expression is an indication that the candidate compound inhibits the interaction of a NOD with the binding partner. Alternately, the effect of candidate compounds on the interaction of a NOD with other proteins (e.g., proteins known to interact directly or indirectly with the binding partner) can be tested in a similar manner In some embodiments, the present invention provides methods of identifying NOD binding partners or ligands that utilize immunoprecipitation. In some embodiments, antibodies to NOD proteins are utilized to immunoprecipitated NODs and any bound proteins. In other embodiments, NOD fusion proteins are generated with tags and antibodies to the tags are utilized for immunoprecipitation. Potential binding partners that immunoprecipitate with NODs can be identified using any suitable method.

In another screening method, candidate compounds are evaluated for their ability to alter NOD signaling by contacting NOD, binding partners, binding partner-associated proteins, or fragments thereof, with the candidate compound and determining binding of the candidate compound to the peptide. The protein or protein fragments is/are immobilized using methods known in the art such as binding a GST-NOD fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., *E. coli* XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate NOD physiological effects (e.g., inflammatory disease).

In another screening method, one of the components of the NOD/binding partner signaling system is immobilized. Polypeptides can be immobilized using methods known in the art, such as adsorption onto a plastic microtiter plate or specific binding of a GST-fusion protein to a polymeric bead containing glutathione. For example, in some embodiments, GST-NOD is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of NOD with the other peptide. A variation of this method allows for the screening of compounds that are capable of disrupting a previously-formed protein/protein complex. For example, in some embodiments a complex comprising a NOD or a NOD fragment bound to another peptide is immobilized as described above and contacted with a candidate compound. The dissolution of the complex by the candidate compound correlates with the ability of the compound to disrupt or inhibit the interaction between NOD and the other peptide.

Another technique for drug screening provides high throughput screening for compounds having suitable binding affinity to NOD peptides and is described in detail in WO 84/03564, incorporated herein by reference. Briefly, large numbers of different small peptide test compounds are synthesized on a solid substrate, such as plastic pins or some other surface. The peptide test compounds are then reacted with NOD peptides and washed. Bound NOD peptides are then detected by methods well known in the art.

Another technique uses NOD antibodies, generated as discussed above. Such antibodies are capable of specifically binding to NOD peptides and compete with a test compound for binding to NOD. In this manner, the antibodies can be used to detect the presence of any peptide that shares one or more antigenic determinants of a NOD peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with NOD genes and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding NOD or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431–39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by NOD in operable association with a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

Specifically, the present invention provides screening methods for identifying modulators, i.e., candidate or test compounds or agents (e.g., proteins, peptides, peptidomimetics, peptoids, small molecules or other drugs) which bind to a NOD of the present invention, have an inhibitory (or stimulatory) effect on, for example, NOD expression or NOD activity, or have a stimulatory or inhibitory effect on, for example, the expression or activity of a NOD substrate. Compounds thus identified can be used to modulate the activity of target gene products (e.g., NOD genes) either directly or indirectly in a therapeutic protocol, to elaborate the biological function of the target gene product, or to identify compounds that disrupt normal target gene interactions. Compounds, which stimulate the activity of a variant NOD or mimic the activity of a non-functional variant are particularly useful in the treatment of inflammatory diseases.

In one embodiment, the invention provides assays for screening candidate or test compounds that are substrates of a NOD protein or polypeptide or a biologically active portion thereof. In another embodiment, the invention provides assays for screening candidate or test compounds that bind to or modulate the activity of a NOD protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678–85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl.

33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412–421 [1992]), or on beads (Lam, Nature 354:82–84 [1991]), chips (Fodor, Nature 364:555–556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386–390 [1990]; Devlin Science 249:404–406 [1990]; Cwirla et al., Proc. NatI. Acad. Sci. 87:6378–6382 [1990]; Felici, J. Mol. Biol. 222:301 [1991]).

In one embodiment, an assay is a cell-based assay in which a cell that expresses a NOD protein or biologically active portion thereof is contacted with a test compound, and the ability of the test compound to modulate a NOD's activity is determined. Determining the ability of the test compound to modulate NOD activity can be accomplished by monitoring, for example, changes in enzymatic activity. The cell, for example, can be of mammalian origin.

The ability of the test compound to modulate NOD binding to a compound, e.g., a NOD substrate, can also be evaluated. This can be accomplished, for example, by coupling the compound, e.g., the substrate, with a radioisotope or enzymatic label such that binding of the compound, e.g., the substrate, to a NOD can be determined by detecting the labeled compound, e.g., substrate, in a complex.

Alternatively, a NOD is coupled with a radioisotope or enzymatic label to monitor the ability of a test compound to modulate NOD binding to a NOD substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a NOD substrate) to interact with a NOD with or without the labeling of any of the interactants can be evaluated. For example, a microphysiorneter can be used to detect the interaction of a compound with a NOD without the labeling of either the compound or the NOD (McConnell et al. Science 257: 1906–1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and a NOD polypeptide.

In yet another embodiment, a cell-free assay is provided in which a NOD protein or biologically active portion thereof is contacted with a test compound and the ability of the test compound to bind to the NOD protein or biologically active portion thereof is evaluated. Preferred biologically active portions of NOD proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET)

(see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of a NOD protein to bind to a target molecule can be accomplished using real-time Biomolecular Interaction Analysis (BIA) (see, e.g., Sjolander and Urbaniczky, Anal. Chem. 63:2338–2345 [1991] and Szabo et al. Curr. Opin. Struct. Biol. 5:699–705 [1995]). "Surface plasmon resonance" or "BIA" detects biospecific interactions in real time, without labeling any of the interactants (e.g., B1Acore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize a NOD protein, an anti-NOD antibody or its target molecule to facilitate separation of complexed from non-complexed forms of one or both of the proteins, as well as to accommodate automation of the assay. Binding of a test compound to a NOD protein, or interaction of a NOD protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-NOD fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or NOD protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of NOD binding or activity determined using standard techniques. Other techniques for immobilizing either a NOD protein or a target molecule on matrices include using conjugation of biotin and streptavidin. Biotinylated NOD protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with NOD protein or target molecules but which do not interfere with binding of the NOD protein to its target molecule. Such antibodies can be derivatized to the wells of the plate, and unbound target or NOD protein trapped in the wells by antibody conjugation. Methods for detecting such complexes, in addition to those described above for the GST-immobilized complexes, include immunodetection of complexes using antibodies reactive with the NOD protein or target molecule, as well as enzyme-linked assays which rely on detecting an enzymatic activity associated with the NOD protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284–7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141–8 [1998]; Hageand Tweed J. Chromatogr. Biomed. Sci. Appl 699:499–525 [1997]). Further, fluorescence energy transfer may also be conveniently utilized, as described herein, to detect binding without further purification of the complex from solution.

The assay can include contacting the NOD protein or biologically active portion thereof with a known compound that binds the NOD to form an assay mixture, contacting the assay mixture with a test compound, and determining the ability of the test compound to interact with a NOD protein, wherein determining the ability of the test compound to interact with a NOD protein includes determining the ability of the test compound to preferentially bind to NOD or biologically active portion thereof, or to modulate the activity of a target molecule, as compared to the known compound.

To the extent that a NOD can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, a NOD protein can be used as a "bait protein" in a two-hybrid assay or three-hybrid assay (see, e.g., U.S. Pat. No. 5,283,317; Zervos et al., Cell 72:223–232 [1993]; Madura et al., J. Biol. Chem. 268.12046–12054 [1993]; Bartel et al., Biotechniques 14:920–924 [1993]; Iwabuchi et al., Oncogene 8:1693–1696 [1993]; and Brent WO 94/10300; each of which is herein incorporated by reference), to identify other proteins, that bind to or interact with a NOD ("NOD-binding proteins" or "NOD-bp") and are involved in NOD activity. Such NOD-bps can be activators or inhibitors of signals by the NOD proteins or targets as, for example, downstream elements of a NOD-mediated signaling pathway.

Modulators of NOD expression can also be identified. For example, a cell or cell free mixture is contacted with a candidate compound and the expression of a NOD mRNA or protein evaluated relative to the level of expression of the NOD mRNA or protein in the absence of the candidate compound. When expression of the NOD mRNA or protein is greater in the presence of the candidate compound than in its absence, the candidate compound is identified as a stimulator of a NOD mRNA or protein expression. Alternatively, when expression of NOD mRNA or protein is less (i.e., statistically significantly less) in the presence of the candidate compound than in its absence, the candidate compound is identified as an inhibitor of NOD mRNA or protein expression. The level of NOD mRNA or protein expression can be determined by methods described herein for detecting NOD mRNA or protein.

A modulating agent can be identified using a cell-based or a cell free assay, and the ability of the agent to modulate the activity of a NOD protein can be confirmed in vivo, e.g., in an animal such as an animal model for a disease (e.g., an animal with inflammatory disease).

B. Therapeutic Agents

This invention further pertains to novel agents identified by the above-described screening assays. Accordingly, it is within the scope of this invention to further use an agent identified as described herein (e.g., a NOD modulating agent or mimetic, a NOD specific antibody, or a NOD-binding partner) in an appropriate animal model (such as those described herein) to determine the efficacy, toxicity, side effects, or mechanism of action, of treatment with such an agent. Furthermore, as described above, novel agents identified by the above-described screening assays can be, e.g., used for treatments of inflammatory disease (e.g., including, but not limited to, psoriasis or Crohn's disease). In some embodiments, the agents are NOD ligands or ligand analogs (e.g., identified using the drug screening methods described above).

IX. Pharmaceutical Compositions Containing NOD Nucleic Acid, Peptides, and Analogs The present invention further provides pharmaceutical compositions which may comprise all or portions of NOD polynucleotide sequences, NOD polypeptides, inhibitors or antagonists of NOD bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by mutant NOD alleles (e.g., inflammatory disease). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, NOD nucleotide and NOD amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, NOD polynucleotide sequences or NOD amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of NOD may be that amount that suppresses apoptosis. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of NOD, conditions indicated on the label may include treatment of condition related to inflammatory diseases.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts NOD levels.

A therapeutically effective dose refers to that amount of NOD that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for NOD than for the inhibitors of NOD. Administration to the bone marrow may necessitate delivery in a manner different from intravenous injections.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A composition comprising an isolated and purified nucleic acid sequence encoding a protein having the amino acid sequence of SEQ ID NO:22.

2. The composition of claim 1, wherein said sequence is operably linked to a heterologous promoter.

3. A vector comprising the nucleic acid sequence of claim 1.

4. A host cell comprising the vector of claim 3.

5. The composition of claim 1, wherein said nucleic acid is selected from the group consisting of SEQ ID NO:11 and variants thereof that are at least 80% identical to SEQ ID NO: 11.

6. The composition of claim 1, wherein said nucleic acid sequence is SEQ ID NO11.

* * * * *

SEQUENCE LISTING

```
<160> NUMBER OF SEQ ID NOS: 22

<210> SEQ ID NO 1
<211> LENGTH: 3414
<212> TYPE: DNA
<213> ORGANISM: Homo sapiens

<400> SEQUENCE: 1

tgagaactca ggctggcaca gggattccca gggcatctac caccacgcag ctggagcagg      60

gctgagccca ggagcatgga gatggacgcc cccaggcccc ccagtcttgc tgtccctgga     120

gcagcatcga ggcccgggag gctgctggat gggggcacg gcaggcagca ggttcaggcc     180

ctctcttcac agctcctgga ggtgatcccc gactccatga ggaagcaaga ggtgcggacg     240

ggcagggagg ccggccaggg ccacggtacg ggctccccag ccgagcaggt gaaagccctc     300

atggatctgc tggctgggaa gggcagtcaa ggctcccacg ccccgcaggc cctggatagg     360

acaccggatg ccccgctggg gccctgcagc aatgactcaa ggatacagag gcaccgcaag     420

gccctgctga gcaaggtggg aggtggcccg gagctgggcg gaccctggca caggctggcc     480

tccctcctgc tggtggaggg cctgacggac ctgcagctga gggaacacga cttcacacag     540

gtggaggcca cccgcggggg cgggcacccc gccaggaccg tcgccctgga ccggctcttc     600
```

-continued

```
ctgcctctct cccgggtgtc tgtcccaccc cgggtctcca tcactatcgg ggtggccggc    660
atgggcaaga ccaccctggt gaggcacttc gtccgcctct gggcccatgg gcaggtcggc    720
aaggacttct cgctggtgct gcctctgacc ttccgggatc tcaacaccca cgagaagctg    780
tgtgccgacc gactcatctg ctcggtcttc ccgcacgtcg gggagcccag cctggcggtg    840
gcagtcccag ccagggccct cctgatcctg gacggcttgg atgagtgcag gacgcctctg    900
gacttctcca acaccgtggc ctgcacggac ccaaagaagg agatcccggt ggaccacctg    960
atcaccaaca tcatccgtgg caacctcttt ccggaagttt ccatctggat cacctcccgt   1020
cccagtgcat ctggccagat cccagggggc ctggtggacc ggatgacgga gatccggggc   1080
tttaacgagg aggagatcaa ggtgtgtttg gagcagatgt tccccgagga ccaggccctt   1140
ctgggctgga tgctgagcca agtgcaggct gacagggccc tgtacctgat gtgcaccgtc   1200
ccagccttct gcaggctcac ggggatggcg ctaggccacc tgtggcgcag caggacgggg   1260
ccccaggatg cagagctgtg gcccccgagg accctgtgcg agctctactc atggtacttt   1320
aggatggccc tcagcgggga ggggcaggag aagggcaagg caagccctcg catcgagcag   1380
gtggcccatg gtggccgcaa gatggtgggg acattgggcc gtctggcctt ccatgggctg   1440
ctcaagaaga aatacgtgtt ttacgagcaa gacatgaagg cgtttggtgt agacctcgct   1500
ctgctgcagg gcgccccgtg cagctgcttc ctgcagagag aggagacgtt ggcatcgtca   1560
gtggcctact gcttcaccca cctgtccctg caggagtttg tggcagccgc gtattactat   1620
ggcgcatcca ggagggccat cttcgacctc ttcactgaga gcggcgtatc ctggcccagg   1680
ctgggcttcc tcacgcattt caggagcgca gcccagcggg ccatgcaggc agaggacggg   1740
aggctggacg tgttcctgcg cttcctctcc ggcctcttgt ctccgagggt caatgccctc   1800
ctggccggct ccctgctggc ccaaggcgag caccaggcct accggaccca ggtggctgag   1860
ctcctgcagg gctgcctgcg ccccgatgcc gcagtctgtg cacgggccat caacgtgttg   1920
cactgcctgc atgagctgca gcacaccgag ctggcccgca gcgtggagga ggccatggag   1980
agcggggccc tggccaggct gactggtccc gcgcaccgcg ctgccctggc ctacctcctg   2040
caggtgtccg acgcctgtgc ccaggaggcc aacctgtccc tgagcctcag ccagggcgtc   2100
cttcagagcc tgctgcccca gctgctctac tgccggaagc tcaggctgga caccaaccag   2160
ttccaggacc ccgtgatgga gctgctgggc agcgtgctga gtgggaagga ctgtcgcatt   2220
cagaagatca gcttggcgga gaaccagatc agtaacaaag ggccaaagc tctggccaga    2280
tccctcttgg tcaacagaag tctgacctct ctggacctcc gcggtaactc cattggacca   2340
caaggggcca aggcgctggc agacgctttg aagatcaacc gcaccctgac ctccctgagc   2400
ctccagggca acaccgttag ggatgatggt gccaggtcca tggctgaggc cttggcctcc   2460
aaccggaccc tctccatgct gcacctgcag aagaacagca tcgggcccat gggagcccag   2520
cggatggcag atgccttgaa gcagaacagg agtctgaaag agctcatgtt ctccagtaat   2580
agtattggtg atggaggtgc caaggccctg gctgaggccc tgaaggtgaa ccagggcctg   2640
gagagcctgg acctgcagag caattccatc agtgacgcag gagtggcagc actgatgggg   2700
gccctctgca ccaaccagac cctcctcagc ctcagccttc gagaaaactc catcagtccc   2760
gagggagccc aggccatcgc tcatgccctc tgcgccaaca gcaccctgaa gaacctggac   2820
ctgacagcca acctcctcca cgaccagggt gcccgggcca tcgcagtggc agtgagagaa   2880
aaccgcaccc tcacctccct tcacctgcag tggaacttca tccaggccgg cgctgcccag   2940
gccctgggac aagcactaca gctcaacagg agcctcacca gcttagattt acaggagaac   3000
```

```
gccatcgggg atgacggagc gtgtgcggtg gcccgtgcac tgaaggtcaa cacagccctc   3060

actgctctct atctccaggt ggcctcaatt ggtgcttcag gcgcccaggt gctaggggaa   3120

gccttggctg tgaacagaac cttggagatt ctcgacttaa gaggaaatgc cattggggtg   3180

gctggagcca aagccctggc aaatgctctg aaggtaaact caagtctccg gagactcaat   3240

cttcaagaga attctctggg gatggacggg gcgatatgca ttgccacagc actgtctgga   3300

aaccacaggc tccagcatat caatctccag ggaaaccaca ttggggactc cggggccagg   3360

atgatctcag aggccatcaa gacaaatgct cccacgtgca ctgttgaaat gtga         3414
```

```
<210> SEQ ID NO 2
<211> LENGTH: 3521
<212> TYPE: DNA
<213> ORGANISM: Homo sapiens

<400> SEQUENCE: 2

aggcctgaat atttggacaa gatggcagat tcatcatcat cttctttctt tcctgatttt     60

gggctgctat tgtatttgga ggagctaaac aaagaggaat taaatacatt caagttattc    120

ctaaaggaga ccatggaacc tgagcatggc ctgacaccct ggaatgaagt gaagaaggcc    180

aggcgggagg acctggccaa tttgatgaag aaatattatc caggagagaa agcctggagt    240

gtgtctctca aaatctttgg caagatgaac ctgaaggatc tgtgtgagag agcgaaagaa    300

gagatcaact ggtcggccca gactatagga ccagatgatg ccaaggctgg agagacacaa    360

gaagatcagg aggcagtgct gggtgatgga acagaataca gaaatagaat aaaggaaaaa    420

ttttgcatca cttgggacaa gaagtctttg gctggaaagc ctgaagattt ccatcatgga    480

attgcagaga aagatagaaa actgttggaa cacttgttcg atgtggatgt caaaaccggt    540

gcacagccac agatcgtggt gcttcaggga gctgctggag ttgggaaaac aaccttggtg    600

agaaaggcaa tgttagattg ggcagagggc agtctctacc agcagaggtt taagtatgtt    660

ttttatctca atgggagaga aattaaccag ctgaaagaga gaagctttgc tcaattgata    720

tcaaaggact ggcccagcac agaaggcccc attgaagaaa tcatgtacca gccaagtagc    780

ctcttgttta ttattgacag tttcgatgaa ctgaactttg cctttgaaga acctgagttt    840

gcactgtgcg aagactggac ccaagaacac ccagtgtcct tcctcatgag tagtttgctg    900

aggaaagtga tgctccctga ggcatcctta ttggtgacaa caagactcac aacttctaag    960

agactaaagc agttgttgaa gaatcaccat tatgtagagc tactaggaat gtctgaggat   1020

gcaagagagg agtatattta ccagtttttt gaagataaga ggtgggccat gaaagtattc   1080

agttcactaa aaagcaatga gatgctgttt agcatgtgcc aagtcccccct agtgtgctgg   1140

gccgcttgta cttgtctgaa gcagcaaatg gagaagggtg gtgatgtcac attgacctgc   1200

caaacaacca cagctctgtt tacctgctat atttctagct tgttcacacc agtagatgga   1260

ggctctccta gtctacccaa ccaagcccag ctgagaagac tgtgccaagt cgctgccaaa   1320

ggaatatgga ctatgactta cgtgttttac agagaaaatc tcagaaggct tgggttaact   1380

caatctgatg tctctagttt tatggacagc aatattattc agaaggacgc agagtatgaa   1440

aactgctatg tgttcaccca ccttcatgtt caggagtttt ttgcagctat gttctatatg   1500

ttgaaaggca gttgggaagc tgggaaccct tcctgccagc cttttgaaga tttgaagtca   1560

ttacttcaaa gcacaagtta taaagacccc catttgacac agatgaagtg ctttttgttt   1620

ggcctttttga atgaagatcg agtaaaacaa ctggagagga cttttaactg taaaatgtca   1680
```

-continued

```
ctgaagataa aatcaaagtt acttcagtgt atggaagtat taggaaacag tgactattct   1740

ccatcacagc tgggatttct ggagttgttt cactgtctgt atgagactca agataaagcg   1800

tttataagcc aggcaatgag atgtttccca aaggttgcca ttaatatttg tgagaaaata   1860

catttgcttg tatcttcttt ctgccttaag cactgccggt gtttgcggac catcaggctg   1920

tctgtaactg tggtatttga gaagaagata ttaaaaacaa gcctcccaac taacacttgg   1980

gatggtgatc gcattactca ctgttggcaa gatctctgtt ctgtgcttca tacaaatgaa   2040

cacttgagag aattggacct gtaccatagc aaccttgata aatcagcaat gaatatcctg   2100

catcatgaac taaggcaccc aaactgtaaa ctacaaaagc tactgttgaa atttatcact   2160

ttccctgatg gttgtcagga tatctctact tctttgattc ataacaagaa tctgatgcat   2220

cttgacctaa aagggagtga tataggggat aatggagtaa agtcattgtg tgaggccttg   2280

aaacacccag agtgtaaact acagactctc aggctggaat cttgcaacct aactgtattt   2340

tgttgtctaa atatatctaa tgctctcatc agaagccaga gcctgatatt tctgaatctg   2400

tcaaccaata atctgttgga tgatggagtg cagcttttgt gtgaggcctt aagacatcca   2460

aagtgttatc tagagagact gtccttagaa agctgtggtc tcacagaggc tggctgtgag   2520

tatctttctt tggctctcat cagcaataaa agactgacac atttgtgctt ggcagacaat   2580

gtcttgggtg atggtggagt aaagcttatg agtgatgccc tgcaacatgc acaatgtact   2640

ctgaagagcc ttgtgctgag gcgttgccat ttcacttcac ttagcagtga atatctgtca   2700

acttctcttc tacacaacaa gagcctgacg catctggatc taggatcaaa ctggctacaa   2760

gacaatggag tgaagcttct gtgtgatgtc tttcggcatc caagctgtaa tcttcaggac   2820

ttggaattga tgggctgtgt tctcactaat gcatgttgtc tggatctggc ttctgttatt   2880

ttgaataacc caaacctgag gagcctggac cttgggaaca acgatttgca ggatgatgga   2940

gtgaaaattc tgtgtgatgc tttgagatat ccaaactgta acattcagag gctcgggttg   3000

gaatactgtg gtttgacatc tctctgctgt caagatctct cctctgctct tatctgcaac   3060

aaaagactga taaaaatgaa tctgacacag aataccttag gatatgaagg aattgtgaag   3120

ttatataaag tcttgaagtc tcctaagtgt aaactacaag ttctagggtt gtgcaaagag   3180

gcatttgatg aggaagccca gaagctgctg gaagctgtgg gagttagcaa tccacactta   3240

atcattaagc cagattgtaa ctatcataat gaagaagatg tgtcttggtg gtggtgtttc   3300

tgatttgaag aaactgacat tcctttaaaa atataaatat aaatacatac atacatagat   3360

atatacccag acttgggtgc ttagcttcag atactctatg cccagagata gtgcacttgg   3420

cagctgtcag ataccattca tctacttctc tgtaaaatgt ctgttctact tcacacagtg   3480

gtcgagaggc taaaataaaa tgaaaagcat aaaactctct g                       3521


<210> SEQ ID NO 3
<211> LENGTH: 3484
<212> TYPE: DNA
<213> ORGANISM: Homo sapiens

<400> SEQUENCE: 3

acacctcagt tcacaatcct ggggcgatat ggcagaatct ttttttcgg attttggctt      60

gttgtggtat ctgaaggagc tcagaaagga agagttttgg aaatttaagg agctcctcaa    120

acaacctttg gagaaatttg aactcaagcc aatcccctgg gctgagctga agaaggcctc    180

caaagaagat gtagcaaagc tgctggacaa acattaccca ggaaagcagg catgggaggt    240

aacactgaac ctgtttctac agatcaatag gaaagatctc tggacaaagg ctcaggaaga    300
```

-continued

```
gatgagaaat aagctaaacc catacagaaa gcatatgaag gaaacatttc aactcatatg    360
ggagaaggaa acctgtcttc acgtccctga gcatttctac aaagaaacca tgaaaaatga    420
gtataaagaa ttgaatgacg catatactgc tgcggctaga cgacacactg tggtcctgga    480
aggtcctgat ggaattggaa aaacaaccct tttaagaaaa gtgatgttgg actgggcaga    540
gggaaactta tggaaggaca ggttcacatt tgtgtttttc ctcaatgtct gtgaaatgaa    600
cggtatcgca gagaccagct tactggagct cctctctagg gactggccgg agtcttcaga    660
gaagatcgaa gacatttttt cccagccaga gagaattctg ttcatcatgg atggctttga    720
gcaactgaag tttaacttac aacttaaggc tgacttgagc gatgattgga ggcagcggca    780
gccaatgcca attatcctga gcagtttgtt gcaaaaaaag atgcttccag aatcctctct    840
ccttattgca ttaggaaaac tggctatgca aaaacactat tttatgttgc ggcatccaaa    900
actcataaag ctcttaggat tcagtgaatc tgaaaagaag tcgtatttct cctacttctt    960
tggtgagaag agcaaagccc tgaaagtctt caattttgtg agagataatg ggccgctgtt   1020
tatcttgtgc cataatccct ttacgtgctg gttggtctgt acttgtgtga aacagaggct   1080
agagagggga gaagaccttg aaataaactc ccaaaacacc acctatttat atgcatcctt   1140
tttaacaact gtattcaaag caggaagtca gagttttcca cctaaggtga acagagcccg   1200
actaaaaagc ctgtgtgctt tggctgcaga gggaatttgg acatatacat ttgtattttc   1260
ccatggggat ctccggagga atgggttatc tgagtctgag ggcgtgatgt gggtgggtat   1320
gagactcctc caaaggagag ggactgtttt tgccttcatg catctgtgta tccaagagtt   1380
ttgtgccgcc atgttttatt tgctcaaacg acccaaagac gatcctaacc cggccattgg   1440
aagcataacc cagcttgtaa gagcaagtgt ggttcagcct caaaccctct tgacccaggt   1500
ggggatattc atgtttggaa tttcaacaga agaaatcgtc agcatgctgg agacctcctt   1560
tggttttcca ctgtcaaaag acctaaagca ggaaataacc caatgccttg aaagtttaag   1620
tcaatgtgaa gctgataggg aagccatagc tttccaggaa ctattcattg gtttgtttga   1680
aactcaggaa aaagaatttg taaccaaagt gatgaatttc tttgaagaag ttttcattta   1740
tattggtaac atagaacatt tggtaatagc ttcattctgc ctgaagcatt gtcaacattt   1800
aacgacactt cgcatgtgtg tggagaatat ctttccagat gactcaggat gcatctcaga   1860
ttacaatgag aagctcgtct actggcggga gctttgctca atgttcatta ccaacaagaa   1920
cttccagatt ttagacatgg aaaataccag ccttgatgat ccctccctgg cgattctttg   1980
caaagcgctg gctcagcctg tttgtaaact ccgaaaactc atatttactt ctgtgtactt   2040
tggacatgat tcagaattat ttaaggcagt tcttcacaac cctcatctga aacttctgag   2100
cctgtacggc actagcctct cccagtctga catcagacac ctgtgtgaga cgctgaaaca   2160
tccaatgtgc aagatagaag agctgatact gggaaagtgt gacatctcca gtgaagtttg   2220
tgaagacatc gcctccgtcc tggcctgcaa cagcaagctg aaacacctct ccttggtaga   2280
aaatcccttg agggacgaag gaatgacgtt gctgtgtgaa gccctgaagc actcacactg   2340
tgccctggag aggctgatgt tgatgtactg ctgtctcacc tctgtctcct gtgactccat   2400
ttccgaagtc ctcttgtgca gtaagtccct gtccctcctc gatctgggct caaatgccct   2460
ggaagataat ggagtggcat ctctgtgtgc agcgctgaag cacccaggct gcagcatacg   2520
ggagctgtgg ttgatgggct gtttccttac ttccgattcc tgtaaggaca ttgctgctgt   2580
tcttatttgc aatgggaaac tgaagaccct gaaacttggg cataatgaaa taggagacac   2640
```

-continued

```
tggtgtcaga cagttatgtg cagctttgca gcatcctcac tgtaaattag agtgtctcgg   2700
gctgcaaacg tgtccgatca cccgtgcctg ctgcgacgac atcgccgcag cactcatcgc   2760
ctgcaaaaca ctgaggagcc tgaacctcga ctggattgcc ttggatgctg atgcagtggt   2820
ggtgctgtgt gaggcattga gccacccgga ctgtgccctg cagatgctgg ggctgcacaa   2880
atctggcttt gatgaagaaa ctcagaagat cctgatgtct gtggaagaaa aaattcccca   2940
tctgaccatt tcacatggac cttggattga cgaggaatac aagatcaggg gtgtgctcct   3000
ctgatgggga acaccctgaa gtagtcgtct cacaaaggct ttccttggcc acagtgggac   3060
cttcacctgg cacctctatc ctgtaattgc acatcatggc agcagggctg tgatttcaga   3120
ggtactccct aagtgttcta gcaatatgat tatggagtgt gattcagtgt acatgctgat   3180
tgtctttgcc tcggtcctat atccccttgt ctttagaaat cccatcctgc cttgtgatat   3240
ttagaagcac aagtacgtta aacaagtgct aaacgctctg gaaagcatgg ctttattttc   3300
ttaatggatg tcttggtgtg taggagcatg catttgtagg caccacaatc cggatacttc   3360
tgacacagaa gtgatgctag aatgtgtcta tagattgtat tgctagcatc cagactttct   3420
agtttgtcca gatttcgatt tgatcaattt tcttgtccaa taaaaaagca tttccaaatc   3480
tcta                                                                3484
```

<210> SEQ ID NO 4
<211> LENGTH: 1974
<212> TYPE: DNA
<213> ORGANISM: Homo sapiens

<400> SEQUENCE: 4

```
atcaccatgg ccatggccaa ggccagaaag ccccgggagg cattgctctg ggccttgagt     60
gaccttgagg agaacgattt caagaagtta aagttctact tacgggatat gaccctgtct    120
gagggccagc cccactggc cagaggggag ttggagggcc tgattccggt ggacctggca    180
gaattactga tttcaaagta tggagaaaag gaggctgtga aagttgtcct caagggcttg    240
aaggtcatga acctgttgga acttgtggac cagctcagcc atatttgtct gcatgattac    300
agagaagtat accgagagca tgtgcgctgc ctagaggaat ggcaggaagc aggagtcaat    360
ggcagataca accaggtgct cctggtggcc aagcccagct cagagagccc agaatcactt    420
gcctgcccct tcccggagca ggagctggag tctgtcacgg tggaggctct atttgattca    480
ggggaaaagc cctcactggc cccatcctta gttgtgctac aggggtcggc tggcactgga    540
aagacaactc tcgccagaaa aatggtgttg gactgggcca ccggtactct gtacccaggc    600
cggtttgatt atgtctttta tgtaagctgc aaagaagtgg tcctgctgct ggagagcaaa    660
ctggagcagc tccttttctg gtgctgcggg gacaatcaag cccctgtcac agagattctg    720
aggcagccag agcggctcct gttcatcctg gatggctttg atgagctgca gaggcccttt    780
gaagaaaagt tgaagaagag gggtttgagt cccaaggaga gcctgctgca ccttctaatt    840
aggagacata cactccccac gtgctccctt ctcatcacca cccggcccct ggctttgagg    900
aatctggagc ccttgctgaa acaagcacgt catgtccata tcctaggctt ctctgaggag    960
gagagggcga ggtacttcag ctcctatttc acggatgaga agcaagctga ccgtgccttc   1020
gacattgtac agaaaaatga cattctctac aaagcgtgtc aggttccagg catttgctgg   1080
gtggtctgct cctggctgca ggggcagatg gagagaggca aagttgtctt agagacacct   1140
agaaacagca ctgacatctt catggcttac gtctccacct ttctgccgcc cgatgatgat   1200
gggggctgct ccgagctttc ccggcacagg gtcctgagga gtctgtgctc cctagcagct   1260
```

```
gaagggattc agcaccagag gttcctattt gaagaagctg agctcaggaa acataattta   1320

gatggcccca ggcttgccgc tttcctgagt agtaacgact accaattggg acttgccatc   1380

aagaagttct acagcttccg ccacatcagc ttccaggact tttttcatgc catgtcttac   1440

ctggtgaaag aggaccaaag ccggctgggg aaggagtccc gcagagaagt gcaaaggctg   1500

ctggaggtaa aggagcagga agggaatgat gagatgaccc tcactatgca gtttttactg   1560

gacatctcga aaaaagacag cttctcgaac ttggagctca agttctgctt cagaatttct   1620

ccctgtttag cgcaggatct gaagcatttt aaagaacaga tggaatctat gaagcacaac   1680

aggacctggg atttggaatt ctccctgtat gaagctaaaa taaagaatct ggtaaaaggt   1740

attcagatga acaatgtatc attcaagata aaacattcaa atgaaaagaa atcacagagc   1800

cagaatttat tttctgtcaa aagcagcttg agtcatggac ctaaggagga gcaaaaatgt   1860

ccttctgtcc atggacagaa ggagggcaaa gataatatag caggaacaca aaaggaagct   1920

tctactggaa aaggcagagg gacagaggaa acaccaaaaa atacttacat ataa         1974
```

<210> SEQ ID NO 5
<211> LENGTH: 3525
<212> TYPE: DNA
<213> ORGANISM: Homo sapiens

<400> SEQUENCE: 5

```
gctctgacct tctttcccag gatgaggtgg ggccaccatt tgcccagggc ctcttggggc     60

tctggtttta gaagagcact ccagcgacca gatgatcgta tccccttcct gatccactgg    120

agttggcccc ttcaagggga gcgtcccttt gggcccccta gggcctttat acgccaccac    180

ggaagctcgg tagatagcgc tcccccatcc gggaggcatg gacggctgtt ccccagcgcc    240

tctgcaactg aagctataca gcggcaccgc cggaacctgg ctgagtggtt cagccggctg    300

cccagggagg agcgccagtt tggcccaacc tttgccctag acacggtcca cgttgaccct    360

gtgatccgcg agagtacccc tgatgagcta cttcgcccac ccgcggagct ggccctggag    420

catcagccac cccaggccgg gctcccccca ctggccttgt ctcagctctt taacccggat    480

gcctgtgggc gccgggtgca gacagtggtg ctgtatggga cagtgggcac aggcaagagc    540

acgctggtgc gcaagatggt tctggactgg tgttatgggc ggctgccggc cttcgagctg    600

ctcatcccct tctcctgtga ggacctgtca tccctgggcc ctgccccagc ctccctgtgc    660

caacttgtgg cccagcgcta cacgcccctg aaggaggttc tgcccctgat ggctgctgct    720

gggtcccacc tcctctttgt gctccatggc ttagagcatc tcaacctcga cttccggctg    780

gcaggcacgg gactttgtag tgacccggag gaaccgcagg aaccagctgc tatcatcgtc    840

aacctgctgc gcaaatacat gctgcctcag gccagcattc tggtgaccac tcggccctct    900

gccattggcc gtatccccag caagtacgtg ggccgctatg gtgagatctg cggtttctct    960

gataccaacc tgcagaagct ctacttccag ctccgcctca accagccgta ctgcgggtat   1020

gccgttggcg gttcaggtgt ctctgccaca ccagctcagc gtgaccacct ggtgcagatg   1080

ctctcccgga acctggaggg gcaccaccag atagccgctg cctgcttcct gccgtcctat   1140

tgctggctcg tttgtgccac cttgcacttc ctgcatgccc ccacgcctgc tgggcagacc   1200

cttacaagca tctataccag cttcctgcgc ctcaacttca gcggggaaac cctggacagc   1260

actgacccct ccaatttgtc cctgatggcc tatgcagccc gaaccatggg caagttggcc   1320

tatgaggggg tgtcctcccg caagacctac ttctctgaag aggatgtctg tggctgcctg   1380
```

-continued

```
gaggctggca tcaggacgga ggaggagttt cagctgctgc acatcttccg tcgggatgcc   1440
ctgaggtttt tcctggcccc atgtgtggag ccagggcgtg caggcacctt cgtgttcacc   1500
gtgcccgcca tgcaggaata cctggctgcc ctctacattg tgctgggttt gcgcaagacg   1560
accctgcaaa aggtgggcaa ggaagtggct gagctcgtgg gccgtgttgg ggaggacgtc   1620
agcctggtac tgggcatcat ggccaagctg ctgcctctgc gggctctgcc tctgctcttc   1680
aacctgatca aggtggttcc acgagtgttt gggcgcatgg tgggtaaaag ccgggaggcg   1740
gtggctcagg ccatggtgct ggagatgttt cgagaggagg actactacaa cgatgatgtt   1800
ctggaccaga tgggcgccag tatcctgggc gtggagggcc cccggcgcca cccagatgag   1860
ccccctgagg atgaagtctt cgagctcttc cccatgttca tgggggggct tctctctgcc   1920
cacaaccgag ctgtgctagc tcagcttggc tgccccatca agaacctgga tgccctggag   1980
aatgcccagg ccatcaagaa gaagctgggc aagctgggcc ggcaggtgct gcccccatca   2040
gagctccttg accacctctt cttccactat gagttccaga accagcgctt ctccgctgag   2100
gtgctcagct ccctgcgtca gctcaacctg gcaggtgtgc gcatgacacc agtcaagtgc   2160
acagtggtgg cagctgtgct gggcagcgga aggcatgccc tggatgaggt gaacttggcc   2220
tcctgccagc tagatcctgc tgggctgcgc acactcctgc ctgtcttcct gcgtgcccgg   2280
aagctgggct tgcaactcaa cagcctgggc cctgaggcct gcaaggacct ccgagacctg   2340
ttgctgcatg accagtgcca aattaccaca ctgcggctgt ccaacaaccc gctgacggag   2400
gcaggtgttg ccgtgctaat ggaggggctg gcaggaaaca cctcagtgac gcacctgtcc   2460
ctgctgcaca cgggccttgg ggacgaaggc ctggagctgc tggctgccca gctggaccgc   2520
aaccggcagc tgcaggagct gaacgtggcg tacaacggtg ctggtgacac agcggccctg   2580
gccctggcca gagctgcccg ggagcaccct tccctggaac tgctacacct ctacttcaat   2640
gagctgagct cagagggccg ccaggtcttg cgagacttgg ggggtgctgc tgaaggtggt   2700
gcccgggtgg tggtgtcact gacagagggg acggcggtgt cagaatactg gtcagtgatc   2760
ctcagtgaag tccagcggaa cctcaatagc tgggatcggg cccgggttca gcgacacctt   2820
gagctcctac tgcgggatct ggaagatagc cggggtgcca cccttaatcc ttggcgcaag   2880
gcccagctgc tgcgagtgga gggcgaggtc agggccctcc tggagcagct gggaagctct   2940
ggaagctgag acactggcgg caggcaccta gctatgtgac cactggccct aaaccttttc   3000
cctctgtggc ctcctggctt gcactgctcc ctctagaaag attccttcag gtctggaggc   3060
agaggaatgg gcatagctga gccagttgcc ctcctagggc atgtttgacc aggactgagt   3120
ctggaatctc caagttaaag atggtgaatc aatgcttcgg gcttggagat ggaacatgcc   3180
tcctctccat tcagctagaa ggaccaaagc atgtggcatt tggatggcca gagtgccctg   3240
aagcaccact accaaccttg cctccccctc ctctcaaaga gcctctgatt gtgtcaccaa   3300
ggggctcaca tcttatgtct gccatgccag ggtgtcgcc atccagatgt gttggaagct   3360
tcccctcctg ccttatgctc acctgtggac accgaggatg ccctcacatt ggtgctttct   3420
cctcatcctc atgccccctt tgccacaatg gtatgatggc ttggtagccc ctcgaggcag   3480
atgcacctga cttgctgcta ttaaaaagcc gtgtgccttc tacca                     3525
```

<210> SEQ ID NO 6
<211> LENGTH: 3373
<212> TYPE: DNA
<213> ORGANISM: Homo sapiens

<400> SEQUENCE: 6

-continued

```
ttcttcagcc ttaacctaag gtctcatact cggagcacta tgacatcgcc ccagctagag     60
tggactctgc agacccttct ggagcagctg aacgaggatg aattaaagag tttcaaatcc    120
cttttatggg cttttcccct cgaagacgtg ctacagaaga ccccatggtc tgaggtggaa    180
gaggctgatg gcgagaaact ggcagaaatt ctggtcaaca cctcctcaga aaattggata    240
aggaatgcga ctgtgaacat cttggaagag atgaatctca cggaattgtg taagatggca    300
aaggctgaga tgatggagga cggacaggtg caagaaatag ataatcctga gctgggagat    360
gcagaagaag actcggagtt agcaaagcca ggtgaaaagg aaggatggag aaattcaatg    420
gagaaacagt ctttggtctg gaagaacacc ttttggcaag gagacattga caatttccat    480
gacgacgtca ctctgagaaa ccaacggttc attccattct tgaatcccag aacacccagg    540
aagctaacac cttacacggt ggtgctgcac ggccccgcag gcgtggggaa aaccacgctg    600
gccaaaaagt gtatgctgga ctggacagac tgcaacctca gcccgacgct cagatacgcg    660
ttctacctca gctgcaagga gctcagccgc atgggcccct gcagttttgc agagctgatc    720
tccaaagact ggcctgaatt gcaggatgac attccaagca tcctagccca agcacagaga    780
atcctgttcg tggtcgatgg ccttgatgag ctgaaagtcc cacctggggc gctgatccag    840
gacatctgcg gggactggga gaagaagaag ccggtgcccg tcctcctggg gagtttgctg    900
aagaggaaga tgttacccag ggcagccttg ctggtcacca cgcggcccag ggcactgagg    960
gacctccagc tcctggcgca gcagccgatc tacgtaaggg tggagggctt cctggaggag   1020
gacaggaggg cctatttcct gagacacttt ggagacgagg accaagccat gcgtgccttt   1080
gagctaatga ggagcaacgc ggccctgttc cagctgggct cggcccccgc ggtgtgctgg   1140
attgtgtgca cgactctgaa gctgcagatg gagaaggggg aggacccggt ccccacctgc   1200
ctcacccgca cggggctgtt cctgcgtttc ctctgcagcc ggttcccgca gggcgcacag   1260
ctgcggggcg cgctgcggac gctgagcctc ctggccgcgc agggcctgtg ggcgcagatg   1320
tccgtgttcc accgagagga cctggaaagg ctcggggtgc aggagtccga cctccgtctg   1380
ttcctggacg gagacatcct ccgccaggac agagtctcca aaggctgcta ctccttcatc   1440
cacctcagct tccagcagtt tctcactgcc ctgttctacg ccctggagaa ggaggagggg   1500
gaggacaggg acggccacgc ctgggacatc ggggacgtac agaagctgct ttccggagaa   1560
gaaagactca agaaccccga cctgattcaa gtaggacact tcttattcgg cctcgctaac   1620
gagaagagag ccaaggagtt ggaggccact tttggctgcc ggatgtcacc ggacatcaaa   1680
caggaattgc tgcaatgcaa agcacatctt catgcaaata agcccttatc cgtgaccgac   1740
ctgaaggagg tcttgggctg cctgtatgag tctcaggagg aggagctggc gaaggtggtg   1800
gtggccccgt tcaaggaaat ttctattcac ctgacaaata cttctgaagt gatgcattgt   1860
tccttcagcc tgaagcattg tcaagacttg cagaaactct cactgcaggt agcaaagggg   1920
gtgttcctgg agaattacat ggattttgaa ctggacattg aatttgaaag ctcaaacagc   1980
aacctcaagt ttctggaagt gaaacaaagc ttcctgagtg actcttctgt gcggattctt   2040
tgtgaccacg taacccgtag cacctgtcat ctgcagaaag tggagattaa aaacgtcacc   2100
cctgacaccg cgtaccggga cttctgtctt gctttcattg ggaagaagac cctcacgcac   2160
ctgaccctgg cagggcacat cgagtgggaa cgcacgatga tgctgatgct gtgtgacctg   2220
ctcagaaatc ataaatgcaa cctgcagtac ctgaggttgg gaggtcactg tgccaccccg   2280
gagcagtggg ctgaattctt ctatgtcctc aaagccaacc agtccctgaa gcacctgcgt   2340
```

-continued

```
ctctcagcca atgtgctcct ggatgagggt gccatgttgc tgtacaagac catgacacgc   2400

ccaaaacact tcctgcagat gttgtcgttg gaaaactgtc gtcttacaga agccagttgc   2460

aaggaccttg ctgctgtctt ggttgtcagc aagaagctga cacacctgtg cttggccaag   2520

aaccccattg ggatacaggg ggtgaagttt ctgtgtgagg gcttgagtta ccctgattgt   2580

aaactgcaga ccttggtgtt acagcaatgc agcataacca agcttggctg tagatatctc   2640

tcagaggcgc tccaagaagc ctgcagcctc acaaacctgg acttgagtat caaccagata   2700

gctcgtggat tgtggattct ctgtcaggcg ttagagaatc caaactgtaa cctaaaacac   2760

ctacgcctct ggagctgctc cctcatgcct ttctattgtc agcatcttgg atctgctctc   2820

ctcagcaatc agaagcttga aactctggac ctgggccaga atcatttgtg gaagagtggc   2880

ataattaagc tctttggggt tctaagacaa agaactggat ccttgaagat actcaggttg   2940

aagacctatg aaactaattt ggaaatcaag aagctgttgg aggaagtgaa agaaaagaat   3000

cccaagctga ctattgattg caatgcttcc ggggcaacgg cacctccgtg ctgtgacttt   3060

ttttgctgag cagcctggga tcgctctacg aattacacag gaagcgggat tcgggtctct   3120

aagatgtctt atgaatgcag gtcagagggt cacatgttaa cactagagtc tgtcgagagg   3180

taggatttga cactggtttt ctcactattt ttgggagatt ctgcacgagt cacgcacccc   3240

cttcacatga cgctatgtac tttctcacag ggataataaa gttagagcac tctcgttgca   3300

gctgcgttta ttgacatgct caggagcaaa cctgcaataa acatggtact ctgtgcttcg   3360

tctaggagga agt                                                      3373
```

<210> SEQ ID NO 7
<211> LENGTH: 3540
<212> TYPE: DNA
<213> ORGANISM: Homo sapiens

<400> SEQUENCE: 7

```
tgagaaactg catgtgttgg gcaagatgaa cttttctgta atcacctgcc ccaacggtgg     60

taccaaccaa gggcttctgc cttacctgat ggccctggat cagtatcagc tggaggaatt    120

caagctttgc ttggaacccc agcagctgat ggacttctgg tcggcccccc aggggcactt    180

cccgcgtatc ccctgggcaa acttgagagc tgccgacccct ttgaatctgt cctttctttt   240

ggatgaacac ttcccaaaag gtcaggcatg gaaagtggtc ctcggcatct tccagacaat    300

gaatctgacc tcactgtgtg agaaagttag agccgagatg aaagagaatg tgcagaccca    360

agagctgcaa gatccaaccc aggaagatct agagatgcta gaagcagcag cagggaatat    420

gcagacccag ggatgccaag atccaaacca agaagaacta gacgagctag aagaagaaac    480

agggaatgta caggcccagg gatgccaaga tccaaaccaa gaagaaccag agatgctaga    540

ggaagcagac cacagaagaa aatacagaga gaacatgaag gctgaactac tggagacatg    600

ggacaacatc agttggccta aagaccacgt atatatccgt aatacatcaa aggacgaaca    660

tgaggaactg cagcgcctac tggatcctaa taggactaga gcccaggccc agacgatagt    720

cttggtgggg agggcagggg ttgggaagac caccttggca atgcaggcta tgctgcactg    780

ggcaaatgga gttctctttc agcaaaggtt ctcctatgtt ttctatctca gctgccataa    840

aataaggtac atgaaggaaa ctacctttgc tgaattgatt tctttggatt ggcccgattt    900

tgatgccccc attgaagagt tcatgtctca accagagaag ctcctgttta ttattgatgg    960

ctttgaggaa ataatcatat ctgagtcacg ctctgagagc ttggatgatg gctcgccatg   1020

tacagactgg taccaggagc tcccagtgac caaaatccta cacagcttgt tgaagaaaga   1080
```

-continued

```
attggttccc ctggctacct tactgatcac gatcaagacc tggtttgtga gagatcttaa   1140
ggcctcatta gtgaatccat gctttgtaca aattacaggg ttcacagggg acgacctacg   1200
ggtatatttc atgagacact ttgatgactc aagtgaagtt gagaaaatcc tgcagcagct   1260
aagaaaaaac gaaactctct ttcattcctg cagtgccccc atggtgtgtt ggaccgtatg   1320
ttcctgtctg aagcagccga aggtgaggta ttacgatctc cagtcaatca ctcagactac   1380
caccagtctg tatgcctatt ttttctccaa cttgttctcc acagcagagg tagatttggc   1440
agatgacagc tggccaggac aatggagggc cctctgcagt ctggccatag aagggctgtg   1500
gtctatgaac ttcacgttta acaaagaaga cactgagatc gagggcctgg aagtgccttt   1560
cattgattct ctctacgagt tcaatattct tcaaaagatc aatgactgtg gggttgcac    1620
tactttcacc cacctaagtt tccaggagtt ttttgcagcc atgtcctttg tgctagagga   1680
acctagagaa ttccctcccc attccacaaa gccacaagag atgaagatgt tactgcaaca   1740
cgtcttgctt gacaaagaag cctactggac tccagtggtt ctgttcttct ttggtctttt   1800
aaataaaaac atagcaagag aactggaaga tactttgcat tgtaaaatat ctcccagggt   1860
aatggaggaa ttattaaagt ggggagaaga gttaggtaag gctgaaagtg cctctctcca   1920
atttcacatt ctacgacttt ttcactgcct acacgagtcc caggaggaag acttcacaaa   1980
gaagatgttg ggtcgtatct ttgaagttga ccttaatatt ttggaggacg aagaactcca   2040
agcttcttca ttttgcctaa agcactgtaa aaggttaaat aagctaaggc tttctgttag   2100
cagtcacatc cttgaaaggg acttggaaat tctggagaca agcaagtttg attccaggat   2160
gcacgcatgg aacagcattt gctctacgtt ggtcacaaat gagaatctgc atgagctaga   2220
cctgagtaac agcaaacttc atgcttcctc tgtgaagggt ctctgtcttg cactgaaaaa   2280
tccaagatgc aaagtccaga aactgacgtg caaatcggta actcctgagt gggttctgca   2340
ggacctcatt attgcccttc agggtaacag caagctgacc catctgaact tcagctctaa   2400
caagctggga atgactgtcc ccctgattct taaagctttg agacactcag cttgcaacct   2460
caagtatctg tgcctggaga aatgcaactt gtcggcagcc agctgtcagg acctagcctt   2520
gtttctcacc agcatccaac acgtaactcg attgtgcctg ggatttaatc ggctccaaga   2580
tgatggcata aagctattgt gtgcggccct gactcacccc aagtgtgcct tagagagact   2640
ggagctctgg ttttgccagc tggcagcacc cgcttgcaag cacttgtcag atgctctcct   2700
gcagaacagg agcctgacac acctgaatct gagcaagaac agcctgagag acgagggagt   2760
caagttcctg tgtgaggcct tgggtcgccc agatggtaac ctgcagagcc tgaatttgtc   2820
aggttgttct ttcacaagag agggctgtgg agagctggct aatgccctca gccataatca   2880
taatgtgaaa atcttagatt tgggagaaaa tgatcttcag gatgatggag tgaagctact   2940
gtgtgaggct ctgaaaccac atcgtgcatt gcacacactt gggttggcga aatgcaatct   3000
gacaactgct tgctgccagc atctcttctc tgttctcagc agcagtaaga gcctggtcaa   3060
tctgaacctt ctaggcaatg aattggatac tgatggtgtc aagatgctat gcttcaaaaa   3120
gacctgcaca atgtagtgag agaggagata cagacctcac agaaggagct ctgtctgaaa   3180
ctcaagtgtg cgtgggattt taatgacctt gaagacaagt ggtggtggtg atcccacgga   3240
ttagatgcca cgtggcttga ccatggatct tgggggaaag ccaccaggac atcctggcct   3300
gtgtgtcgct ccaatgtcac catttgtggg gacaaatgag ctgttccctg caggaggctt   3360
tgtcacggtt gttggaggcc gcccattgca cgcccaggtc tggaatccta gtgtaatact   3420
```

-continued

```
gtgtctggta ccaagatcat aagttggctg tgccttcagt cttgtctatg tcctccttgg   3480

tgtaatgttt ttaattcttg gaggtgttga gagaattcaa taaagcaaag catataaaaa   3540
```

<210> SEQ ID NO 8
<211> LENGTH: 3934
<212> TYPE: DNA
<213> ORGANISM: Homo sapiens

<400> SEQUENCE: 8

```
gtctcgtgtt tctctcttcc aatcggttgt ctttatcgtg gacactgagg tgttctctgc     60

cttgactaaa gatgagtgac gtgaatccac cctctgacac ccccattccc ttttcatcct    120

cctccactca cagttctcat attccgccct ggacattctc ttgctacccc ggctccccat    180

gtgaaaatgg ggtcatgctg tacatgagaa acgtgagcca tgaggagcta caacggttca    240

agcagctctt actgactgag ctcagtactg gcaccatgcc catcacctgg gaccaggtcg    300

agacagccag ctgggcagag gtggttcatc tcttgataga gcgtttccct ggacgacgcg    360

cttgggatgt gacttcgaac atctttgcca ttatgaactg tgataaaatg tgtgttgtag    420

tccgcagaga gataaatgcc attctgccta ccttggaacc agaggacttg aatgtgggag    480

aaacacaggt gaatctggag gaaggagaat ctggtaaaat acggcggtat aaatcgaatg    540

tgatggaaaa gtttttcccc atatgggaca ttacgacttg gcctggaaac cagagggact    600

tcttctacca aggtgtacac aggcacgagg agtacttacc atgtctgctt ctgcccaaaa    660

gaccccaggg tagacagccc aagaccgtgg ccatacaggg agctcctggg atcggaaaaa    720

caatcctggc caaaaaggtg atgtttgagt gggccagaaa caagttctac gcccacaagc    780

gctggtgtgc tttctacttc cattgccaag aggtgaacca gacgacagac cagagcttct    840

ccgagctgat tgagcaaaag tggcctggat ctcaggacct cgtgtcaaag attatgtcca    900

aacccgacca acttctgctg ctcttggatg gctttgagga gctcacatct accctcattg    960

acagactgga ggacctgagt gaagactgga ggcagaaatt gcctgggtct gtcctactga   1020

gcagtttgct gagcaaaacg atgcttccag aggccacgct actgatcatg ataagattta   1080

cctcttggca gacatgcaag cccttgctga aatgtccctc tctcgtaacc cttccggggt   1140

ttaatacgat ggaaaaaatc aagtatttcc agatgtattt tggacacaca gaggagggag   1200

accaagtctt gagtttcgcc atggaaaaca ccattctctt ctccatgtgc cgggtccctg   1260

tggtttgctg gatggtctgc tctggtctga aacagcaaat ggagagagga aacaatctca   1320

cacagtcatg tccaaatgcc acctctgtgt tcgtccggta tatttctagc ttgtttccca   1380

ccagagctga gaacttttcc agaaagatcc accaagcaca actggaaggt ctgtgtcact   1440

tggccgcaga cagcatgtgg cacaggaaat gggtgttagg taaagaagat cttgaggaag   1500

ccaagctgga tcagacggga gtcaccgcct tccttggcat gagtattctt cggagaattg   1560

caggtgagga agaccactat gtctttaccc tcgtgacttt tcaggaattt tttgcggcct   1620

tgttttatgt tctctgtttc ccacaaagac tcaaaaattt tcatgtgttg agccacgtga   1680

atatccagcg cctgatagcg agtcccagag gaagcaaaag ctatctctct cacatgggac   1740

ttttcttatt cggttttctg aacgaggcct gcgcttcggc cgtggaacag tcattccaat   1800

gcaaggtgtc tttcggtaat aagaggaaac tgctgaaagt catacctctg ttgcataaat   1860

gtgacccacc ttctccgggc agtggggtcc cgcagttatt ctactgtctg catgaaatcc   1920

gggaggaagc ctttgtaagc caagccctaa atgattatca taaagttgtc ttgagaattg   1980

gcaacaacaa agaagttcaa gtgtctgctt tttgcctgaa gcggtgtcaa tatttgcatg   2040
```

-continued

```
aggtggaact gaccgtcacc ctgaacttca tgaacgtgtg gaagctcagc tccagctccc   2100
atcctggctc tgaagcgcca gagagcaatg ggctgcatcg ttggtggcaa gacttatgct   2160
ctgtgtttgc aacgaatgat aagctggaag tcctgactat gaccaacagt gttttggggc   2220
ctcctttttt gaaggctctc gcggccgcac tgaggcaccc tcagtgcaaa ctgcaaaagc   2280
tactcctaag gcgtgtgaat agcaccatgt tgaaccagga cttaatcggt gttttgacgg   2340
ggaaccagca tctgagatac ttggaaatac aacatgtgga agtggagtcc aaagctgtga   2400
agcttctatg cagggtgctg agatcccccc ggtgccgtct gcagtgtctc aggttggaag   2460
actgcttggc cacccctaga atttggactg atcttggcaa taatcttcaa ggtaacgggc   2520
atctaaagac tctcatacta agaaaaaact ccctggagaa ctgtggggcg tattacctgt   2580
ctgtggccca gctggagagg ctgtcgatag agaactgcaa ccttacacag cttacttgtg   2640
aaagccttgc ctcctgtctc aggcagagta agatgctgac ccacctgagc ttggcagaaa   2700
acgccttgaa agatgaaggg gccaagcata tttggaatgc cctgccacac ctgagatgtc   2760
ctctgcagag gctggtactg agaaagtgtg acttgacctt taattgctgt caggatatga   2820
tctctgcgct ctgtaaaaat aaaaccctga aaagtcttga cctaagtttt aatagcctga   2880
aggatgatgg ggtgatcctg ctgtgtgagg ccctgaagaa ccctgactgt acattacaga   2940
tcctggagct ggaaaactgc ctgttcacct ccatctgctg ccaggccatg gcttccatgc   3000
tccgcaaaaa ccaacatctg agacatctgg acttgagcaa gaatgcgatt ggagtctatg   3060
gtattctgac cttgtgcgag gccttctcaa gccaaaagaa gagagaagag gtcattttct   3120
gtattcctgc ctggactcga ataactagct tctccccaac tcctcaccca cccgacttca   3180
cgggaaaaag tgactgccta tcccagatta atccttaggc cgtccagtca tctttctctg   3240
gggcttgatt gatcagttcc cactctgaca actggcaaat accaggcgtt atcatcctgt   3300
atgcattaac gtactttccc ctgaaacaga gcaacccagt caacaccaca gaacctcagc   3360
tttgaaccct ggagtgagga cggtgatgcc ctgtgtgtat taatatgcta tgtaaggctg   3420
ggcgtggtgg ctcacgcctg taacccagca ctatgggagg tcgaggtggg cagattacct   3480
gaggtcagga gttccagacc agcctggcca acatggtgaa accccgcctc tactaaaaaa   3540
aaaaatacaa aaaattaggc gtggtggtgg gctcctgtaa tcccagctgc tcgggaggct   3600
gaggcaggag aatcacttga atctaggagg cagagtttgc agtgagctga gatcacgcca   3660
ttgcactcca gcctgggcga cagagcaaga ctctgtctca agaagaaaaa aaaaatacat   3720
atacacataa atatatatat gtgtgtgtgt atatatatat atatatatat atatgctata   3780
taaagtttaa atgaaatgct ttgagtcacc taagacagga tatagacaaa gtcttcatcg   3840
tcttcttgct tcttctacct ttatttattc tcagctctga atgtatgaac ctgctcaatc   3900
acctcatctt aaaaataaaa tcactgtccc taga                               3934
```

```
<210> SEQ ID NO 9
<211> LENGTH: 3102
<212> TYPE: DNA
<213> ORGANISM: Homo sapiens

<400> SEQUENCE: 9

atggcagaat cggattctac tgactttgac ctgctgtggt atctagagaa tctcagtgac     60
aaggaatttc agagttttaa gaagtatctg gcacgcaaga ttcttgattt caaactgcca    120
cagtttccac tgatacagat gacaaaagaa gaactggcta acgtgttgcc aatctcttat    180
```

-continued

```
gagggacagt atatatggaa tatgctcttc agcatatttt caatgatgcg taaggaagat    240

ctttgtagga agatcattgg cagacgaaac cgcaatcagg aggcatgcaa agctgtcatg    300

aggagaaaat tcatgctgca atgggaaagt cacacttttg gaaaatttca ttataaattt    360

tttcgtgacg tttcgtcaga tgtgttctac atacttcaat tagcctatga ttctaccagc    420

tattattcag caaacaatct caatgtgttc ctgatgggag agagagcatc tggaaaaact    480

attgttataa atctggctgt gttgaggtgg atcaagggtg agatgtggca gaacatgatc    540

tcgtacgtcg ttcacctcac ttctcacgaa ataaaccaga tgaccaacag cagcttggct    600

gagctaatcg ccaaggactg gcctgacggc caggctccca ttgcagacat cctgtctgat    660

cccaagaaac tccttttcat cctcgaggac ttggacaaca taagattcga gttaaatgtc    720

aatgaaagtg ctttgtgtag taacagcacc cagaaagttc ccattccagt tctcctggtc    780

agtttgctga agagaaaaat ggctccaggc tgctggttcc tcatctcctc aaggcccaca    840

cgtgggaata atgtaaaaac gttcttgaaa gaggtagatt gctgcacgac cttgcagctg    900

tcgaatggga agagggagat atattttaac tctttcttta aagaccgcca gagggcgtcg    960

gcagccctcc agcttgtaca tgaggatgaa atactcgtgg gtctgtgccg agtcgccatc   1020

ttatgctgga tcacgtgtac tgtcctgaag cggcagatgg acaaggggcg tgacttccag   1080

ctctgctgcc aaacacccac tgatctacat gcccactttc ttgctgatgc gttgacatca   1140

gaggctggac ttactgccaa tcagtatcac ctaggtctcc taaaacgtct gtgtttgctg   1200

gctgcaggag gactgtttct gagcaccctg aatttcagtg gtgaagacct cagatgtgtt   1260

gggtttactg aggctgatgt ctctgtgttg caggccgcga atattctttt gccgagcaac   1320

actcataaag accgttacaa gttcatacac ttgaacgtcc aggagttttg tacagccatt   1380

gcatttctga tggcagtacc caactatctg atcccctcag gcagcagaga gtataaagag   1440

aagagagaac aatactctga ctttaatcaa gtgtttactt tcatttttgg tcttctaaat   1500

gcaaacagga gaaagattct tgagacatcc tttggatacc agctaccgat ggtagacagc   1560

ttcaagtggt actcggtggg atacatgaaa catttggacc gtgacccgga aaagttgacg   1620

caccatatgc ctttgtttta ctgtctctat gagaatcggg aagaagaatt tgtgaagacg   1680

attgtggatg ctctcatgga ggttacagtt taccttcaat cagacaagga tatgatggtc   1740

tcattatact gtctggatta ctgctgtcac ctgaggacac ttaagttgag cgttcagcgc   1800

atctttcaaa acaaagagcc acttataagg ccaactgcta gtcaaatgaa gagccttgtc   1860

tactggagag agatctgctc tctttttat acaatggaga gcctccggga gctgcatatc   1920

tttgacaatg accttaatgg tatttcagaa aggattctgt ctaaagccct ggagcattct   1980

agctgtaaac ttcgcacact caagttgtcc tatgtctcga ctgcttctgg ttttgaagac   2040

ttactcaagg ctttggctcg taatcggagc ctgacatacc tgagtatcaa ctgtacgtcc   2100

atttccctaa atatgttttc acttctgcat gacatcctgc acgagcccac atgccaaata   2160

agtcatctga gcttgatgaa atgtgatttg cgagccagcg aatgcgaaga aatcgcctct   2220

ctcctcatca gtggcgggag tctgagaaaa ctgaccttat ccagcaatcc gctgaggagc   2280

gacgggatga acatactgtg tgatgccttg cttcatccca actgcactct tatatcactg   2340

gtgttagtct tctgctgtct cactgaaaat tgctgcagcg cccttggaag agtgcttctg   2400

ttcagcccaa ctctaagaca actagacctg tgtgtgaatc gcttaaaaaa ttacggagtg   2460

ttgcatgtga cgtttccctt gctgtttcca acctgtcagt tagaggagct tcatctgtct   2520

ggctgtttct ttagcagcga tatctgtcaa tatattgcca tagttattgc tactaatgaa   2580
```

```
aaactgagga gcctggagat tgggagcaac aaaatagaag atgcaggaat gcagctgcta   2640

tgtggtggtt tgagacatcc caactgcatg ttggtgaata ttgggctaga agagtgcatg   2700

ttaaccagtg cctgctgtcg atctcttgcc tctgttctta ccaccaacaa aacactagaa   2760

agactcaact tgcttcaaaa tcacttgggc aatgatggag ttgcaaaact tcttgagagc   2820

ttgatcagcc cagattgtgt acttaaggta gttgggcttc cattaactgg cctgaacaca   2880

caaacccagc agttgctgat gactgtaaag gaaagaaaac ccagtttgat ctttctgtct   2940

gaaacttggt ctttaaagga aggcagagaa attggtgtga cacctgcttc tcagccaggt   3000

tcaataatac ctaattctaa tttggattac atgtttttca aatttcccag aatgtctgca   3060

gccatgagaa cgtcaaatac agcatctagg caaccccttt ga                      3102
```

<210> SEQ ID NO 10
<211> LENGTH: 2928
<212> TYPE: DNA
<213> ORGANISM: Homo sapiens

<400> SEQUENCE: 10

```
atgaggtggg gccaccattt gcccagggcc tcttggggct ctggttttag aagagcactc     60

cagcgaccag atgatcgtat ccccttcctg atccactgga gttggcccct tcaaggggag    120

cgtccctttg ggccccctag ggcctttata cgccaccacg gaagctcggt agatagcgct    180

cccccacccg ggaggcatgg acggctgttc cccagcgcct ctgcaactga agctatacag    240

cggcaccgcc ggaacctggc tgagtggttc agccggctgc ccagggagga gcgccagttt    300

ggcccaacct ttgccctaga cacggtccac gttgaccctg tgatccgcga gagtacccct    360

gatgagctac ttcgcccacc cgcggagctg gccctggagc atcagccacc ccaggccggg    420

ctcccccac tggccttgtc tcagctcttt aacccggatg cctgtgggcg ccgggtgcag     480

acagtggtgc tgtatgggac agtgggcaca ggcaagagca cgctggtgcg caagatggtt    540

ctggactggt gttatgggcg gctgccggcc ttcgagctgc tcatcccctt ctcctgtgag    600

gacctgtcat ccctgggccc tgccccagcc tccctgtgcc aacttgtggc ccagcgctac    660

acgcccctga aggaggttct gcccctgatg gctgctgctg ggtcccacct cctctttgtg    720

ctccatggct tagagcatct caacctcgac ttccggctgg caggcacggg actttgtagt    780

gacccggagg aaccgcagga accagctgct atcatcgtca acctgctgcg caaatacatg    840

ctgcctcagg ccagcattct ggtgaccact cggccctctg ccattggccg tatccccagc    900

aagtacgtgg gccgctatgg tgagatctgc ggtttctctg ataccaacct gcagaagctc    960

tacttccagc tccgcctcaa ccagccgtac tgcgggtatg ccgttggcgg ttcaggtgtc   1020

tctgccacac cagctcagcg tgaccacctg gtgcagatgc tctcccggaa cctggagggg   1080

caccaccaga tagccgctgc ctgcttcctg ccgtcctatt gctggctcgt ttgtgccacc   1140

ttgcacttcc tgcatgcccc cacgcctgct gggcagaccc ttacaagcat ctataccagc   1200

ttcctgcgcc tcaacttcag cggggaaacc ctggacagca ctgacccctc caatttgtcc   1260

ctgatggcct atgcagcccg aaccatgggc aagttggcct atgaggggt gtcctcccgc    1320

aagacctact tctctgaaga ggatgtctgt ggctgcctgg aggctggcat caggacggag   1380

gaggagtttc agctgctgca catcttccgt cgggatgccc tgaggttttt cctggcccca   1440

tgtgtggagc cagggcgtgc aggcaccttc gtgttcaccg tgcccgccat gcaggaatac   1500

ctggctgccc tctacattgt gctgggtttg cgcaagacga ccctgcaaaa ggtgggcaag   1560
```

-continued

```
gaagtggctg agctcgtggg ccgtgttggg gaggacgtca gcctggtact gggcatcatg   1620

gccaagctgc tgcctctgcg ggctctgcct ctgctcttca acctgatcaa ggtggttcca   1680

cgagtgtttg ggcgcatggt gggtaaaagc cgggaggcgg tggctcaggc catggtgctg   1740

gagatgtttc gagaggagga ctactacaac gatgatgttc tggaccagat gggcgccagt   1800

atcctgggcg tggagggccc ccggcgccac ccagatgagc cccctgagga tgaagtcttc   1860

gagctcttcc ccatgttcat gggggggctt ctctctgccc acaaccgagc tgtgctagct   1920

cagcttggct gccccatcaa gaacctggat gccctggaga atgcccaggc catcaagaag   1980

aagctgggca agctgggccg gcaggtgctg cccccatcag agctccttga ccacctcttc   2040

ttccactatg agttccagaa ccagcgcttc tccgctgagg tgctcagctc cctgcgtcag   2100

ctcaacctgg caggtgtgcg catgacacca gtcaagtgca cagtggtggc agctgtgctg   2160

ggcagcggaa ggcatgccct ggatgaggtg aacttggcct cctgccagct agatcctgct   2220

gggctgcgca cactcctgcc tgtcttcctg cgtgcccgga agctgggctt gcaactcaac   2280

agcctgggcc ctgaggcctg caaggacctc cgagacctgt tgctgcatga ccagtgccaa   2340

attaccacac tgcggctgtc caacaacccg ctgacggcgg caggtgttgc cgtgctaatg   2400

gaggggctgg caggaaacac ctcagtgacg cacctgtccc tgctgcacac gggccttggg   2460

gacgaaggcc tggagctgct ggctgcccag ctggaccgca accggcagct gcaggagctg   2520

aacgtggcgt acaacggtgc tggtgacaca gcggccctgg ccctggccag agctgcccgg   2580

gagcaccctt ccctggaact gctacacctc tacttcaatg agctgagctc agagggccgc   2640

caggtcttgc gagacttggg ggtgctgct gaaggtggtg cccgggtggt ggtgtcactg   2700

acagagggga cggcggtgtc agaatactgg tcagtgatcc tcagtgaagt ccagcggaac   2760

ctcaatagct gggatcgggc ccgggttcag cgacaccttg agctcctact gcgggatctg   2820

gaagatagcc ggggtgccac ccttaatcct tggcgcaagg cccagctgct gcgagtggag   2880

ggcgaggtca gggccctcct ggagcagctg ggaagctctg gaagctga                2928
```

<210> SEQ ID NO 11
<211> LENGTH: 6763
<212> TYPE: DNA
<213> ORGANISM: Homo sapiens

<400> SEQUENCE: 11

```
ggaggagccg cgagcgctga gggtgagtgc cgggagctct gagggagtct gcactatgga     60

aacaacctgt caatccagct caaggcacac atagcccaga cacccatgag accctctccg    120

tggggaccct agagcaccta tcatgaacga ggagaccaag gctggctcct catggacccc    180

gttggcctcc agctcggcaa caagaacctg tggagctgtc ttgtgaggct gctcaccaaa    240

gacccagaat ggctgaacgc caagatgaag ttcttcctcc ccaacacgga cctggattcc    300

aggaacgaga ccttggaccc tgaacagaga gtcatcctgc aactcaacaa gctgcatgtc    360

cagggttcgg acacctggca gtctttcatt cattgcgtgt gcatgcagct ggaggtgcct    420

ctggacctgg aggtgcttct gctaagtact tttggctatg atgatgggtt caccagccag    480

ctgggagctg aggggaaaag ccaacctgaa tctcagctcc accatggcct gaagcgccca    540

catcagagct gtgggtcctc accccgccgg aagcagtgca agaagcagca gctagagttg    600

gccaagaagt acctgcagct cctgcggacc tctgcccagc agcgctacag gagccaaatc    660

cctgggtcag ggcagcccca cgccttccac caggtctatg tccctccaat cctgcgccgg    720

gccacagcat ccttagacac tccggagggg gccattatgg gggacgtcaa ggtggaagat    780
```

-continued

```
ggtgctgacg tgagcatctc ggacctcttc aacaccaggg ttaacaaggg cccgagggtg    840
accgtgcttt tggggaaggc tggcatgggc aagaccacgc tggcccaccg gctctgccag    900
aagtgggcag agggccatct gaactgtttc caggccctgt tcctttttga attccgccag    960
ctcaacttga tcacgaggtt cctgacaccg tccgagctcc tttttgatct gtacctgagc   1020
cctgaatcgg accacgacac tgtcttccag tacctggaga agaacgctga ccaagtcctg   1080
ctgatctttg atgggctaga tgaggccctc cagcctatgg gtcctgatgg cccaggccca   1140
gtcctcaccc ttttctccca tctctgcaat gggaccctcc tgcctggctg ccgggtgatg   1200
gctacctccc gtccagggaa gctgcctgcc tgcctgcctg cagaggcagc catggtccac   1260
atgttgggct ttgatgggcc acgggtggaa gaatatgtga atcacttctt cagcgcccag   1320
ccatcgcggg agggggccct ggtggagtta cagacaaatg gacgtctccg aagcctgtgt   1380
gcggtgcccg cactgtgcca agtcgcctgt ctctgcctcc accatctgct tcctgaccac   1440
gccccaggcc agtctgtggc cctcctgccc aacatgactc agctctatat gcagatggtg   1500
ctcgccctca gcccccctgg gcacttgccc acctcgtccc tactggacct gggggaggtg   1560
gccctgaggg gcctggagac agggaaggtt atcttctatg caaaagatat tgctccaccc   1620
ttgatagctt ttggggccac tcacagcctg ctgacttcct tctgcgtctg cacaggccct   1680
gggcaccagc agacaggcta tgctttcacc cacctcagcc tgcaggagtt tcttgctgcc   1740
ctgcacctga tggccagccc caaggtgaac aaagacacac ttacccagta tgttaccctc   1800
cattcccgct gggtacagcg gaccaaagct agactgggcc tctcagacca cctccccacc   1860
ttcctggcgg gcctggcatc ctgcacctgc cgccccttcc ttagccacct ggcgcagggc   1920
aatgaggact gtgtgggtgc caagcaggct gctgtagtgc aggtgttgaa gaagttggcc   1980
acccgcaagc tcacagggcc aaaggttgta gagctgtgtc actgtgtgga tgagacacag   2040
gagcctgagc tggccagtct caccgcacaa agcctcccct atcaactgcc cttccacaat   2100
ttcccactga cctgcaccga cctggccacc ctgaccaaca tcctagagca cagggaggcc   2160
cccatccacc tggattttga tggctgtccc ctggagcccc actgccctga ggctctggta   2220
ggctgtgggc agatagagaa tctcagcttt aagagcagga agtgtgggga tgcctttgca   2280
gaagccctct ccaggagctt gccgacaatg gggaggctgc agatgctggg gttagcagga   2340
agtaaaatca ctgcccgagg catcagccac ctggtgaaag ctttgcctct ctgtccacag   2400
ctgaaagaag tcagttttcg ggacaaccag ctcagtgacc aggtggtgct gaacattgtg   2460
gaggttctcc ctcacctacc acggctccgg aagcttgacc tgagcagcaa cagcatctgc   2520
gtgtcaaccc tactctgctt ggcaagggtg gcagtcacgt gtcctaccgt caggatgctt   2580
caggccaggg agcggaccat catcttcctt ctttccccgc ccacagagac aactgcagag   2640
ctacaaagag ctccagacct gcaggaaagt gacggccaga ggaaaggggc tcagagcaga   2700
agcttgacgc tcaggctgca gaagtgtcag ctccaggtcc acgatgcgga ggccctcata   2760
gccctgctcc aggaaggccc tcacctggag gaagtggacc tctcagggaa ccagctggaa   2820
gatgaaggct gtcggctgat ggcagaggct gcatcccagc tgcacatcgc caggaagctg   2880
gacctcagcg acaacgggct ttctgtggcc ggggtgcatt gtgtgctgag ggccgtgagt   2940
gcgtgctgga ccctggcaga gctgcacatc agcctgcagc acaaaaactgt gatcttcatg   3000
tttgcccagg agccagagga gcagaagggg ccccaggaga gggctgcatt tcttgacagc   3060
ctcatgctcc agatgccctc tgagctgcct ctgagctccc gaaggatgag gctgacacat   3120
```

-continued

```
tgtggcctcc aagaaaagca cctagagcag ctctgcaagg ctctgggagg aagctgccac   3180
ctcggtcacc tccacctcga cttctcaggc aatgctctgg gggatgaagg tgcagcccgg   3240
ctggctcagc tgctcccagg gctgggagct ctgcagtcct tgaacctcag tgagaacggt   3300
ttgtccctgg atgccgtgtt gggcttggtt cggtgcttct ccactctgca gtggctcttc   3360
cgcttggaca tcagctttga aagccaacac atcctcctga gaggggacaa gacaagcagg   3420
gatatgtggg ccactggatc tttgccagac ttcccagctg cagccaagtt cttagggttc   3480
cgtcagcgct gcatccccag gagcctctgc ctcagtgagt gtcctctgga gcccccaagc   3540
ctcacccgcc tctgtgccac tctgaaggac tgcccgggac cctggaact gcaattgtcc   3600
tgtgagttcc tgagtgacca gagcctggag actctactgg actgcttacc tcaactccct   3660
cagctgagcc tgctgcagct gagccagacg ggactgtccc cgaaaagccc cttcctgctg   3720
gccaacacct taagcctgtg tccacgggtt aaaaaggtgg atctcaggtc cctgcaccat   3780
gcaactttgc acttcagatc caacgaggag gaggaaggcg tgtgctgtgg caggttcaca   3840
ggctgcagcc tcagccagga gcacgtagag tcactctgct ggttgctgag caagtgtaaa   3900
gacctcagcc aggtggatct ctcagcaaac ctgctgggcg acagcggact cagatgcctt   3960
ctggaatgtc tgccgcaggt gcccatctcc ggtttgcttg atctgagtca caacagcatt   4020
tctcaggaaa gtgccctgta cctgctggag acactgccct cctgcccacg tgtccgggag   4080
gcctcagtga acctgggctc tgagcagagc ttccggattc acttctccag agaggaccag   4140
gctgggaaga cactcaggct aagtgagtgc agcttccggc cagagcacgt gtccaggctg   4200
gccaccggct tgagcaagtc cctgcagctg acggagctca cgctgaccca gtgctgcctg   4260
ggccagaagc agctggccat cctcctgagc ttggtggggc gacccgcagg gctgttcagc   4320
ctcagggtgc aggagccgtg ggcggacaga gccagggttc tctccctgtt agaagtctgc   4380
gcccaggcct caggcagtgt cactgaaatc agcatctccg agacccagca gcagctctgt   4440
gtccagctgg aatttcctcg ccaggaagag aatccagaag ctgtggcact caggttggct   4500
cactgtgacc ttggagccca ccacagcctt cttgtcgggc agctgatgga gacatgtgcc   4560
aggctgcagc agctcagctt gtctcaggtt aacctctgtg aggacgatga tgccagttcc   4620
ctgctgctgc agagcctcct gctgtccctc tctgagctga agacatttcg gctgacctcc   4680
agctgtgtga gcaccgaggg cctcgcccac ctggcatctg gtctgggcca ctgccaccac   4740
ttggaggagc tggacttgtc taacaatcaa tttgatgagg agggcaccaa ggcgctgatg   4800
agggcccttg aggggaaatg gatgctaaag aggctggacc tcagtcacct tctgctgaac   4860
agctccacct tggccttgct tactcacaga ctaagccaga tgacctgcct gcagagcctc   4920
agactgaaca ggaacagtat cggtgatgtc ggttgctgcc acctttctga ggctctcagg   4980
gctgccacca gcctagagga gctggacttg agccacaacc agattggaga cgctggtgtc   5040
cagcacttag ctaccatcct gcctgggctg ccagagctca ggaagataga cctctcaggg   5100
aatagcatca gctcagccgg gggagtgcag ttggcagagt ctctcgttct ttgcaggcgc   5160
ctggaggagt tgatgcttgg ctgcaatgcc ctgggggatc ccacagccct ggggctggct   5220
caggagctgc cccagcacct gagggtccta cacctaccat tcagccatct gggcccaggt   5280
ggggccctga gcctggccca ggccctggat ggatcccccc atttggaaga gatcagcttg   5340
gcggaaaaca acctggctgg aggggtcctg cgtttctgta tggagctccc gctgctcaga   5400
cagatagacc tggtttcctg taagattgac aaccagactg ccaagctcct cacctccagc   5460
ttcacgagct gccctgccct ggaagtaatc ttgctgtcct ggaatctcct cggggatgag   5520
```

-continued

```
gcagctgccg agctggccca ggtgctgccg aagatgggcc ggctgaagag agtggacctg   5580
gagaagaatc agatcacagc tttgggggcc tggctcctgg ctgaaggact ggcccagggg   5640
tctagcatcc aagtcatccg cctctggaat aaccccattc cctgcgacat ggcccagcac   5700
ctgaagagcc aggagcccag gctggacttt gccttctttg acaaccagcc ccaggcccct   5760
tggggtactt gatggccccc tcaagacctt tggaatccag ccaagtgatg cacccaaatg   5820
atccaccttt cgcccactgg gataaatgac tcaggaaaga agagcctcgg cagggcgctc   5880
tgcactccac ccaggaggaa ggatacgtgt gtcctgctgc agtcctcagg gagaactttt   5940
ttgggaacca ggagctgggt ctggacaaag gagtaccctg cattacgtgg gatatgtgtg   6000
atcaattggg gacatgcgac acacaatgag ggtgtcatga caatgcatga cacgtacggt   6060
tatatgtggc agtgtgaccc cttgacatgt ggcgttacat gaaagtcagt gtggcacgtg   6120
ttctgtggca tgggtgctgg catcccaagt ggcaggatac atgattgttg gtctatatat   6180
gacacatgac aaatgtccat gtcacaggac tcatggctgg ccagatgacc tcaggctggc   6240
ccaagatcta atttattaat ttttaaagca aatacatatt tatagattgt gtgtatggag   6300
cagctaagtc aggaaaagtc ttccgcccga gctgggaggg gagagtgtcc atgcactgac   6360
cagtccaggg gctcaagggc cagggctctg gaacaagcca gggactcagc cattaagtcc   6420
cctcctgcct caatcctcag cctacccatc tataaacttg atgactcctc ccttacttac   6480
atactagctt ccaaggacag gtggaggtag ggccagcctg gcgggagtgg agaagcccag   6540
tctgtcctat gtaagggaca aagccaggtc taatggtact gggtaggggg cactgccaag   6600
acaataagct aggctactgg gtccagctac tactttggtg ggattcaggt gagtctccat   6660
gcacttcaca tgttacccag tgttcttgtt acttccaagg agaaccaaga atggctctgt   6720
cacactcgaa gccaggtttg atcaataaac acaatggtat tcc                      6763

<210> SEQ ID NO 12
<211> LENGTH: 1112
<212> TYPE: PRT
<213> ORGANISM: Homo sapiens

<400> SEQUENCE: 12

Met Glu Met Asp Ala Pro Arg Pro Pro Ser Leu Ala Val Pro Gly Ala
1               5                   10                  15

Ala Ser Arg Pro Gly Arg Leu Leu Asp Gly Gly His Gly Arg Gln Gln
            20                  25                  30

Val Gln Ala Leu Ser Ser Gln Leu Leu Glu Val Ile Pro Asp Ser Met
        35                  40                  45

Arg Lys Gln Glu Val Arg Thr Gly Arg Glu Ala Gly Gln Gly His Gly
    50                  55                  60

Thr Gly Ser Pro Ala Glu Gln Val Lys Ala Leu Met Asp Leu Leu Ala
65                  70                  75                  80

Gly Lys Gly Ser Gln Gly Ser His Ala Pro Gln Ala Leu Asp Arg Thr
                85                  90                  95

Pro Asp Ala Pro Leu Gly Pro Cys Ser Asn Asp Ser Arg Ile Gln Arg
            100                 105                 110

His Arg Lys Ala Leu Leu Ser Lys Val Gly Gly Gly Pro Glu Leu Gly
        115                 120                 125

Gly Pro Trp His Arg Leu Ala Ser Leu Leu Leu Val Glu Gly Leu Thr
    130                 135                 140

Asp Leu Gln Leu Arg Glu His Asp Phe Thr Gln Val Glu Ala Thr Arg
```

-continued

```
145                 150                 155                 160

Gly Gly Gly His Pro Ala Arg Thr Val Ala Leu Asp Arg Leu Phe Leu
                165                 170                 175

Pro Leu Ser Arg Val Ser Val Pro Pro Arg Val Ser Ile Thr Ile Gly
            180                 185                 190

Val Ala Gly Met Gly Lys Thr Thr Leu Val Arg His Phe Val Arg Leu
        195                 200                 205

Trp Ala His Gly Gln Val Gly Lys Asp Phe Ser Leu Val Leu Pro Leu
    210                 215                 220

Thr Phe Arg Asp Leu Asn Thr His Glu Lys Leu Cys Ala Asp Arg Leu
225                 230                 235                 240

Ile Cys Ser Val Phe Pro His Val Gly Glu Pro Ser Leu Ala Val Ala
                245                 250                 255

Val Pro Ala Arg Ala Leu Leu Ile Leu Asp Gly Leu Asp Glu Cys Arg
            260                 265                 270

Thr Pro Leu Asp Phe Ser Asn Thr Val Ala Cys Thr Asp Pro Lys Lys
        275                 280                 285

Glu Ile Pro Val Asp His Leu Ile Thr Asn Ile Ile Arg Gly Asn Leu
    290                 295                 300

Phe Pro Glu Val Ser Ile Trp Ile Thr Ser Arg Pro Ser Ala Ser Gly
305                 310                 315                 320

Gln Ile Pro Gly Gly Leu Val Asp Arg Met Thr Glu Ile Arg Gly Phe
                325                 330                 335

Asn Glu Glu Glu Ile Lys Val Cys Leu Glu Gln Met Phe Pro Glu Asp
            340                 345                 350

Gln Ala Leu Leu Gly Trp Met Leu Ser Gln Val Gln Ala Asp Arg Ala
        355                 360                 365

Leu Tyr Leu Met Cys Thr Val Pro Ala Phe Cys Arg Leu Thr Gly Met
    370                 375                 380

Ala Leu Gly His Leu Trp Arg Ser Arg Thr Gly Pro Gln Asp Ala Glu
385                 390                 395                 400

Leu Trp Pro Pro Arg Thr Leu Cys Glu Leu Tyr Ser Trp Tyr Phe Arg
                405                 410                 415

Met Ala Leu Ser Gly Glu Gly Gln Glu Lys Gly Lys Ala Ser Pro Arg
            420                 425                 430

Ile Glu Gln Val Ala His Gly Gly Arg Lys Met Val Gly Thr Leu Gly
        435                 440                 445

Arg Leu Ala Phe His Gly Leu Leu Lys Lys Lys Tyr Val Phe Tyr Glu
    450                 455                 460

Gln Asp Met Lys Ala Phe Gly Val Asp Leu Ala Leu Leu Gln Gly Ala
465                 470                 475                 480

Pro Cys Ser Cys Phe Leu Gln Arg Glu Glu Thr Leu Ala Ser Ser Val
                485                 490                 495

Ala Tyr Cys Phe Thr His Leu Ser Leu Gln Glu Phe Val Ala Ala Ala
            500                 505                 510

Tyr Tyr Tyr Gly Ala Ser Arg Arg Ala Ile Phe Asp Leu Phe Thr Glu
        515                 520                 525

Ser Gly Val Ser Trp Pro Arg Leu Gly Phe Leu Thr His Phe Arg Ser
    530                 535                 540

Ala Ala Gln Arg Ala Met Gln Ala Glu Asp Gly Arg Leu Asp Val Phe
545                 550                 555                 560

Leu Arg Phe Leu Ser Gly Leu Leu Ser Pro Arg Val Asn Ala Leu Leu
                565                 570                 575
```

-continued

```
Ala Gly Ser Leu Leu Ala Gln Gly Glu His Gln Ala Tyr Arg Thr Gln
            580                 585                 590

Val Ala Glu Leu Leu Gln Gly Cys Leu Arg Pro Asp Ala Ala Val Cys
        595                 600                 605

Ala Arg Ala Ile Asn Val Leu His Cys Leu His Glu Leu Gln His Thr
    610                 615                 620

Glu Leu Ala Arg Ser Val Glu Glu Ala Met Glu Ser Gly Ala Leu Ala
625                 630                 635                 640

Arg Leu Thr Gly Pro Ala His Arg Ala Ala Leu Ala Tyr Leu Leu Gln
                645                 650                 655

Val Ser Asp Ala Cys Ala Gln Glu Ala Asn Leu Ser Leu Ser Leu Ser
            660                 665                 670

Gln Gly Val Leu Gln Ser Leu Leu Pro Gln Leu Leu Tyr Cys Arg Lys
        675                 680                 685

Leu Arg Leu Asp Thr Asn Gln Phe Gln Asp Pro Val Met Glu Leu Leu
    690                 695                 700

Gly Ser Val Leu Ser Gly Lys Asp Cys Arg Ile Gln Lys Ile Ser Leu
705                 710                 715                 720

Ala Glu Asn Gln Ile Ser Asn Lys Gly Ala Lys Ala Leu Ala Arg Ser
                725                 730                 735

Leu Leu Val Asn Arg Ser Leu Thr Ser Leu Asp Leu Arg Gly Asn Ser
            740                 745                 750

Ile Gly Pro Gln Gly Ala Lys Ala Leu Ala Asp Ala Leu Lys Ile Asn
        755                 760                 765

Arg Thr Leu Thr Ser Leu Ser Leu Gln Gly Asn Thr Val Arg Asp Asp
    770                 775                 780

Gly Ala Arg Ser Met Ala Glu Ala Leu Ala Ser Asn Arg Thr Leu Ser
785                 790                 795                 800

Met Leu His Leu Gln Lys Asn Ser Ile Gly Pro Met Gly Ala Gln Arg
                805                 810                 815

Met Ala Asp Ala Leu Lys Gln Asn Arg Ser Leu Lys Glu Leu Met Phe
            820                 825                 830

Ser Ser Asn Ser Ile Gly Asp Gly Gly Ala Lys Ala Leu Ala Glu Ala
        835                 840                 845

Leu Lys Val Asn Gln Gly Leu Glu Ser Leu Asp Leu Gln Ser Asn Ser
    850                 855                 860

Ile Ser Asp Ala Gly Val Ala Ala Leu Met Gly Ala Leu Cys Thr Asn
865                 870                 875                 880

Gln Thr Leu Leu Ser Leu Ser Leu Arg Glu Asn Ser Ile Ser Pro Glu
                885                 890                 895

Gly Ala Gln Ala Ile Ala His Ala Leu Cys Ala Asn Ser Thr Leu Lys
            900                 905                 910

Asn Leu Asp Leu Thr Ala Asn Leu Leu His Asp Gln Gly Ala Arg Ala
        915                 920                 925

Ile Ala Val Ala Val Arg Glu Asn Arg Thr Leu Thr Ser Leu His Leu
    930                 935                 940

Gln Trp Asn Phe Ile Gln Ala Gly Ala Ala Gln Ala Leu Gly Gln Ala
945                 950                 955                 960

Leu Gln Leu Asn Arg Ser Leu Thr Ser Leu Asp Leu Gln Glu Asn Ala
                965                 970                 975

Ile Gly Asp Asp Gly Ala Cys Ala Val Ala Arg Ala Leu Lys Val Asn
            980                 985                 990
```

-continued

```
Thr Ala Leu Thr Ala Leu Tyr Leu  Gln Val Ala Ser Ile  Gly Ala Ser
        995                 1000                 1005

Gly Ala  Gln Val Leu Gly Glu  Ala Leu Ala Val Asn  Arg Thr Leu
    1010                 1015                 1020

Glu Ile  Leu Asp Leu Arg Gly  Asn Ala Ile Gly Val  Ala Gly Ala
    1025                 1030                 1035

Lys Ala  Leu Ala Asn Ala Leu  Lys Val Asn Ser Ser  Leu Arg Arg
    1040                 1045                 1050

Leu Asn  Leu Gln Glu Asn Ser  Leu Gly Met Asp Gly  Ala Ile Cys
    1055                 1060                 1065

Ile Ala  Thr Ala Leu Ser Gly  Asn His Arg Leu Gln  His Ile Asn
    1070                 1075                 1080

Leu Gln  Gly Asn His Ile Gly  Asp Ser Gly Ala Arg  Met Ile Ser
    1085                 1090                 1095

Glu Ala  Ile Lys Thr Asn Ala  Pro Thr Cys Thr Val  Glu Met
    1100                 1105                 1110


<210> SEQ ID NO 13
<211> LENGTH: 1093
<212> TYPE: PRT
<213> ORGANISM: Homo sapiens

<400> SEQUENCE: 13

Met Ala Asp Ser Ser Ser Ser Ser Phe Phe Pro Asp Phe Gly Leu Leu
1               5                   10                  15

Leu Tyr Leu Glu Glu Leu Asn Lys Glu Glu Leu Asn Thr Phe Lys Leu
            20                  25                  30

Phe Leu Lys Glu Thr Met Glu Pro Glu His Gly Leu Thr Pro Trp Asn
        35                  40                  45

Glu Val Lys Lys Ala Arg Arg Glu Asp Leu Ala Asn Leu Met Lys Lys
    50                  55                  60

Tyr Tyr Pro Gly Glu Lys Ala Trp Ser Val Ser Leu Lys Ile Phe Gly
65                  70                  75                  80

Lys Met Asn Leu Lys Asp Leu Cys Glu Arg Ala Lys Glu Glu Ile Asn
                85                  90                  95

Trp Ser Ala Gln Thr Ile Gly Pro Asp Asp Ala Lys Ala Gly Glu Thr
            100                 105                 110

Gln Glu Asp Gln Glu Ala Val Leu Gly Asp Gly Thr Glu Tyr Arg Asn
        115                 120                 125

Arg Ile Lys Glu Lys Phe Cys Ile Thr Trp Asp Lys Lys Ser Leu Ala
    130                 135                 140

Gly Lys Pro Glu Asp Phe His His Gly Ile Ala Glu Lys Asp Arg Lys
145                 150                 155                 160

Leu Leu Glu His Leu Phe Asp Val Asp Val Lys Thr Gly Ala Gln Pro
                165                 170                 175

Gln Ile Val Val Leu Gln Gly Ala Ala Gly Val Gly Lys Thr Thr Leu
            180                 185                 190

Val Arg Lys Ala Met Leu Asp Trp Ala Glu Gly Ser Leu Tyr Gln Gln
        195                 200                 205

Arg Phe Lys Tyr Val Phe Tyr Leu Asn Gly Arg Glu Ile Asn Gln Leu
    210                 215                 220

Lys Glu Arg Ser Phe Ala Gln Leu Ile Ser Lys Asp Trp Pro Ser Thr
225                 230                 235                 240

Glu Gly Pro Ile Glu Glu Ile Met Tyr Gln Pro Ser Ser Leu Leu Phe
                245                 250                 255
```

-continued

```
Ile Ile Asp Ser Phe Asp Glu Leu Asn Phe Ala Phe Glu Glu Pro Glu
            260                 265                 270

Phe Ala Leu Cys Glu Asp Trp Thr Gln Glu His Pro Val Ser Phe Leu
        275                 280                 285

Met Ser Ser Leu Leu Arg Lys Val Met Leu Pro Glu Ala Ser Leu Leu
    290                 295                 300

Val Thr Thr Arg Leu Thr Thr Ser Lys Arg Leu Lys Gln Leu Leu Lys
305                 310                 315                 320

Asn His His Tyr Val Glu Leu Leu Gly Met Ser Glu Asp Ala Arg Glu
                325                 330                 335

Glu Tyr Ile Tyr Gln Phe Phe Glu Asp Lys Arg Trp Ala Met Lys Val
            340                 345                 350

Phe Ser Ser Leu Lys Ser Asn Glu Met Leu Phe Ser Met Cys Gln Val
        355                 360                 365

Pro Leu Val Cys Trp Ala Ala Cys Thr Cys Leu Lys Gln Gln Met Glu
    370                 375                 380

Lys Gly Gly Asp Val Thr Leu Thr Cys Gln Thr Thr Thr Ala Leu Phe
385                 390                 395                 400

Thr Cys Tyr Ile Ser Ser Leu Phe Thr Pro Val Asp Gly Gly Ser Pro
                405                 410                 415

Ser Leu Pro Asn Gln Ala Gln Leu Arg Arg Leu Cys Gln Val Ala Ala
            420                 425                 430

Lys Gly Ile Trp Thr Met Thr Tyr Val Phe Tyr Arg Glu Asn Leu Arg
        435                 440                 445

Arg Leu Gly Leu Thr Gln Ser Asp Val Ser Ser Phe Met Asp Ser Asn
    450                 455                 460

Ile Ile Gln Lys Asp Ala Glu Tyr Glu Asn Cys Tyr Val Phe Thr His
465                 470                 475                 480

Leu His Val Gln Glu Phe Phe Ala Ala Met Phe Tyr Met Leu Lys Gly
                485                 490                 495

Ser Trp Glu Ala Gly Asn Pro Ser Cys Gln Pro Phe Glu Asp Leu Lys
            500                 505                 510

Ser Leu Leu Gln Ser Thr Ser Tyr Lys Asp Pro His Leu Thr Gln Met
        515                 520                 525

Lys Cys Phe Leu Phe Gly Leu Leu Asn Glu Asp Arg Val Lys Gln Leu
    530                 535                 540

Glu Arg Thr Phe Asn Cys Lys Met Ser Leu Lys Ile Lys Ser Lys Leu
545                 550                 555                 560

Leu Gln Cys Met Glu Val Leu Gly Asn Ser Asp Tyr Ser Pro Ser Gln
                565                 570                 575

Leu Gly Phe Leu Glu Leu Phe His Cys Leu Tyr Glu Thr Gln Asp Lys
            580                 585                 590

Ala Phe Ile Ser Gln Ala Met Arg Cys Phe Pro Lys Val Ala Ile Asn
        595                 600                 605

Ile Cys Glu Lys Ile His Leu Leu Val Ser Ser Phe Cys Leu Lys His
    610                 615                 620

Cys Arg Cys Leu Arg Thr Ile Arg Leu Ser Val Thr Val Val Phe Glu
625                 630                 635                 640

Lys Lys Ile Leu Lys Thr Ser Leu Pro Thr Asn Thr Trp Asp Gly Asp
                645                 650                 655

Arg Ile Thr His Cys Trp Gln Asp Leu Cys Ser Val Leu His Thr Asn
            660                 665                 670
```

-continued

```
Glu His Leu Arg Glu Leu Asp Leu Tyr His Ser Asn Leu Asp Lys Ser
        675                 680                 685

Ala Met Asn Ile Leu His His Glu Leu Arg His Pro Asn Cys Lys Leu
    690                 695                 700

Gln Lys Leu Leu Leu Lys Phe Ile Thr Phe Pro Asp Gly Cys Gln Asp
705                 710                 715                 720

Ile Ser Thr Ser Leu Ile His Asn Lys Asn Leu Met His Leu Asp Leu
                725                 730                 735

Lys Gly Ser Asp Ile Gly Asp Asn Gly Val Lys Ser Leu Cys Glu Ala
            740                 745                 750

Leu Lys His Pro Glu Cys Lys Leu Gln Thr Leu Arg Leu Glu Ser Cys
        755                 760                 765

Asn Leu Thr Val Phe Cys Cys Leu Asn Ile Ser Asn Ala Leu Ile Arg
    770                 775                 780

Ser Gln Ser Leu Ile Phe Leu Asn Leu Ser Thr Asn Asn Leu Leu Asp
785                 790                 795                 800

Asp Gly Val Gln Leu Leu Cys Glu Ala Leu Arg His Pro Lys Cys Tyr
                805                 810                 815

Leu Glu Arg Leu Ser Leu Glu Ser Cys Gly Leu Thr Glu Ala Gly Cys
            820                 825                 830

Glu Tyr Leu Ser Leu Ala Leu Ile Ser Asn Lys Arg Leu Thr His Leu
        835                 840                 845

Cys Leu Ala Asp Asn Val Leu Gly Asp Gly Gly Val Lys Leu Met Ser
    850                 855                 860

Asp Ala Leu Gln His Ala Gln Cys Thr Leu Lys Ser Leu Val Leu Arg
865                 870                 875                 880

Arg Cys His Phe Thr Ser Leu Ser Ser Glu Tyr Leu Ser Thr Ser Leu
                885                 890                 895

Leu His Asn Lys Ser Leu Thr His Leu Asp Leu Gly Ser Asn Trp Leu
            900                 905                 910

Gln Asp Asn Gly Val Lys Leu Leu Cys Asp Val Phe Arg His Pro Ser
        915                 920                 925

Cys Asn Leu Gln Asp Leu Glu Leu Met Gly Cys Val Leu Thr Asn Ala
    930                 935                 940

Cys Cys Leu Asp Leu Ala Ser Val Ile Leu Asn Asn Pro Asn Leu Arg
945                 950                 955                 960

Ser Leu Asp Leu Gly Asn Asn Asp Leu Gln Asp Asp Gly Val Lys Ile
                965                 970                 975

Leu Cys Asp Ala Leu Arg Tyr Pro Asn Cys Asn Ile Gln Arg Leu Gly
            980                 985                 990

Leu Glu Tyr Cys Gly Leu Thr Ser  Leu Cys Cys Gln Asp  Leu Ser Ser
        995                 1000                1005

Ala Leu  Ile Cys Asn Lys Arg  Leu Ile Lys Met Asn  Leu Thr Gln
    1010                1015                1020

Asn Thr  Leu Gly Tyr Glu Gly  Ile Val Lys Leu Tyr  Lys Val Leu
    1025                1030                1035

Lys Ser  Pro Lys Cys Lys Leu  Gln Val Leu Gly Leu  Cys Lys Glu
    1040                1045                1050

Ala Phe  Asp Glu Glu Ala Gln  Lys Leu Leu Glu Ala  Val Gly Val
    1055                1060                1065

Ser Asn  Pro His Leu Ile Ile  Lys Pro Asp Cys Asn  Tyr His Asn
    1070                1075                1080

Glu Glu  Asp Val Ser Trp Trp  Trp Cys Phe
```

-continued 1085 1090

<210> SEQ ID NO 14
<211> LENGTH: 991
<212> TYPE: PRT
<213> ORGANISM: Homo sapiens

<400> SEQUENCE: 14

```
Met Ala Glu Ser Phe Phe Ser Asp Phe Gly Leu Leu Trp Tyr Leu Lys
1               5                   10                  15

Glu Leu Arg Lys Glu Glu Phe Trp Lys Phe Lys Glu Leu Leu Lys Gln
            20                  25                  30

Pro Leu Glu Lys Phe Glu Leu Lys Pro Ile Pro Trp Ala Glu Leu Lys
        35                  40                  45

Lys Ala Ser Lys Glu Asp Val Ala Lys Leu Leu Asp Lys His Tyr Pro
    50                  55                  60

Gly Lys Gln Ala Trp Glu Val Thr Leu Asn Leu Phe Leu Gln Ile Asn
65                  70                  75                  80

Arg Lys Asp Leu Trp Thr Lys Ala Gln Glu Glu Met Arg Asn Lys Leu
                85                  90                  95

Asn Pro Tyr Arg Lys His Met Lys Glu Thr Phe Gln Leu Ile Trp Glu
            100                 105                 110

Lys Glu Thr Cys Leu His Val Pro Glu His Phe Tyr Lys Glu Thr Met
        115                 120                 125

Lys Asn Glu Tyr Lys Glu Leu Asn Asp Ala Tyr Thr Ala Ala Ala Arg
    130                 135                 140

Arg His Thr Val Val Leu Glu Gly Pro Asp Gly Ile Gly Lys Thr Thr
145                 150                 155                 160

Leu Leu Arg Lys Val Met Leu Asp Trp Ala Glu Gly Asn Leu Trp Lys
                165                 170                 175

Asp Arg Phe Thr Phe Val Phe Phe Leu Asn Val Cys Glu Met Asn Gly
            180                 185                 190

Ile Ala Glu Thr Ser Leu Leu Glu Leu Leu Ser Arg Asp Trp Pro Glu
        195                 200                 205

Ser Ser Glu Lys Ile Glu Asp Ile Phe Ser Gln Pro Glu Arg Ile Leu
    210                 215                 220

Phe Ile Met Asp Gly Phe Glu Gln Leu Lys Phe Asn Leu Gln Leu Lys
225                 230                 235                 240

Ala Asp Leu Ser Asp Asp Trp Arg Gln Arg Gln Pro Met Pro Ile Ile
                245                 250                 255

Leu Ser Ser Leu Leu Gln Lys Lys Met Leu Pro Glu Ser Ser Leu Leu
            260                 265                 270

Ile Ala Leu Gly Lys Leu Ala Met Gln Lys His Tyr Phe Met Leu Arg
        275                 280                 285

His Pro Lys Leu Ile Lys Leu Leu Gly Phe Ser Glu Ser Glu Lys Lys
    290                 295                 300

Ser Tyr Phe Ser Tyr Phe Phe Gly Glu Lys Ser Lys Ala Leu Lys Val
305                 310                 315                 320

Phe Asn Phe Val Arg Asp Asn Gly Pro Leu Phe Ile Leu Cys His Asn
                325                 330                 335

Pro Phe Thr Cys Trp Leu Val Cys Thr Cys Val Lys Gln Arg Leu Glu
            340                 345                 350

Arg Gly Glu Asp Leu Glu Ile Asn Ser Gln Asn Thr Thr Tyr Leu Tyr
        355                 360                 365
```

-continued

```
Ala Ser Phe Leu Thr Thr Val Phe Lys Ala Gly Ser Gln Ser Phe Pro
    370                 375                 380

Pro Lys Val Asn Arg Ala Arg Leu Lys Ser Leu Cys Ala Leu Ala Ala
385                 390                 395                 400

Glu Gly Ile Trp Thr Tyr Thr Phe Val Phe Ser His Gly Asp Leu Arg
                405                 410                 415

Arg Asn Gly Leu Ser Glu Ser Glu Gly Val Met Trp Val Gly Met Arg
            420                 425                 430

Leu Leu Gln Arg Arg Gly Asp Cys Phe Ala Phe Met His Leu Cys Ile
        435                 440                 445

Gln Glu Phe Cys Ala Ala Met Phe Tyr Leu Leu Lys Arg Pro Lys Asp
    450                 455                 460

Asp Pro Asn Pro Ala Ile Gly Ser Ile Thr Gln Leu Val Arg Ala Ser
465                 470                 475                 480

Val Val Gln Pro Gln Thr Leu Leu Thr Gln Val Gly Ile Phe Met Phe
                485                 490                 495

Gly Ile Ser Thr Glu Glu Ile Val Ser Met Leu Glu Thr Ser Phe Gly
            500                 505                 510

Phe Pro Leu Ser Lys Asp Leu Lys Gln Glu Ile Thr Gln Cys Leu Glu
        515                 520                 525

Ser Leu Ser Gln Cys Glu Ala Asp Arg Glu Ala Ile Ala Phe Gln Glu
    530                 535                 540

Leu Phe Ile Gly Leu Phe Glu Thr Gln Glu Lys Glu Phe Val Thr Lys
545                 550                 555                 560

Val Met Asn Phe Phe Glu Glu Val Phe Ile Tyr Ile Gly Asn Ile Glu
                565                 570                 575

His Leu Val Ile Ala Ser Phe Cys Leu Lys His Cys Gln His Leu Thr
            580                 585                 590

Thr Leu Arg Met Cys Val Glu Asn Ile Phe Pro Asp Asp Ser Gly Cys
        595                 600                 605

Ile Ser Asp Tyr Asn Glu Lys Leu Val Tyr Trp Arg Glu Leu Cys Ser
    610                 615                 620

Met Phe Ile Thr Asn Lys Asn Phe Gln Ile Leu Asp Met Glu Asn Thr
625                 630                 635                 640

Ser Leu Asp Asp Pro Ser Leu Ala Ile Leu Cys Lys Ala Leu Ala Gln
                645                 650                 655

Pro Val Cys Lys Leu Arg Lys Leu Ile Phe Thr Ser Val Tyr Phe Gly
            660                 665                 670

His Asp Ser Glu Leu Phe Lys Ala Val Leu His Asn Pro His Leu Lys
        675                 680                 685

Leu Leu Ser Leu Tyr Gly Thr Ser Leu Ser Gln Ser Asp Ile Arg His
    690                 695                 700

Leu Cys Glu Thr Leu Lys His Pro Met Cys Lys Ile Glu Glu Leu Ile
705                 710                 715                 720

Leu Gly Lys Cys Asp Ile Ser Ser Glu Val Cys Glu Asp Ile Ala Ser
                725                 730                 735

Val Leu Ala Cys Asn Ser Lys Leu Lys His Leu Ser Leu Val Glu Asn
            740                 745                 750

Pro Leu Arg Asp Glu Gly Met Thr Leu Leu Cys Glu Ala Leu Lys His
        755                 760                 765

Ser His Cys Ala Leu Glu Arg Leu Met Leu Met Tyr Cys Cys Leu Thr
    770                 775                 780

Ser Val Ser Cys Asp Ser Ile Ser Glu Val Leu Leu Cys Ser Lys Ser
```

-continued

```
785                 790                 795                 800

Leu Ser Leu Leu Asp Leu Gly Ser Asn Ala Leu Glu Asp Asn Gly Val
                805                 810                 815

Ala Ser Leu Cys Ala Ala Leu Lys His Pro Gly Cys Ser Ile Arg Glu
            820                 825                 830

Leu Trp Leu Met Gly Cys Phe Leu Thr Ser Asp Ser Cys Lys Asp Ile
        835                 840                 845

Ala Ala Val Leu Ile Cys Asn Gly Lys Leu Lys Thr Leu Lys Leu Gly
    850                 855                 860

His Asn Glu Ile Gly Asp Thr Gly Val Arg Gln Leu Cys Ala Ala Leu
865                 870                 875                 880

Gln His Pro His Cys Lys Leu Glu Cys Leu Gly Leu Gln Thr Cys Pro
                885                 890                 895

Ile Thr Arg Ala Cys Cys Asp Asp Ile Ala Ala Ala Leu Ile Ala Cys
            900                 905                 910

Lys Thr Leu Arg Ser Leu Asn Leu Asp Trp Ile Ala Leu Asp Ala Asp
        915                 920                 925

Ala Val Val Val Leu Cys Glu Ala Leu Ser His Pro Asp Cys Ala Leu
    930                 935                 940

Gln Met Leu Gly Leu His Lys Ser Gly Phe Asp Glu Glu Thr Gln Lys
945                 950                 955                 960

Ile Leu Met Ser Val Glu Glu Lys Ile Pro His Leu Thr Ile Ser His
                965                 970                 975

Gly Pro Trp Ile Asp Glu Glu Tyr Lys Ile Arg Gly Val Leu Leu
            980                 985                 990


<210> SEQ ID NO 15
<211> LENGTH: 655
<212> TYPE: PRT
<213> ORGANISM: Homo sapiens

<400> SEQUENCE: 15

Met Ala Met Ala Lys Ala Arg Lys Pro Arg Glu Ala Leu Leu Trp Ala
1               5                   10                  15

Leu Ser Asp Leu Glu Glu Asn Asp Phe Lys Lys Leu Lys Phe Tyr Leu
            20                  25                  30

Arg Asp Met Thr Leu Ser Glu Gly Gln Pro Pro Leu Ala Arg Gly Glu
        35                  40                  45

Leu Glu Gly Leu Ile Pro Val Asp Leu Ala Glu Leu Leu Ile Ser Lys
    50                  55                  60

Tyr Gly Glu Lys Glu Ala Val Lys Val Val Leu Lys Gly Leu Lys Val
65                  70                  75                  80

Met Asn Leu Leu Glu Leu Val Asp Gln Leu Ser His Ile Cys Leu His
                85                  90                  95

Asp Tyr Arg Glu Val Tyr Arg Glu His Val Arg Cys Leu Glu Glu Trp
            100                 105                 110

Gln Glu Ala Gly Val Asn Gly Arg Tyr Asn Gln Val Leu Leu Val Ala
        115                 120                 125

Lys Pro Ser Ser Glu Ser Pro Glu Ser Leu Ala Cys Pro Phe Pro Glu
    130                 135                 140

Gln Glu Leu Glu Ser Val Thr Val Glu Ala Leu Phe Asp Ser Gly Glu
145                 150                 155                 160

Lys Pro Ser Leu Ala Pro Ser Leu Val Val Leu Gln Gly Ser Ala Gly
                165                 170                 175
```

-continued

```
Thr Gly Lys Thr Thr Leu Ala Arg Lys Met Val Leu Asp Trp Ala Thr
            180                 185                 190

Gly Thr Leu Tyr Pro Gly Arg Phe Asp Tyr Val Phe Tyr Val Ser Cys
        195                 200                 205

Lys Glu Val Val Leu Leu Leu Glu Ser Lys Leu Glu Gln Leu Leu Phe
    210                 215                 220

Trp Cys Cys Gly Asp Asn Gln Ala Pro Val Thr Glu Ile Leu Arg Gln
225                 230                 235                 240

Pro Glu Arg Leu Leu Phe Ile Leu Asp Gly Phe Asp Glu Leu Gln Arg
                245                 250                 255

Pro Phe Glu Glu Lys Leu Lys Lys Arg Gly Leu Ser Pro Lys Glu Ser
            260                 265                 270

Leu Leu His Leu Leu Ile Arg Arg His Thr Leu Pro Thr Cys Ser Leu
        275                 280                 285

Leu Ile Thr Thr Arg Pro Leu Ala Leu Arg Asn Leu Glu Pro Leu Leu
    290                 295                 300

Lys Gln Ala Arg His Val His Ile Leu Gly Phe Ser Glu Glu Glu Arg
305                 310                 315                 320

Ala Arg Tyr Phe Ser Ser Tyr Phe Thr Asp Glu Lys Gln Ala Asp Arg
                325                 330                 335

Ala Phe Asp Ile Val Gln Lys Asn Asp Ile Leu Tyr Lys Ala Cys Gln
            340                 345                 350

Val Pro Gly Ile Cys Trp Val Val Cys Ser Trp Leu Gln Gly Gln Met
        355                 360                 365

Glu Arg Gly Lys Val Val Leu Glu Thr Pro Arg Asn Ser Thr Asp Ile
    370                 375                 380

Phe Met Ala Tyr Val Ser Thr Phe Leu Pro Pro Asp Asp Asp Gly Gly
385                 390                 395                 400

Cys Ser Glu Leu Ser Arg His Arg Val Leu Arg Ser Leu Cys Ser Leu
                405                 410                 415

Ala Ala Glu Gly Ile Gln His Gln Arg Phe Leu Phe Glu Glu Ala Glu
            420                 425                 430

Leu Arg Lys His Asn Leu Asp Gly Pro Arg Leu Ala Ala Phe Leu Ser
        435                 440                 445

Ser Asn Asp Tyr Gln Leu Gly Leu Ala Ile Lys Lys Phe Tyr Ser Phe
    450                 455                 460

Arg His Ile Ser Phe Gln Asp Phe Phe His Ala Met Ser Tyr Leu Val
465                 470                 475                 480

Lys Glu Asp Gln Ser Arg Leu Gly Lys Glu Ser Arg Arg Glu Val Gln
                485                 490                 495

Arg Leu Leu Glu Val Lys Glu Gln Glu Gly Asn Asp Glu Met Thr Leu
            500                 505                 510

Thr Met Gln Phe Leu Leu Asp Ile Ser Lys Lys Asp Ser Phe Ser Asn
        515                 520                 525

Leu Glu Leu Lys Phe Cys Phe Arg Ile Ser Pro Cys Leu Ala Gln Asp
    530                 535                 540

Leu Lys His Phe Lys Glu Gln Met Glu Ser Met Lys His Asn Arg Thr
545                 550                 555                 560

Trp Asp Leu Glu Phe Ser Leu Tyr Glu Ala Lys Ile Lys Asn Leu Val
                565                 570                 575

Lys Gly Ile Gln Met Asn Asn Val Ser Phe Lys Ile Lys His Ser Asn
            580                 585                 590

Glu Lys Lys Ser Gln Ser Gln Asn Leu Phe Ser Val Lys Ser Ser Leu
```

-continued

```
        595                 600                 605

Ser His Gly Pro Lys Glu Glu Gln Lys Cys Pro Ser Val His Gly Gln
    610                 615                 620

Lys Glu Gly Lys Asp Asn Ile Ala Gly Thr Gln Lys Glu Ala Ser Thr
625                 630                 635                 640

Gly Lys Gly Arg Gly Thr Glu Glu Thr Pro Lys Asn Thr Tyr Ile
                645                 650                 655


<210> SEQ ID NO 16
<211> LENGTH: 975
<212> TYPE: PRT
<213> ORGANISM: Homo sapiens

<400> SEQUENCE: 16

Met Arg Trp Gly His His Leu Pro Arg Ala Ser Trp Gly Ser Gly Phe
1               5                   10                  15

Arg Arg Ala Leu Gln Arg Pro Asp Asp Arg Ile Pro Phe Leu Ile His
            20                  25                  30

Trp Ser Trp Pro Leu Gln Gly Glu Arg Pro Phe Gly Pro Pro Arg Ala
        35                  40                  45

Phe Ile Arg His His Gly Ser Ser Val Asp Ser Ala Pro Pro Ser Gly
    50                  55                  60

Arg His Gly Arg Leu Phe Pro Ser Ala Ser Ala Thr Glu Ala Ile Gln
65                  70                  75                  80

Arg His Arg Arg Asn Leu Ala Glu Trp Phe Ser Arg Leu Pro Arg Glu
                85                  90                  95

Glu Arg Gln Phe Gly Pro Thr Phe Ala Leu Asp Thr Val His Val Asp
            100                 105                 110

Pro Val Ile Arg Glu Ser Thr Pro Asp Glu Leu Leu Arg Pro Pro Ala
        115                 120                 125

Glu Leu Ala Leu Glu His Gln Pro Pro Gln Ala Gly Leu Pro Pro Leu
    130                 135                 140

Ala Leu Ser Gln Leu Phe Asn Pro Asp Ala Cys Gly Arg Arg Val Gln
145                 150                 155                 160

Thr Val Val Leu Tyr Gly Thr Val Gly Thr Gly Lys Ser Thr Leu Val
                165                 170                 175

Arg Lys Met Val Leu Asp Trp Cys Tyr Gly Arg Leu Pro Ala Phe Glu
            180                 185                 190

Leu Leu Ile Pro Phe Ser Cys Glu Asp Leu Ser Ser Leu Gly Pro Ala
        195                 200                 205

Pro Ala Ser Leu Cys Gln Leu Val Ala Gln Arg Tyr Thr Pro Leu Lys
    210                 215                 220

Glu Val Leu Pro Leu Met Ala Ala Ala Gly Ser His Leu Leu Phe Val
225                 230                 235                 240

Leu His Gly Leu Glu His Leu Asn Leu Asp Phe Arg Leu Ala Gly Thr
                245                 250                 255

Gly Leu Cys Ser Asp Pro Glu Glu Pro Gln Glu Pro Ala Ala Ile Ile
            260                 265                 270

Val Asn Leu Leu Arg Lys Tyr Met Leu Pro Gln Ala Ser Ile Leu Val
        275                 280                 285

Thr Thr Arg Pro Ser Ala Ile Gly Arg Ile Pro Ser Lys Tyr Val Gly
    290                 295                 300

Arg Tyr Gly Glu Ile Cys Gly Phe Ser Asp Thr Asn Leu Gln Lys Leu
305                 310                 315                 320
```

-continued

```
Tyr Phe Gln Leu Arg Leu Asn Gln Pro Tyr Cys Gly Tyr Ala Val Gly
                325                 330                 335

Gly Ser Gly Val Ser Ala Thr Pro Ala Gln Arg Asp His Leu Val Gln
            340                 345                 350

Met Leu Ser Arg Asn Leu Glu Gly His His Gln Ile Ala Ala Ala Cys
        355                 360                 365

Phe Leu Pro Ser Tyr Cys Trp Leu Val Cys Ala Thr Leu His Phe Leu
    370                 375                 380

His Ala Pro Thr Pro Ala Gly Gln Thr Leu Thr Ser Ile Tyr Thr Ser
385                 390                 395                 400

Phe Leu Arg Leu Asn Phe Ser Gly Glu Thr Leu Asp Ser Thr Asp Pro
                405                 410                 415

Ser Asn Leu Ser Leu Met Ala Tyr Ala Ala Arg Thr Met Gly Lys Leu
            420                 425                 430

Ala Tyr Glu Gly Val Ser Ser Arg Lys Thr Tyr Phe Ser Glu Glu Asp
        435                 440                 445

Val Cys Gly Cys Leu Glu Ala Gly Ile Arg Thr Glu Glu Glu Phe Gln
    450                 455                 460

Leu Leu His Ile Phe Arg Arg Asp Ala Leu Arg Phe Phe Leu Ala Pro
465                 470                 475                 480

Cys Val Glu Pro Gly Arg Ala Gly Thr Phe Val Phe Thr Val Pro Ala
                485                 490                 495

Met Gln Glu Tyr Leu Ala Ala Leu Tyr Ile Val Leu Gly Leu Arg Lys
            500                 505                 510

Thr Thr Leu Gln Lys Val Gly Lys Glu Val Ala Glu Leu Val Gly Arg
        515                 520                 525

Val Gly Glu Asp Val Ser Leu Val Leu Gly Ile Met Ala Lys Leu Leu
    530                 535                 540

Pro Leu Arg Ala Leu Pro Leu Leu Phe Asn Leu Ile Lys Val Val Pro
545                 550                 555                 560

Arg Val Phe Gly Arg Met Val Gly Lys Ser Arg Glu Ala Val Ala Gln
                565                 570                 575

Ala Met Val Leu Glu Met Phe Arg Glu Glu Asp Tyr Tyr Asn Asp Asp
            580                 585                 590

Val Leu Asp Gln Met Gly Ala Ser Ile Leu Gly Val Glu Gly Pro Arg
        595                 600                 605

Arg His Pro Asp Glu Pro Pro Glu Asp Glu Val Phe Glu Leu Phe Pro
    610                 615                 620

Met Phe Met Gly Gly Leu Leu Ser Ala His Asn Arg Ala Val Leu Ala
625                 630                 635                 640

Gln Leu Gly Cys Pro Ile Lys Asn Leu Asp Ala Leu Glu Asn Ala Gln
                645                 650                 655

Ala Ile Lys Lys Lys Leu Gly Lys Leu Gly Arg Gln Val Leu Pro Pro
            660                 665                 670

Ser Glu Leu Leu Asp His Leu Phe Phe His Tyr Glu Phe Gln Asn Gln
        675                 680                 685

Arg Phe Ser Ala Glu Val Leu Ser Ser Leu Arg Gln Leu Asn Leu Ala
    690                 695                 700

Gly Val Arg Met Thr Pro Val Lys Cys Thr Val Val Ala Ala Val Leu
705                 710                 715                 720

Gly Ser Gly Arg His Ala Leu Asp Glu Val Asn Leu Ala Ser Cys Gln
                725                 730                 735

Leu Asp Pro Ala Gly Leu Arg Thr Leu Leu Pro Val Phe Leu Arg Ala
```

-continued

```
            740                 745                 750

Arg Lys Leu Gly Leu Gln Leu Asn Ser Leu Gly Pro Glu Ala Cys Lys
        755                 760                 765

Asp Leu Arg Asp Leu Leu Leu His Asp Gln Cys Gln Ile Thr Thr Leu
    770                 775                 780

Arg Leu Ser Asn Asn Pro Leu Thr Glu Ala Gly Val Ala Val Leu Met
785                 790                 795                 800

Glu Gly Leu Ala Gly Asn Thr Ser Val Thr His Leu Ser Leu Leu His
                805                 810                 815

Thr Gly Leu Gly Asp Glu Gly Leu Glu Leu Leu Ala Ala Gln Leu Asp
            820                 825                 830

Arg Asn Arg Gln Leu Gln Glu Leu Asn Val Ala Tyr Asn Gly Ala Gly
        835                 840                 845

Asp Thr Ala Ala Leu Ala Leu Ala Arg Ala Ala Arg Glu His Pro Ser
    850                 855                 860

Leu Glu Leu Leu His Leu Tyr Phe Asn Glu Leu Ser Ser Glu Gly Arg
865                 870                 875                 880

Gln Val Leu Arg Asp Leu Gly Gly Ala Ala Glu Gly Gly Ala Arg Val
                885                 890                 895

Val Val Ser Leu Thr Glu Gly Thr Ala Val Ser Glu Tyr Trp Ser Val
            900                 905                 910

Ile Leu Ser Glu Val Gln Arg Asn Leu Asn Ser Trp Asp Arg Ala Arg
        915                 920                 925

Val Gln Arg His Leu Glu Leu Leu Leu Arg Asp Leu Glu Asp Ser Arg
    930                 935                 940

Gly Ala Thr Leu Asn Pro Trp Arg Lys Ala Gln Leu Leu Arg Val Glu
945                 950                 955                 960

Gly Glu Val Arg Ala Leu Leu Glu Gln Leu Gly Ser Ser Gly Ser
                965                 970                 975


<210> SEQ ID NO 17
<211> LENGTH: 1009
<212> TYPE: PRT
<213> ORGANISM: Homo sapiens

<400> SEQUENCE: 17

Met Thr Ser Pro Gln Leu Glu Trp Thr Leu Gln Thr Leu Leu Glu Gln
1               5                   10                  15

Leu Asn Glu Asp Glu Leu Lys Ser Phe Lys Ser Leu Leu Trp Ala Phe
            20                  25                  30

Pro Leu Glu Asp Val Leu Gln Lys Thr Pro Trp Ser Glu Val Glu Glu
        35                  40                  45

Ala Asp Gly Glu Lys Leu Ala Glu Ile Leu Val Asn Thr Ser Ser Glu
    50                  55                  60

Asn Trp Ile Arg Asn Ala Thr Val Asn Ile Leu Glu Glu Met Asn Leu
65                  70                  75                  80

Thr Glu Leu Cys Lys Met Ala Lys Ala Glu Met Met Glu Asp Gly Gln
                85                  90                  95

Val Gln Glu Ile Asp Asn Pro Glu Leu Gly Asp Ala Glu Glu Asp Ser
            100                 105                 110

Glu Leu Ala Lys Pro Gly Glu Lys Glu Gly Trp Arg Asn Ser Met Glu
        115                 120                 125

Lys Gln Ser Leu Val Trp Lys Asn Thr Phe Trp Gln Gly Asp Ile Asp
    130                 135                 140
```

-continued

```
Asn Phe His Asp Asp Val Thr Leu Arg Asn Gln Arg Phe Ile Pro Phe
145                 150                 155                 160

Leu Asn Pro Arg Thr Pro Arg Lys Leu Thr Pro Tyr Thr Val Val Leu
                165                 170                 175

His Gly Pro Ala Gly Val Gly Lys Thr Thr Leu Ala Lys Lys Cys Met
            180                 185                 190

Leu Asp Trp Thr Asp Cys Asn Leu Ser Pro Thr Leu Arg Tyr Ala Phe
        195                 200                 205

Tyr Leu Ser Cys Lys Glu Leu Ser Arg Met Gly Pro Cys Ser Phe Ala
    210                 215                 220

Glu Leu Ile Ser Lys Asp Trp Pro Glu Leu Gln Asp Asp Ile Pro Ser
225                 230                 235                 240

Ile Leu Ala Gln Ala Gln Arg Ile Leu Phe Val Val Asp Gly Leu Asp
                245                 250                 255

Glu Leu Lys Val Pro Pro Gly Ala Leu Ile Gln Asp Ile Cys Gly Asp
            260                 265                 270

Trp Glu Lys Lys Lys Pro Val Pro Val Leu Leu Gly Ser Leu Leu Lys
        275                 280                 285

Arg Lys Met Leu Pro Arg Ala Ala Leu Leu Val Thr Thr Arg Pro Arg
    290                 295                 300

Ala Leu Arg Asp Leu Gln Leu Leu Ala Gln Gln Pro Ile Tyr Val Arg
305                 310                 315                 320

Val Glu Gly Phe Leu Glu Glu Asp Arg Arg Ala Tyr Phe Leu Arg His
                325                 330                 335

Phe Gly Asp Glu Asp Gln Ala Met Arg Ala Phe Glu Leu Met Arg Ser
            340                 345                 350

Asn Ala Ala Leu Phe Gln Leu Gly Ser Ala Pro Ala Val Cys Trp Ile
        355                 360                 365

Val Cys Thr Thr Leu Lys Leu Gln Met Glu Lys Gly Glu Asp Pro Val
    370                 375                 380

Pro Thr Cys Leu Thr Arg Thr Gly Leu Phe Leu Arg Phe Leu Cys Ser
385                 390                 395                 400

Arg Phe Pro Gln Gly Ala Gln Leu Arg Gly Ala Leu Arg Thr Leu Ser
                405                 410                 415

Leu Leu Ala Ala Gln Gly Leu Trp Ala Gln Met Ser Val Phe His Arg
            420                 425                 430

Glu Asp Leu Glu Arg Leu Gly Val Gln Glu Ser Asp Leu Arg Leu Phe
        435                 440                 445

Leu Asp Gly Asp Ile Leu Arg Gln Asp Arg Val Ser Lys Gly Cys Tyr
    450                 455                 460

Ser Phe Ile His Leu Ser Phe Gln Gln Phe Leu Thr Ala Leu Phe Tyr
465                 470                 475                 480

Ala Leu Glu Lys Glu Glu Gly Glu Asp Arg Asp Gly His Ala Trp Asp
                485                 490                 495

Ile Gly Asp Val Gln Lys Leu Leu Ser Gly Glu Glu Arg Leu Lys Asn
            500                 505                 510

Pro Asp Leu Ile Gln Val Gly His Phe Leu Phe Gly Leu Ala Asn Glu
        515                 520                 525

Lys Arg Ala Lys Glu Leu Glu Ala Thr Phe Gly Cys Arg Met Ser Pro
    530                 535                 540

Asp Ile Lys Gln Glu Leu Leu Gln Cys Lys Ala His Leu His Ala Asn
545                 550                 555                 560

Lys Pro Leu Ser Val Thr Asp Leu Lys Glu Val Leu Gly Cys Leu Tyr
```

-continued

```
            565                 570                 575

Glu Ser Gln Glu Glu Glu Leu Ala Lys Val Val Val Ala Pro Phe Lys
        580                 585                 590

Glu Ile Ser Ile His Leu Thr Asn Thr Ser Glu Val Met His Cys Ser
    595                 600                 605

Phe Ser Leu Lys His Cys Gln Asp Leu Gln Lys Leu Ser Leu Gln Val
    610                 615                 620

Ala Lys Gly Val Phe Leu Glu Asn Tyr Met Asp Phe Glu Leu Asp Ile
625                 630                 635                 640

Glu Phe Glu Ser Ser Asn Ser Asn Leu Lys Phe Leu Glu Val Lys Gln
                645                 650                 655

Ser Phe Leu Ser Asp Ser Ser Val Arg Ile Leu Cys Asp His Val Thr
            660                 665                 670

Arg Ser Thr Cys His Leu Gln Lys Val Glu Ile Lys Asn Val Thr Pro
        675                 680                 685

Asp Thr Ala Tyr Arg Asp Phe Cys Leu Ala Phe Ile Gly Lys Lys Thr
    690                 695                 700

Leu Thr His Leu Thr Leu Ala Gly His Ile Glu Trp Glu Arg Thr Met
705                 710                 715                 720

Met Leu Met Leu Cys Asp Leu Leu Arg Asn His Lys Cys Asn Leu Gln
                725                 730                 735

Tyr Leu Arg Leu Gly Gly His Cys Ala Thr Pro Glu Gln Trp Ala Glu
            740                 745                 750

Phe Phe Tyr Val Leu Lys Ala Asn Gln Ser Leu Lys His Leu Arg Leu
        755                 760                 765

Ser Ala Asn Val Leu Leu Asp Glu Gly Ala Met Leu Leu Tyr Lys Thr
    770                 775                 780

Met Thr Arg Pro Lys His Phe Leu Gln Met Leu Ser Leu Glu Asn Cys
785                 790                 795                 800

Arg Leu Thr Glu Ala Ser Cys Lys Asp Leu Ala Ala Val Leu Val Val
                805                 810                 815

Ser Lys Lys Leu Thr His Leu Cys Leu Ala Lys Asn Pro Ile Gly Asp
            820                 825                 830

Thr Gly Val Lys Phe Leu Cys Glu Gly Leu Ser Tyr Pro Asp Cys Lys
        835                 840                 845

Leu Gln Thr Leu Val Leu Gln Gln Cys Ser Ile Thr Lys Leu Gly Cys
    850                 855                 860

Arg Tyr Leu Ser Glu Ala Leu Gln Glu Ala Cys Ser Leu Thr Asn Leu
865                 870                 875                 880

Asp Leu Ser Ile Asn Gln Ile Ala Arg Gly Leu Trp Ile Leu Cys Gln
                885                 890                 895

Ala Leu Glu Asn Pro Asn Cys Asn Leu Lys His Leu Arg Leu Trp Ser
            900                 905                 910

Cys Ser Leu Met Pro Phe Tyr Cys Gln His Leu Gly Ser Ala Leu Leu
        915                 920                 925

Ser Asn Gln Lys Leu Glu Thr Leu Asp Leu Gly Gln Asn His Leu Trp
    930                 935                 940

Lys Ser Gly Ile Ile Lys Leu Phe Gly Val Leu Arg Gln Arg Thr Gly
945                 950                 955                 960

Ser Leu Lys Ile Leu Arg Leu Lys Thr Tyr Glu Thr Asn Leu Glu Ile
                965                 970                 975

Lys Lys Leu Leu Glu Glu Val Lys Glu Lys Asn Pro Lys Leu Thr Ile
            980                 985                 990
```

```
Asp Cys Asn Ala Ser Gly Ala Thr  Ala Pro Pro Cys Cys  Asp Phe Phe
        995                 1000                 1005

Cys


<210> SEQ ID NO 18
<211> LENGTH: 1036
<212> TYPE: PRT
<213> ORGANISM: Homo sapiens

<400> SEQUENCE: 18

Met Asn Phe Ser Val Ile Thr Cys Pro Asn Gly Gly Thr Asn Gln Gly
1               5                   10                  15

Leu Leu Pro Tyr Leu Met Ala Leu Asp Gln Tyr Gln Leu Glu Glu Phe
            20                  25                  30

Lys Leu Cys Leu Glu Pro Gln Gln Leu Met Asp Phe Trp Ser Ala Pro
        35                  40                  45

Gln Gly His Phe Pro Arg Ile Pro Trp Ala Asn Leu Arg Ala Ala Asp
    50                  55                  60

Pro Leu Asn Leu Ser Phe Leu Leu Asp Glu His Phe Pro Lys Gly Gln
65                  70                  75                  80

Ala Trp Lys Val Val Leu Gly Ile Phe Gln Thr Met Asn Leu Thr Ser
                85                  90                  95

Leu Cys Glu Lys Val Arg Ala Glu Met Lys Glu Asn Val Gln Thr Gln
            100                 105                 110

Glu Leu Gln Asp Pro Thr Gln Glu Asp Leu Glu Met Leu Glu Ala Ala
        115                 120                 125

Ala Gly Asn Met Gln Thr Gln Gly Cys Gln Asp Pro Asn Gln Glu Glu
    130                 135                 140

Leu Asp Glu Leu Glu Glu Glu Thr Gly Asn Val Gln Ala Gln Gly Cys
145                 150                 155                 160

Gln Asp Pro Asn Gln Glu Glu Pro Glu Met Leu Glu Glu Ala Asp His
                165                 170                 175

Arg Arg Lys Tyr Arg Glu Asn Met Lys Ala Glu Leu Leu Glu Thr Trp
            180                 185                 190

Asp Asn Ile Ser Trp Pro Lys Asp His Val Tyr Ile Arg Asn Thr Ser
        195                 200                 205

Lys Asp Glu His Glu Glu Leu Gln Arg Leu Leu Asp Pro Asn Arg Thr
    210                 215                 220

Arg Ala Gln Ala Gln Thr Ile Val Leu Val Gly Arg Ala Gly Val Gly
225                 230                 235                 240

Lys Thr Thr Leu Ala Met Gln Ala Met Leu His Trp Ala Asn Gly Val
                245                 250                 255

Leu Phe Gln Gln Arg Phe Ser Tyr Val Phe Tyr Leu Ser Cys His Lys
            260                 265                 270

Ile Arg Tyr Met Lys Glu Thr Thr Phe Ala Glu Leu Ile Ser Leu Asp
        275                 280                 285

Trp Pro Asp Phe Asp Ala Pro Ile Glu Glu Phe Met Ser Gln Pro Glu
    290                 295                 300

Lys Leu Leu Phe Ile Ile Asp Gly Phe Glu Glu Ile Ile Ile Ser Glu
305                 310                 315                 320

Ser Arg Ser Glu Ser Leu Asp Asp Gly Ser Pro Cys Thr Asp Trp Tyr
                325                 330                 335

Gln Glu Leu Pro Val Thr Lys Ile Leu His Ser Leu Leu Lys Lys Glu
            340                 345                 350
```

-continued

```
Leu Val Pro Leu Ala Thr Leu Leu Ile Thr Ile Lys Thr Trp Phe Val
        355                 360                 365

Arg Asp Leu Lys Ala Ser Leu Val Asn Pro Cys Phe Val Gln Ile Thr
    370                 375                 380

Gly Phe Thr Gly Asp Asp Leu Arg Val Tyr Phe Met Arg His Phe Asp
385                 390                 395                 400

Asp Ser Ser Glu Val Glu Lys Ile Leu Gln Gln Leu Arg Lys Asn Glu
                405                 410                 415

Thr Leu Phe His Ser Cys Ser Ala Pro Met Val Cys Trp Thr Val Cys
            420                 425                 430

Ser Cys Leu Lys Gln Pro Lys Val Arg Tyr Tyr Asp Leu Gln Ser Ile
        435                 440                 445

Thr Gln Thr Thr Thr Ser Leu Tyr Ala Tyr Phe Phe Ser Asn Leu Phe
    450                 455                 460

Ser Thr Ala Glu Val Asp Leu Ala Asp Asp Ser Trp Pro Gly Gln Trp
465                 470                 475                 480

Arg Ala Leu Cys Ser Leu Ala Ile Glu Gly Leu Trp Ser Met Asn Phe
                485                 490                 495

Thr Phe Asn Lys Glu Asp Thr Glu Ile Glu Gly Leu Glu Val Pro Phe
            500                 505                 510

Ile Asp Ser Leu Tyr Glu Phe Asn Ile Leu Gln Lys Ile Asn Asp Cys
        515                 520                 525

Gly Gly Cys Thr Thr Phe Thr His Leu Ser Phe Gln Glu Phe Phe Ala
    530                 535                 540

Ala Met Ser Phe Val Leu Glu Glu Pro Arg Glu Phe Pro Pro His Ser
545                 550                 555                 560

Thr Lys Pro Gln Glu Met Lys Met Leu Leu Gln His Val Leu Leu Asp
                565                 570                 575

Lys Glu Ala Tyr Trp Thr Pro Val Val Leu Phe Phe Phe Gly Leu Leu
            580                 585                 590

Asn Lys Asn Ile Ala Arg Glu Leu Glu Asp Thr Leu His Cys Lys Ile
        595                 600                 605

Ser Pro Arg Val Met Glu Glu Leu Leu Lys Trp Gly Glu Glu Leu Gly
    610                 615                 620

Lys Ala Glu Ser Ala Ser Leu Gln Phe His Ile Leu Arg Leu Phe His
625                 630                 635                 640

Cys Leu His Glu Ser Gln Glu Glu Asp Phe Thr Lys Lys Met Leu Gly
                645                 650                 655

Arg Ile Phe Glu Val Asp Leu Asn Ile Leu Glu Asp Glu Glu Leu Gln
            660                 665                 670

Ala Ser Ser Phe Cys Leu Lys His Cys Lys Arg Leu Asn Lys Leu Arg
        675                 680                 685

Leu Ser Val Ser Ser His Ile Leu Glu Arg Asp Leu Glu Ile Leu Glu
    690                 695                 700

Thr Ser Lys Phe Asp Ser Arg Met His Ala Trp Asn Ser Ile Cys Ser
705                 710                 715                 720

Thr Leu Val Thr Asn Glu Asn Leu His Glu Leu Asp Leu Ser Asn Ser
                725                 730                 735

Lys Leu His Ala Ser Ser Val Lys Gly Leu Cys Leu Ala Leu Lys Asn
            740                 745                 750

Pro Arg Cys Lys Val Gln Lys Leu Thr Cys Lys Ser Val Thr Pro Glu
        755                 760                 765
```

-continued

```
Trp Val Leu Gln Asp Leu Ile Ile Ala Leu Gln Gly Asn Ser Lys Leu
    770                 775                 780

Thr His Leu Asn Phe Ser Ser Asn Lys Leu Gly Met Thr Val Pro Leu
785                 790                 795                 800

Ile Leu Lys Ala Leu Arg His Ser Ala Cys Asn Leu Lys Tyr Leu Cys
                805                 810                 815

Leu Glu Lys Cys Asn Leu Ser Ala Ala Ser Cys Gln Asp Leu Ala Leu
            820                 825                 830

Phe Leu Thr Ser Ile Gln His Val Thr Arg Leu Cys Leu Gly Phe Asn
        835                 840                 845

Arg Leu Gln Asp Asp Gly Ile Lys Leu Leu Cys Ala Ala Leu Thr His
    850                 855                 860

Pro Lys Cys Ala Leu Glu Arg Leu Glu Leu Trp Phe Cys Gln Leu Ala
865                 870                 875                 880

Ala Pro Ala Cys Lys His Leu Ser Asp Ala Leu Leu Gln Asn Arg Ser
                885                 890                 895

Leu Thr His Leu Asn Leu Ser Lys Asn Ser Leu Arg Asp Glu Gly Val
            900                 905                 910

Lys Phe Leu Cys Glu Ala Leu Gly Arg Pro Asp Gly Asn Leu Gln Ser
        915                 920                 925

Leu Asn Leu Ser Gly Cys Ser Phe Thr Arg Glu Gly Cys Gly Glu Leu
    930                 935                 940

Ala Asn Ala Leu Ser His Asn His Asn Val Lys Ile Leu Asp Leu Gly
945                 950                 955                 960

Glu Asn Asp Leu Gln Asp Asp Gly Val Lys Leu Leu Cys Glu Ala Leu
                965                 970                 975

Lys Pro His Arg Ala Leu His Thr Leu Gly Leu Ala Lys Cys Asn Leu
            980                 985                 990

Thr Thr Ala Cys Cys Gln His Leu  Phe Ser Val Leu Ser  Ser Ser Lys
        995                 1000                1005

Ser Leu  Val Asn Leu Asn Leu  Leu Gly Asn Glu Leu  Asp Thr Asp
    1010                1015                1020

Gly Val  Lys Met Leu Cys Phe  Lys Lys Thr Cys Thr  Met
    1025                1030                1035


<210> SEQ ID NO 19
<211> LENGTH: 1048
<212> TYPE: PRT
<213> ORGANISM: Homo sapiens

<400> SEQUENCE: 19

Met Ser Asp Val Asn Pro Pro Ser Asp Thr Pro Ile Pro Phe Ser Ser
1               5                   10                  15

Ser Ser Thr His Ser Ser His Ile Pro Pro Trp Thr Phe Ser Cys Tyr
            20                  25                  30

Pro Gly Ser Pro Cys Glu Asn Gly Val Met Leu Tyr Met Arg Asn Val
        35                  40                  45

Ser His Glu Glu Leu Gln Arg Phe Lys Gln Leu Leu Leu Thr Glu Leu
    50                  55                  60

Ser Thr Gly Thr Met Pro Ile Thr Trp Asp Gln Val Glu Thr Ala Ser
65                  70                  75                  80

Trp Ala Glu Val Val His Leu Leu Ile Glu Arg Phe Pro Gly Arg Arg
                85                  90                  95

Ala Trp Asp Val Thr Ser Asn Ile Phe Ala Ile Met Asn Cys Asp Lys
            100                 105                 110
```

-continued

```
Met Cys Val Val Val Arg Arg Glu Ile Asn Ala Ile Leu Pro Thr Leu
        115                 120                 125

Glu Pro Glu Asp Leu Asn Val Gly Glu Thr Gln Val Asn Leu Glu Glu
    130                 135                 140

Gly Glu Ser Gly Lys Ile Arg Arg Tyr Lys Ser Asn Val Met Glu Lys
145                 150                 155                 160

Phe Phe Pro Ile Trp Asp Ile Thr Thr Trp Pro Gly Asn Gln Arg Asp
                165                 170                 175

Phe Phe Tyr Gln Gly Val His Arg His Glu Glu Tyr Leu Pro Cys Leu
            180                 185                 190

Leu Leu Pro Lys Arg Pro Gln Gly Arg Gln Pro Lys Thr Val Ala Ile
        195                 200                 205

Gln Gly Ala Pro Gly Ile Gly Lys Thr Ile Leu Ala Lys Lys Val Met
    210                 215                 220

Phe Glu Trp Ala Arg Asn Lys Phe Tyr Ala His Lys Arg Trp Cys Ala
225                 230                 235                 240

Phe Tyr Phe His Cys Gln Glu Val Asn Gln Thr Thr Asp Gln Ser Phe
                245                 250                 255

Ser Glu Leu Ile Glu Gln Lys Trp Pro Gly Ser Gln Asp Leu Val Ser
            260                 265                 270

Lys Ile Met Ser Lys Pro Asp Gln Leu Leu Leu Leu Leu Asp Gly Phe
        275                 280                 285

Glu Glu Leu Thr Ser Thr Leu Ile Asp Arg Leu Glu Asp Leu Ser Glu
    290                 295                 300

Asp Trp Arg Gln Lys Leu Pro Gly Ser Val Leu Leu Ser Ser Leu Leu
305                 310                 315                 320

Ser Lys Thr Met Leu Pro Glu Ala Thr Leu Leu Ile Met Ile Arg Phe
                325                 330                 335

Thr Ser Trp Gln Thr Cys Lys Pro Leu Leu Lys Cys Pro Ser Leu Val
            340                 345                 350

Thr Leu Pro Gly Phe Asn Thr Met Glu Lys Ile Lys Tyr Phe Gln Met
        355                 360                 365

Tyr Phe Gly His Thr Glu Glu Gly Asp Gln Val Leu Ser Phe Ala Met
    370                 375                 380

Glu Asn Thr Ile Leu Phe Ser Met Cys Arg Val Pro Val Val Cys Trp
385                 390                 395                 400

Met Val Cys Ser Gly Leu Lys Gln Gln Met Glu Arg Gly Asn Asn Leu
                405                 410                 415

Thr Gln Ser Cys Pro Asn Ala Thr Ser Val Phe Val Arg Tyr Ile Ser
            420                 425                 430

Ser Leu Phe Pro Thr Arg Ala Glu Asn Phe Ser Arg Lys Ile His Gln
        435                 440                 445

Ala Gln Leu Glu Gly Leu Cys His Leu Ala Ala Asp Ser Met Trp His
    450                 455                 460

Arg Lys Trp Val Leu Gly Lys Glu Asp Leu Glu Glu Ala Lys Leu Asp
465                 470                 475                 480

Gln Thr Gly Val Thr Ala Phe Leu Gly Met Ser Ile Leu Arg Arg Ile
                485                 490                 495

Ala Gly Glu Glu Asp His Tyr Val Phe Thr Leu Val Thr Phe Gln Glu
            500                 505                 510

Phe Phe Ala Ala Leu Phe Tyr Val Leu Cys Phe Pro Gln Arg Leu Lys
        515                 520                 525
```

-continued

```
Asn Phe His Val Leu Ser His Val Asn Ile Gln Arg Leu Ile Ala Ser
    530                 535                 540

Pro Arg Gly Ser Lys Ser Tyr Leu Ser His Met Gly Leu Phe Leu Phe
545                 550                 555                 560

Gly Phe Leu Asn Glu Ala Cys Ala Ser Ala Val Glu Gln Ser Phe Gln
                565                 570                 575

Cys Lys Val Ser Phe Gly Asn Lys Arg Lys Leu Leu Lys Val Ile Pro
            580                 585                 590

Leu Leu His Lys Cys Asp Pro Pro Ser Pro Gly Ser Gly Val Pro Gln
        595                 600                 605

Leu Phe Tyr Cys Leu His Glu Ile Arg Glu Glu Ala Phe Val Ser Gln
    610                 615                 620

Ala Leu Asn Asp Tyr His Lys Val Val Leu Arg Ile Gly Asn Asn Lys
625                 630                 635                 640

Glu Val Gln Val Ser Ala Phe Cys Leu Lys Arg Cys Gln Tyr Leu His
                645                 650                 655

Glu Val Glu Leu Thr Val Thr Leu Asn Phe Met Asn Val Trp Lys Leu
            660                 665                 670

Ser Ser Ser Ser His Pro Gly Ser Glu Ala Pro Glu Ser Asn Gly Leu
        675                 680                 685

His Arg Trp Trp Gln Asp Leu Cys Ser Val Phe Ala Thr Asn Asp Lys
    690                 695                 700

Leu Glu Val Leu Thr Met Thr Asn Ser Val Leu Gly Pro Pro Phe Leu
705                 710                 715                 720

Lys Ala Leu Ala Ala Ala Leu Arg His Pro Gln Cys Lys Leu Gln Lys
                725                 730                 735

Leu Leu Leu Arg Arg Val Asn Ser Thr Met Leu Asn Gln Asp Leu Ile
            740                 745                 750

Gly Val Leu Thr Gly Asn Gln His Leu Arg Tyr Leu Glu Ile Gln His
        755                 760                 765

Val Glu Val Glu Ser Lys Ala Val Lys Leu Leu Cys Arg Val Leu Arg
    770                 775                 780

Ser Pro Arg Cys Arg Leu Gln Cys Leu Arg Leu Glu Asp Cys Leu Ala
785                 790                 795                 800

Thr Pro Arg Ile Trp Thr Asp Leu Gly Asn Asn Leu Gln Gly Asn Gly
                805                 810                 815

His Leu Lys Thr Leu Ile Leu Arg Lys Asn Ser Leu Glu Asn Cys Gly
            820                 825                 830

Ala Tyr Tyr Leu Ser Val Ala Gln Leu Glu Arg Leu Ser Ile Glu Asn
        835                 840                 845

Cys Asn Leu Thr Gln Leu Thr Cys Glu Ser Leu Ala Ser Cys Leu Arg
    850                 855                 860

Gln Ser Lys Met Leu Thr His Leu Ser Leu Ala Glu Asn Ala Leu Lys
865                 870                 875                 880

Asp Glu Gly Ala Lys His Ile Trp Asn Ala Leu Pro His Leu Arg Cys
                885                 890                 895

Pro Leu Gln Arg Leu Val Leu Arg Lys Cys Asp Leu Thr Phe Asn Cys
            900                 905                 910

Cys Gln Asp Met Ile Ser Ala Leu Cys Lys Asn Lys Thr Leu Lys Ser
        915                 920                 925

Leu Asp Leu Ser Phe Asn Ser Leu Lys Asp Asp Gly Val Ile Leu Leu
    930                 935                 940

Cys Glu Ala Leu Lys Asn Pro Asp Cys Thr Leu Gln Ile Leu Glu Leu
```

-continued

```
945                 950                 955                 960

Glu Asn Cys Leu Phe Thr Ser Ile Cys Cys Gln Ala Met Ala Ser Met
                965                 970                 975

Leu Arg Lys Asn Gln His Leu Arg His Leu Asp Leu Ser Lys Asn Ala
            980                 985                 990

Ile Gly Val Tyr Gly Ile Leu Thr  Leu Cys Glu Ala Phe  Ser Ser Gln
        995                 1000                1005

Lys Lys  Arg Glu Glu Val Ile  Phe Cys Ile Pro Ala  Trp Thr Arg
    1010                1015                1020

Ile Thr  Ser Phe Ser Pro Thr  Pro His Pro Pro Asp  Phe Thr Gly
    1025                1030                1035

Lys Ser  Asp Cys Leu Ser Gln  Ile Asn Pro
    1040                1045


<210> SEQ ID NO 20
<211> LENGTH: 1033
<212> TYPE: PRT
<213> ORGANISM: Homo sapiens

<400> SEQUENCE: 20

Met Ala Glu Ser Asp Ser Thr Asp Phe Asp Leu Leu Trp Tyr Leu Glu
1               5                   10                  15

Asn Leu Ser Asp Lys Glu Phe Gln Ser Phe Lys Lys Tyr Leu Ala Arg
            20                  25                  30

Lys Ile Leu Asp Phe Lys Leu Pro Gln Phe Pro Leu Ile Gln Met Thr
        35                  40                  45

Lys Glu Glu Leu Ala Asn Val Leu Pro Ile Ser Tyr Glu Gly Gln Tyr
    50                  55                  60

Ile Trp Asn Met Leu Phe Ser Ile Phe Ser Met Met Arg Lys Glu Asp
65                  70                  75                  80

Leu Cys Arg Lys Ile Ile Gly Arg Arg Asn Arg Asn Gln Glu Ala Cys
                85                  90                  95

Lys Ala Val Met Arg Arg Lys Phe Met Leu Gln Trp Glu Ser His Thr
            100                 105                 110

Phe Gly Lys Phe His Tyr Lys Phe Phe Arg Asp Val Ser Ser Asp Val
        115                 120                 125

Phe Tyr Ile Leu Gln Leu Ala Tyr Asp Ser Thr Ser Tyr Tyr Ser Ala
    130                 135                 140

Asn Asn Leu Asn Val Phe Leu Met Gly Glu Arg Ala Ser Gly Lys Thr
145                 150                 155                 160

Ile Val Ile Asn Leu Ala Val Leu Arg Trp Ile Lys Gly Glu Met Trp
                165                 170                 175

Gln Asn Met Ile Ser Tyr Val Val His Leu Thr Ser His Glu Ile Asn
            180                 185                 190

Gln Met Thr Asn Ser Ser Leu Ala Glu Leu Ile Ala Lys Asp Trp Pro
        195                 200                 205

Asp Gly Gln Ala Pro Ile Ala Asp Ile Leu Ser Asp Pro Lys Lys Leu
    210                 215                 220

Leu Phe Ile Leu Glu Asp Leu Asp Asn Ile Arg Phe Glu Leu Asn Val
225                 230                 235                 240

Asn Glu Ser Ala Leu Cys Ser Asn Ser Thr Gln Lys Val Pro Ile Pro
                245                 250                 255

Val Leu Leu Val Ser Leu Leu Lys Arg Lys Met Ala Pro Gly Cys Trp
            260                 265                 270
```

-continued

```
Phe Leu Ile Ser Ser Arg Pro Thr Arg Gly Asn Asn Val Lys Thr Phe
        275                 280                 285

Leu Lys Glu Val Asp Cys Cys Thr Thr Leu Gln Leu Ser Asn Gly Lys
    290                 295                 300

Arg Glu Ile Tyr Phe Asn Ser Phe Phe Lys Asp Arg Gln Arg Ala Ser
305                 310                 315                 320

Ala Ala Leu Gln Leu Val His Glu Asp Glu Ile Leu Val Gly Leu Cys
                325                 330                 335

Arg Val Ala Ile Leu Cys Trp Ile Thr Cys Thr Val Leu Lys Arg Gln
            340                 345                 350

Met Asp Lys Gly Arg Asp Phe Gln Leu Cys Cys Gln Thr Pro Thr Asp
        355                 360                 365

Leu His Ala His Phe Leu Ala Asp Ala Leu Thr Ser Glu Ala Gly Leu
    370                 375                 380

Thr Ala Asn Gln Tyr His Leu Gly Leu Leu Lys Arg Leu Cys Leu Leu
385                 390                 395                 400

Ala Ala Gly Gly Leu Phe Leu Ser Thr Leu Asn Phe Ser Gly Glu Asp
                405                 410                 415

Leu Arg Cys Val Gly Phe Thr Glu Ala Asp Val Ser Val Leu Gln Ala
            420                 425                 430

Ala Asn Ile Leu Leu Pro Ser Asn Thr His Lys Asp Arg Tyr Lys Phe
        435                 440                 445

Ile His Leu Asn Val Gln Glu Phe Cys Thr Ala Ile Ala Phe Leu Met
    450                 455                 460

Ala Val Pro Asn Tyr Leu Ile Pro Ser Gly Ser Arg Glu Tyr Lys Glu
465                 470                 475                 480

Lys Arg Glu Gln Tyr Ser Asp Phe Asn Gln Val Phe Thr Phe Ile Phe
                485                 490                 495

Gly Leu Leu Asn Ala Asn Arg Arg Lys Ile Leu Glu Thr Ser Phe Gly
            500                 505                 510

Tyr Gln Leu Pro Met Val Asp Ser Phe Lys Trp Tyr Ser Val Gly Tyr
        515                 520                 525

Met Lys His Leu Asp Arg Asp Pro Glu Lys Leu Thr His His Met Pro
    530                 535                 540

Leu Phe Tyr Cys Leu Tyr Glu Asn Arg Glu Glu Glu Phe Val Lys Thr
545                 550                 555                 560

Ile Val Asp Ala Leu Met Glu Val Thr Val Tyr Leu Gln Ser Asp Lys
                565                 570                 575

Asp Met Met Val Ser Leu Tyr Cys Leu Asp Tyr Cys Cys His Leu Arg
            580                 585                 590

Thr Leu Lys Leu Ser Val Gln Arg Ile Phe Gln Asn Lys Glu Pro Leu
        595                 600                 605

Ile Arg Pro Thr Ala Ser Gln Met Lys Ser Leu Val Tyr Trp Arg Glu
    610                 615                 620

Ile Cys Ser Leu Phe Tyr Thr Met Glu Ser Leu Arg Glu Leu His Ile
625                 630                 635                 640

Phe Asp Asn Asp Leu Asn Gly Ile Ser Glu Arg Ile Leu Ser Lys Ala
                645                 650                 655

Leu Glu His Ser Ser Cys Lys Leu Arg Thr Leu Lys Leu Ser Tyr Val
            660                 665                 670

Ser Thr Ala Ser Gly Phe Glu Asp Leu Leu Lys Ala Leu Ala Arg Asn
        675                 680                 685

Arg Ser Leu Thr Tyr Leu Ser Ile Asn Cys Thr Ser Ile Ser Leu Asn
```

-continued

```
    690                 695                 700

Met Phe Ser Leu Leu His Asp Ile Leu His Glu Pro Thr Cys Gln Ile
705                 710                 715                 720

Ser His Leu Ser Leu Met Lys Cys Asp Leu Arg Ala Ser Glu Cys Glu
                725                 730                 735

Glu Ile Ala Ser Leu Leu Ile Ser Gly Gly Ser Leu Arg Lys Leu Thr
            740                 745                 750

Leu Ser Ser Asn Pro Leu Arg Ser Asp Gly Met Asn Ile Leu Cys Asp
        755                 760                 765

Ala Leu Leu His Pro Asn Cys Thr Leu Ile Ser Leu Val Leu Val Phe
    770                 775                 780

Cys Cys Leu Thr Glu Asn Cys Cys Ser Ala Leu Gly Arg Val Leu Leu
785                 790                 795                 800

Phe Ser Pro Thr Leu Arg Gln Leu Asp Leu Cys Val Asn Arg Leu Lys
                805                 810                 815

Asn Tyr Gly Val Leu His Val Thr Phe Pro Leu Leu Phe Pro Thr Cys
            820                 825                 830

Gln Leu Glu Glu Leu His Leu Ser Gly Cys Phe Phe Ser Ser Asp Ile
        835                 840                 845

Cys Gln Tyr Ile Ala Ile Val Ile Ala Thr Asn Glu Lys Leu Arg Ser
    850                 855                 860

Leu Glu Ile Gly Ser Asn Lys Ile Glu Asp Ala Gly Met Gln Leu Leu
865                 870                 875                 880

Cys Gly Gly Leu Arg His Pro Asn Cys Met Leu Val Asn Ile Gly Leu
                885                 890                 895

Glu Glu Cys Met Leu Thr Ser Ala Cys Cys Arg Ser Leu Ala Ser Val
            900                 905                 910

Leu Thr Thr Asn Lys Thr Leu Glu Arg Leu Asn Leu Leu Gln Asn His
        915                 920                 925

Leu Gly Asn Asp Gly Val Ala Lys Leu Leu Glu Ser Leu Ile Ser Pro
    930                 935                 940

Asp Cys Val Leu Lys Val Val Gly Leu Pro Leu Thr Gly Leu Asn Thr
945                 950                 955                 960

Gln Thr Gln Gln Leu Leu Met Thr Val Lys Glu Arg Lys Pro Ser Leu
                965                 970                 975

Ile Phe Leu Ser Glu Thr Trp Ser Leu Lys Glu Gly Arg Glu Ile Gly
            980                 985                 990

Val Thr Pro Ala Ser Gln Pro Gly  Ser Ile Ile Pro Asn  Ser Asn Leu
        995                 1000                1005

Asp Tyr  Met Phe Phe Lys Phe  Pro Arg Met Ser Ala  Ala Met Arg
    1010                1015                1020

Thr Ser  Asn Thr Ala Ser Arg  Gln Pro Leu
    1025                1030


<210> SEQ ID NO 21
<211> LENGTH: 975
<212> TYPE: PRT
<213> ORGANISM: Homo sapiens

<400> SEQUENCE: 21

Met Arg Trp Gly His His Leu Pro Arg Ala Ser Trp Gly Ser Gly Phe
1               5                   10                  15

Arg Arg Ala Leu Gln Arg Pro Asp Asp Arg Ile Pro Phe Leu Ile His
            20                  25                  30
```

-continued

```
Trp Ser Trp Pro Leu Gln Gly Glu Arg Pro Phe Gly Pro Pro Arg Ala
        35                  40                  45

Phe Ile Arg His His Gly Ser Ser Val Asp Ser Ala Pro Pro Pro Gly
    50                  55                  60

Arg His Gly Arg Leu Phe Pro Ser Ala Ser Ala Thr Glu Ala Ile Gln
65                  70                  75                  80

Arg His Arg Arg Asn Leu Ala Glu Trp Phe Ser Arg Leu Pro Arg Glu
                85                  90                  95

Glu Arg Gln Phe Gly Pro Thr Phe Ala Leu Asp Thr Val His Val Asp
            100                 105                 110

Pro Val Ile Arg Glu Ser Thr Pro Asp Glu Leu Leu Arg Pro Pro Ala
        115                 120                 125

Glu Leu Ala Leu Glu His Gln Pro Pro Gln Ala Gly Leu Pro Pro Leu
    130                 135                 140

Ala Leu Ser Gln Leu Phe Asn Pro Asp Ala Cys Gly Arg Arg Val Gln
145                 150                 155                 160

Thr Val Val Leu Tyr Gly Thr Val Gly Thr Gly Lys Ser Thr Leu Val
                165                 170                 175

Arg Lys Met Val Leu Asp Trp Cys Tyr Gly Arg Leu Pro Ala Phe Glu
            180                 185                 190

Leu Leu Ile Pro Phe Ser Cys Glu Asp Leu Ser Ser Leu Gly Pro Ala
        195                 200                 205

Pro Ala Ser Leu Cys Gln Leu Val Ala Gln Arg Tyr Thr Pro Leu Lys
    210                 215                 220

Glu Val Leu Pro Leu Met Ala Ala Ala Gly Ser His Leu Leu Phe Val
225                 230                 235                 240

Leu His Gly Leu Glu His Leu Asn Leu Asp Phe Arg Leu Ala Gly Thr
                245                 250                 255

Gly Leu Cys Ser Asp Pro Glu Glu Pro Gln Glu Pro Ala Ala Ile Ile
            260                 265                 270

Val Asn Leu Leu Arg Lys Tyr Met Leu Pro Gln Ala Ser Ile Leu Val
        275                 280                 285

Thr Thr Arg Pro Ser Ala Ile Gly Arg Ile Pro Ser Lys Tyr Val Gly
    290                 295                 300

Arg Tyr Gly Glu Ile Cys Gly Phe Ser Asp Thr Asn Leu Gln Lys Leu
305                 310                 315                 320

Tyr Phe Gln Leu Arg Leu Asn Gln Pro Tyr Cys Gly Tyr Ala Val Gly
                325                 330                 335

Gly Ser Gly Val Ser Ala Thr Pro Ala Gln Arg Asp His Leu Val Gln
            340                 345                 350

Met Leu Ser Arg Asn Leu Glu Gly His His Gln Ile Ala Ala Ala Cys
        355                 360                 365

Phe Leu Pro Ser Tyr Cys Trp Leu Val Cys Ala Thr Leu His Phe Leu
    370                 375                 380

His Ala Pro Thr Pro Ala Gly Gln Thr Leu Thr Ser Ile Tyr Thr Ser
385                 390                 395                 400

Phe Leu Arg Leu Asn Phe Ser Gly Glu Thr Leu Asp Ser Thr Asp Pro
                405                 410                 415

Ser Asn Leu Ser Leu Met Ala Tyr Ala Ala Arg Thr Met Gly Lys Leu
            420                 425                 430

Ala Tyr Glu Gly Val Ser Ser Arg Lys Thr Tyr Phe Ser Glu Glu Asp
        435                 440                 445

Val Cys Gly Cys Leu Glu Ala Gly Ile Arg Thr Glu Glu Glu Phe Gln
```

-continued

```
    450                 455                 460

Leu Leu His Ile Phe Arg Arg Asp Ala Leu Arg Phe Phe Leu Ala Pro
465                 470                 475                 480

Cys Val Glu Pro Gly Arg Ala Gly Thr Phe Val Phe Thr Val Pro Ala
                485                 490                 495

Met Gln Glu Tyr Leu Ala Ala Leu Tyr Ile Val Leu Gly Leu Arg Lys
            500                 505                 510

Thr Thr Leu Gln Lys Val Gly Lys Glu Val Ala Glu Leu Val Gly Arg
        515                 520                 525

Val Gly Glu Asp Val Ser Leu Val Leu Gly Ile Met Ala Lys Leu Leu
    530                 535                 540

Pro Leu Arg Ala Leu Pro Leu Leu Phe Asn Leu Ile Lys Val Val Pro
545                 550                 555                 560

Arg Val Phe Gly Arg Met Val Gly Lys Ser Arg Glu Ala Val Ala Gln
                565                 570                 575

Ala Met Val Leu Glu Met Phe Arg Glu Glu Asp Tyr Tyr Asn Asp Asp
            580                 585                 590

Val Leu Asp Gln Met Gly Ala Ser Ile Leu Gly Val Glu Gly Pro Arg
        595                 600                 605

Arg His Pro Asp Glu Pro Pro Glu Asp Glu Val Phe Glu Leu Phe Pro
    610                 615                 620

Met Phe Met Gly Gly Leu Leu Ser Ala His Asn Arg Ala Val Leu Ala
625                 630                 635                 640

Gln Leu Gly Cys Pro Ile Lys Asn Leu Asp Ala Leu Glu Asn Ala Gln
                645                 650                 655

Ala Ile Lys Lys Lys Leu Gly Lys Leu Gly Arg Gln Val Leu Pro Pro
            660                 665                 670

Ser Glu Leu Leu Asp His Leu Phe Phe His Tyr Glu Phe Gln Asn Gln
        675                 680                 685

Arg Phe Ser Ala Glu Val Leu Ser Ser Leu Arg Gln Leu Asn Leu Ala
    690                 695                 700

Gly Val Arg Met Thr Pro Val Lys Cys Thr Val Val Ala Ala Val Leu
705                 710                 715                 720

Gly Ser Gly Arg His Ala Leu Asp Glu Val Asn Leu Ala Ser Cys Gln
                725                 730                 735

Leu Asp Pro Ala Gly Leu Arg Thr Leu Leu Pro Val Phe Leu Arg Ala
            740                 745                 750

Arg Lys Leu Gly Leu Gln Leu Asn Ser Leu Gly Pro Glu Ala Cys Lys
        755                 760                 765

Asp Leu Arg Asp Leu Leu Leu His Asp Gln Cys Gln Ile Thr Thr Leu
    770                 775                 780

Arg Leu Ser Asn Asn Pro Leu Thr Ala Ala Gly Val Ala Val Leu Met
785                 790                 795                 800

Glu Gly Leu Ala Gly Asn Thr Ser Val Thr His Leu Ser Leu Leu His
                805                 810                 815

Thr Gly Leu Gly Asp Glu Gly Leu Glu Leu Leu Ala Ala Gln Leu Asp
            820                 825                 830

Arg Asn Arg Gln Leu Gln Glu Leu Asn Val Ala Tyr Asn Gly Ala Gly
        835                 840                 845

Asp Thr Ala Ala Leu Ala Leu Ala Arg Ala Ala Arg Glu His Pro Ser
    850                 855                 860

Leu Glu Leu Leu His Leu Tyr Phe Asn Glu Leu Ser Ser Glu Gly Arg
865                 870                 875                 880
```

-continued

Gln Val Leu Arg Asp Leu Gly Gly Ala Ala Glu Gly Gly Ala Arg Val
885 890 895

Val Val Ser Leu Thr Glu Gly Thr Ala Val Ser Glu Tyr Trp Ser Val
900 905 910

Ile Leu Ser Glu Val Gln Arg Asn Leu Asn Ser Trp Asp Arg Ala Arg
915 920 925

Val Gln Arg His Leu Glu Leu Leu Leu Arg Asp Leu Glu Asp Ser Arg
930 935 940

Gly Ala Thr Leu Asn Pro Trp Arg Lys Ala Gln Leu Leu Arg Val Glu
945 950 955 960

Gly Glu Val Arg Ala Leu Leu Glu Gln Leu Gly Ser Ser Gly Ser
965 970 975

<210> SEQ ID NO 22
<211> LENGTH: 1866
<212> TYPE: PRT
<213> ORGANISM: Homo sapiens

<400> SEQUENCE: 22

Met Asp Pro Val Gly Leu Gln Leu Gly Asn Lys Asn Leu Trp Ser Cys
1 5 10 15

Leu Val Arg Leu Leu Thr Lys Asp Pro Glu Trp Leu Asn Ala Lys Met
20 25 30

Lys Phe Phe Leu Pro Asn Thr Asp Leu Asp Ser Arg Asn Glu Thr Leu
35 40 45

Asp Pro Glu Gln Arg Val Ile Leu Gln Leu Asn Lys Leu His Val Gln
50 55 60

Gly Ser Asp Thr Trp Gln Ser Phe Ile His Cys Val Cys Met Gln Leu
65 70 75 80

Glu Val Pro Leu Asp Leu Glu Val Leu Leu Leu Ser Thr Phe Gly Tyr
85 90 95

Asp Asp Gly Phe Thr Ser Gln Leu Gly Ala Glu Gly Lys Ser Gln Pro
100 105 110

Glu Ser Gln Leu His His Gly Leu Lys Arg Pro His Gln Ser Cys Gly
115 120 125

Ser Ser Pro Arg Arg Lys Gln Cys Lys Lys Gln Gln Leu Glu Leu Ala
130 135 140

Lys Lys Tyr Leu Gln Leu Leu Arg Thr Ser Ala Gln Gln Arg Tyr Arg
145 150 155 160

Ser Gln Ile Pro Gly Ser Gly Gln Pro His Ala Phe His Gln Val Tyr
165 170 175

Val Pro Pro Ile Leu Arg Arg Ala Thr Ala Ser Leu Asp Thr Pro Glu
180 185 190

Gly Ala Ile Met Gly Asp Val Lys Val Glu Asp Gly Ala Asp Val Ser
195 200 205

Ile Ser Asp Leu Phe Asn Thr Arg Val Asn Lys Gly Pro Arg Val Thr
210 215 220

Val Leu Leu Gly Lys Ala Gly Met Gly Lys Thr Thr Leu Ala His Arg
225 230 235 240

Leu Cys Gln Lys Trp Ala Glu Gly His Leu Asn Cys Phe Gln Ala Leu
245 250 255

Phe Leu Phe Glu Phe Arg Gln Leu Asn Leu Ile Thr Arg Phe Leu Thr
260 265 270

Pro Ser Glu Leu Leu Phe Asp Leu Tyr Leu Ser Pro Glu Ser Asp His

-continued

```
        275                 280                 285

Asp Thr Val Phe Gln Tyr Leu Glu Lys Asn Ala Asp Gln Val Leu Leu
    290                 295                 300

Ile Phe Asp Gly Leu Asp Glu Ala Leu Gln Pro Met Gly Pro Asp Gly
305                 310                 315                 320

Pro Gly Pro Val Leu Thr Leu Phe Ser His Leu Cys Asn Gly Thr Leu
                325                 330                 335

Leu Pro Gly Cys Arg Val Met Ala Thr Ser Arg Pro Gly Lys Leu Pro
            340                 345                 350

Ala Cys Leu Pro Ala Glu Ala Ala Met Val His Met Leu Gly Phe Asp
        355                 360                 365

Gly Pro Arg Val Glu Glu Tyr Val Asn His Phe Phe Ser Ala Gln Pro
    370                 375                 380

Ser Arg Glu Gly Ala Leu Val Glu Leu Gln Thr Asn Gly Arg Leu Arg
385                 390                 395                 400

Ser Leu Cys Ala Val Pro Ala Leu Cys Gln Val Ala Cys Leu Cys Leu
                405                 410                 415

His His Leu Leu Pro Asp His Ala Pro Gly Gln Ser Val Ala Leu Leu
            420                 425                 430

Pro Asn Met Thr Gln Leu Tyr Met Gln Met Val Leu Ala Leu Ser Pro
        435                 440                 445

Pro Gly His Leu Pro Thr Ser Ser Leu Leu Asp Leu Gly Glu Val Ala
    450                 455                 460

Leu Arg Gly Leu Glu Thr Gly Lys Val Ile Phe Tyr Ala Lys Asp Ile
465                 470                 475                 480

Ala Pro Pro Leu Ile Ala Phe Gly Ala Thr His Ser Leu Leu Thr Ser
                485                 490                 495

Phe Cys Val Cys Thr Gly Pro Gly His Gln Gln Thr Gly Tyr Ala Phe
            500                 505                 510

Thr His Leu Ser Leu Gln Glu Phe Leu Ala Ala Leu His Leu Met Ala
        515                 520                 525

Ser Pro Lys Val Asn Lys Asp Thr Leu Thr Gln Tyr Val Thr Leu His
    530                 535                 540

Ser Arg Trp Val Gln Arg Thr Lys Ala Arg Leu Gly Leu Ser Asp His
545                 550                 555                 560

Leu Pro Thr Phe Leu Ala Gly Leu Ala Ser Cys Thr Cys Arg Pro Phe
                565                 570                 575

Leu Ser His Leu Ala Gln Gly Asn Glu Asp Cys Val Gly Ala Lys Gln
            580                 585                 590

Ala Ala Val Val Gln Val Leu Lys Lys Leu Ala Thr Arg Lys Leu Thr
        595                 600                 605

Gly Pro Lys Val Val Glu Leu Cys His Cys Val Asp Glu Thr Gln Glu
    610                 615                 620

Pro Glu Leu Ala Ser Leu Thr Ala Gln Ser Leu Pro Tyr Gln Leu Pro
625                 630                 635                 640

Phe His Asn Phe Pro Leu Thr Cys Thr Asp Leu Ala Thr Leu Thr Asn
                645                 650                 655

Ile Leu Glu His Arg Glu Ala Pro Ile His Leu Asp Phe Asp Gly Cys
            660                 665                 670

Pro Leu Glu Pro His Cys Pro Glu Ala Leu Val Gly Cys Gly Gln Ile
        675                 680                 685

Glu Asn Leu Ser Phe Lys Ser Arg Lys Cys Gly Asp Ala Phe Ala Glu
    690                 695                 700
```

-continued

```
Ala Leu Ser Arg Ser Leu Pro Thr Met Gly Arg Leu Gln Met Leu Gly
705                 710                 715                 720

Leu Ala Gly Ser Lys Ile Thr Ala Arg Gly Ile Ser His Leu Val Lys
                725                 730                 735

Ala Leu Pro Leu Cys Pro Gln Leu Lys Glu Val Ser Phe Arg Asp Asn
            740                 745                 750

Gln Leu Ser Asp Gln Val Val Leu Asn Ile Val Glu Val Leu Pro His
        755                 760                 765

Leu Pro Arg Leu Arg Lys Leu Asp Leu Ser Ser Asn Ser Ile Cys Val
    770                 775                 780

Ser Thr Leu Leu Cys Leu Ala Arg Val Ala Val Thr Cys Pro Thr Val
785                 790                 795                 800

Arg Met Leu Gln Ala Arg Glu Arg Thr Ile Ile Phe Leu Leu Ser Pro
                805                 810                 815

Pro Thr Glu Thr Thr Ala Glu Leu Gln Arg Ala Pro Asp Leu Gln Glu
            820                 825                 830

Ser Asp Gly Gln Arg Lys Gly Ala Gln Ser Arg Ser Leu Thr Leu Arg
        835                 840                 845

Leu Gln Lys Cys Gln Leu Gln Val His Asp Ala Glu Ala Leu Ile Ala
    850                 855                 860

Leu Leu Gln Glu Gly Pro His Leu Glu Glu Val Asp Leu Ser Gly Asn
865                 870                 875                 880

Gln Leu Glu Asp Glu Gly Cys Arg Leu Met Ala Glu Ala Ala Ser Gln
                885                 890                 895

Leu His Ile Ala Arg Lys Leu Asp Leu Ser Asp Asn Gly Leu Ser Val
            900                 905                 910

Ala Gly Val His Cys Val Leu Arg Ala Val Ser Ala Cys Trp Thr Leu
        915                 920                 925

Ala Glu Leu His Ile Ser Leu Gln His Lys Thr Val Ile Phe Met Phe
    930                 935                 940

Ala Gln Glu Pro Glu Glu Gln Lys Gly Pro Gln Glu Arg Ala Ala Phe
945                 950                 955                 960

Leu Asp Ser Leu Met Leu Gln Met Pro Ser Glu Leu Pro Leu Ser Ser
                965                 970                 975

Arg Arg Met Arg Leu Thr His Cys Gly Leu Gln Glu Lys His Leu Glu
            980                 985                 990

Gln Leu Cys Lys Ala Leu Gly Gly  Ser Cys His Leu Gly  His Leu His
        995                 1000                1005

Leu Asp  Phe Ser Gly Asn Ala  Leu Gly Asp Glu Gly  Ala Ala Arg
    1010                1015                1020

Leu Ala  Gln Leu Leu Pro Gly  Leu Gly Ala Leu Gln  Ser Leu Asn
    1025                1030                1035

Leu Ser  Glu Asn Gly Leu Ser  Leu Asp Ala Val Leu  Gly Leu Val
    1040                1045                1050

Arg Cys  Phe Ser Thr Leu Gln  Trp Leu Phe Arg Leu  Asp Ile Ser
    1055                1060                1065

Phe Glu  Ser Gln His Ile Leu  Leu Arg Gly Asp Lys  Thr Ser Arg
    1070                1075                1080

Asp Met  Trp Ala Thr Gly Ser  Leu Pro Asp Phe Pro  Ala Ala Ala
    1085                1090                1095

Lys Phe  Leu Gly Phe Arg Gln  Arg Cys Ile Pro Arg  Ser Leu Cys
    1100                1105                1110
```

-continued

```
Leu Ser  Glu Cys Pro Leu Glu  Pro Pro Ser Leu Thr  Arg Leu Cys
    1115                 1120                 1125

Ala Thr  Leu Lys Asp Cys Pro  Gly Pro Leu Glu Leu  Gln Leu Ser
    1130                 1135                 1140

Cys Glu  Phe Leu Ser Asp Gln  Ser Leu Glu Thr Leu  Leu Asp Cys
    1145                 1150                 1155

Leu Pro  Gln Leu Pro Gln Leu  Ser Leu Leu Gln Leu  Ser Gln Thr
    1160                 1165                 1170

Gly Leu  Ser Pro Lys Ser Pro  Phe Leu Leu Ala Asn  Thr Leu Ser
    1175                 1180                 1185

Leu Cys  Pro Arg Val Lys Lys  Val Asp Leu Arg Ser  Leu His His
    1190                 1195                 1200

Ala Thr  Leu His Phe Arg Ser  Asn Glu Glu Glu Glu  Gly Val Cys
    1205                 1210                 1215

Cys Gly  Arg Phe Thr Gly Cys  Ser Leu Ser Gln Glu  His Val Glu
    1220                 1225                 1230

Ser Leu  Cys Trp Leu Leu Ser  Lys Cys Lys Asp Leu  Ser Gln Val
    1235                 1240                 1245

Asp Leu  Ser Ala Asn Leu Leu  Gly Asp Ser Gly Leu  Arg Cys Leu
    1250                 1255                 1260

Leu Glu  Cys Leu Pro Gln Val  Pro Ile Ser Gly Leu  Leu Asp Leu
    1265                 1270                 1275

Ser His  Asn Ser Ile Ser Gln  Glu Ser Ala Leu Tyr  Leu Leu Glu
    1280                 1285                 1290

Thr Leu  Pro Ser Cys Pro Arg  Val Arg Glu Ala Ser  Val Asn Leu
    1295                 1300                 1305

Gly Ser  Glu Gln Ser Phe Arg  Ile His Phe Ser Arg  Glu Asp Gln
    1310                 1315                 1320

Ala Gly  Lys Thr Leu Arg Leu  Ser Glu Cys Ser Phe  Arg Pro Glu
    1325                 1330                 1335

His Val  Ser Arg Leu Ala Thr  Gly Leu Ser Lys Ser  Leu Gln Leu
    1340                 1345                 1350

Thr Glu  Leu Thr Leu Thr Gln  Cys Cys Leu Gly Gln  Lys Gln Leu
    1355                 1360                 1365

Ala Ile  Leu Leu Ser Leu Val  Gly Arg Pro Ala Gly  Leu Phe Ser
    1370                 1375                 1380

Leu Arg  Val Gln Glu Pro Trp  Ala Asp Arg Ala Arg  Val Leu Ser
    1385                 1390                 1395

Leu Leu  Glu Val Cys Ala Gln  Ala Ser Gly Ser Val  Thr Glu Ile
    1400                 1405                 1410

Ser Ile  Ser Glu Thr Gln Gln  Gln Leu Cys Val Gln  Leu Glu Phe
    1415                 1420                 1425

Pro Arg  Gln Glu Glu Asn Pro  Glu Ala Val Ala Leu  Arg Leu Ala
    1430                 1435                 1440

His Cys  Asp Leu Gly Ala His  His Ser Leu Leu Val  Gly Gln Leu
    1445                 1450                 1455

Met Glu  Thr Cys Ala Arg Leu  Gln Gln Leu Ser Leu  Ser Gln Val
    1460                 1465                 1470

Asn Leu  Cys Glu Asp Asp Asp  Ala Ser Ser Leu Leu  Leu Gln Ser
    1475                 1480                 1485

Leu Leu  Leu Ser Leu Ser Glu  Leu Lys Thr Phe Arg  Leu Thr Ser
    1490                 1495                 1500

Ser Cys  Val Ser Thr Glu Gly  Leu Ala His Leu Ala  Ser Gly Leu
```

-continued

```
    1505                1510                1515

Gly His  Cys His His Leu Glu  Glu Leu Asp Leu Ser  Asn Asn Gln
    1520                1525                1530

Phe Asp  Glu Glu Gly Thr Lys  Ala Leu Met Arg Ala  Leu Glu Gly
    1535                1540                1545

Lys Trp  Met Leu Lys Arg Leu  Asp Leu Ser His Leu  Leu Leu Asn
    1550                1555                1560

Ser Ser  Thr Leu Ala Leu Leu  Thr His Arg Leu Ser  Gln Met Thr
    1565                1570                1575

Cys Leu  Gln Ser Leu Arg Leu  Asn Arg Asn Ser Ile  Gly Asp Val
    1580                1585                1590

Gly Cys  Cys His Leu Ser Glu  Ala Leu Arg Ala Ala  Thr Ser Leu
    1595                1600                1605

Glu Glu  Leu Asp Leu Ser His  Asn Gln Ile Gly Asp  Ala Gly Val
    1610                1615                1620

Gln His  Leu Ala Thr Ile Leu  Pro Gly Leu Pro Glu  Leu Arg Lys
    1625                1630                1635

Ile Asp  Leu Ser Gly Asn Ser  Ile Ser Ser Ala Gly  Gly Val Gln
    1640                1645                1650

Leu Ala  Glu Ser Leu Val Leu  Cys Arg Arg Leu Glu  Glu Leu Met
    1655                1660                1665

Leu Gly  Cys Asn Ala Leu Gly  Asp Pro Thr Ala Leu  Gly Leu Ala
    1670                1675                1680

Gln Glu  Leu Pro Gln His Leu  Arg Val Leu His Leu  Pro Phe Ser
    1685                1690                1695

His Leu  Gly Pro Gly Gly Ala  Leu Ser Leu Ala Gln  Ala Leu Asp
    1700                1705                1710

Gly Ser  Pro His Leu Glu Glu  Ile Ser Leu Ala Glu  Asn Asn Leu
    1715                1720                1725

Ala Gly  Gly Val Leu Arg Phe  Cys Met Glu Leu Pro  Leu Leu Arg
    1730                1735                1740

Gln Ile  Asp Leu Val Ser Cys  Lys Ile Asp Asn Gln  Thr Ala Lys
    1745                1750                1755

Leu Leu  Thr Ser Ser Phe Thr  Ser Cys Pro Ala Leu  Glu Val Ile
    1760                1765                1770

Leu Leu  Ser Trp Asn Leu Leu  Gly Asp Glu Ala Ala  Ala Glu Leu
    1775                1780                1785

Ala Gln  Val Leu Pro Lys Met  Gly Arg Leu Lys Arg  Val Asp Leu
    1790                1795                1800

Glu Lys  Asn Gln Ile Thr Ala  Leu Gly Ala Trp Leu  Leu Ala Glu
    1805                1810                1815

Gly Leu  Ala Gln Gly Ser Ser  Ile Gln Val Ile Arg  Leu Trp Asn
    1820                1825                1830

Asn Pro  Ile Pro Cys Asp Met  Ala Gln His Leu Lys  Ser Gln Glu
    1835                1840                1845

Pro Arg  Leu Asp Phe Ala Phe  Phe Asp Asn Gln Pro  Gln Ala Pro
    1850                1855                1860

Trp Gly  Thr
    1865
```